US007307088B2

(12) United States Patent
Huang et al.

(10) Patent No.: US 7,307,088 B2
(45) Date of Patent: Dec. 11, 2007

(54) SUBSTITUTED ANTHRANILIC AMIDE DERIVATIVES AND METHODS OF USE

(75) Inventors: Qi Huang, Moorpark, CA (US); Guoqing Chen, Thousand Oaks, CA (US); Aiwen Li, Westlake Village, CA (US); Babak Riahi, Woodland Hills, CA (US); Andrew Tasker, Simi Valley, CA (US); Kevin Yang, San Gabriel, CA (US); Chester Chenguang Yuan, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 436 days.

(21) Appl. No.: 10/615,809

(22) Filed: Jul. 8, 2003

(65) Prior Publication Data

US 2004/0087568 A1 May 6, 2004

Related U.S. Application Data

(60) Provisional application No. 60/395,144, filed on Jul. 9, 2002.

(51) Int. Cl.
- A61K 31/4709 (2006.01)
- A61K 31/4725 (2006.01)
- A61K 31/404 (2006.01)
- A61K 31/357 (2006.01)
- C07D 217/04 (2006.01)
- C07D 215/38 (2006.01)
- C07D 209/08 (2006.01)
- C07D 319/18 (2006.01)

(52) U.S. Cl. .................. 514/310; 514/311; 514/414; 514/415; 514/456; 546/143; 546/159; 548/504; 549/362

(58) Field of Classification Search ............... 514/275, 514/310, 311, 414, 415, 456; 544/323; 546/143, 546/159; 548/504; 549/362
See application file for complete search history.

(56) References Cited

U.S. PATENT DOCUMENTS

| | | | |
|---|---|---|---|
| 3,226,394 A | 12/1965 | Schipper | |
| 3,406,168 A | 10/1968 | Schmidt | |
| 3,452,019 A | 6/1969 | Shetty | |
| 3,557,111 A | 1/1971 | Shetty | |
| 3,567,746 A | 3/1971 | Shetty | |
| 3,822,277 A | 7/1974 | Dufour | |
| 4,321,371 A | 3/1982 | Parg et al. | |
| 4,357,333 A | 11/1982 | Archibald et al. | |
| 4,563,467 A | 1/1986 | Soler | |
| 4,816,485 A | 3/1989 | Satzinger et al. | |
| 4,857,662 A | 8/1989 | Satzinger et al. | |
| 5,532,358 A | 7/1996 | Kelly | |
| 5,559,135 A | 9/1996 | Ashton et al. | |
| 5,571,912 A | 11/1996 | Grozinger et al. | |
| 5,770,613 A | 6/1998 | Gaeta et al. | |
| 6,008,234 A | 12/1999 | Kochanny et al. | |
| 6,051,713 A | 4/2000 | Teng et al. | |
| 6,140,351 A | 10/2000 | Arnaiz et al. | |
| 6,156,766 A | 12/2000 | Arita et al. | |
| 6,271,237 B1 | 8/2001 | Galemmo, Jr. et al. | |
| 6,313,122 B1 | 11/2001 | Beight et al. | |
| 6,313,151 B1 | 11/2001 | Beight et al. | |
| 6,372,759 B1 | 4/2002 | Beight et al. | |
| 6,417,200 B1 | 7/2002 | Beight et al. | |
| 6,448,277 B2 * | 9/2002 | Altmann et al. ............ 514/357 |
| 6,448,290 B1 | 9/2002 | Ohuchida et al. | |
| 6,593,352 B2 | 7/2003 | Weichert et al. | |
| 6,605,626 B2 | 8/2003 | Beight et al. | |
| 6,610,704 B1 | 8/2003 | Beight et al. | |
| 6,635,657 B1 | 10/2003 | Craft et al. | |
| 6,660,755 B2 | 12/2003 | Song et al. | |
| 6,794,397 B2 | 9/2004 | Cai et al. | |
| 2002/0052512 A1 * | 5/2002 | Fotouhi et al. ............ 548/252 |
| 2003/0069250 A1 | 4/2003 | Zhu et al. | |
| 2003/0195192 A1 | 10/2003 | Haviv et al. | |
| 2003/0195195 A1 | 10/2003 | Haviv et al. | |
| 2004/0063775 A1 | 4/2004 | Momose et al. | |
| 2004/0102441 A1 | 5/2004 | Krueger et al. | |
| 2004/0254185 A1 | 12/2004 | Ernst et al. | |
| 2005/0032816 A1 | 2/2005 | Ernst et al. | |

(Continued)

FOREIGN PATENT DOCUMENTS

DE    199 41 540 A1    3/2001

(Continued)

OTHER PUBLICATIONS

Lockeman, et al. "Nitrobenzyl Compounds and Processes in their Reduction IV" Chemische Berichte 1947, pp. 485-493.*

(Continued)

*Primary Examiner*—Rebecca Anderson
*Assistant Examiner*—Joseph R. Kosack
(74) *Attorney, Agent, or Firm*—Joseph W. Bulock; Ronald S. Hermenau

(57) ABSTRACT

Selected compounds are effective for prophylaxis and treatment of diseases, such as angiogenesis mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

18 Claims, No Drawings

U.S. PATENT DOCUMENTS

2005/0054654 A1    3/2005    Huth et al.

FOREIGN PATENT DOCUMENTS

| | | |
|---|---|---|
| DE | 100 23 486 C1 | 3/2002 |
| DE | 101 25 295 A1 | 11/2002 |
| EP | 0 001 175 A1 | 3/1979 |
| EP | 0 393 529 A1 | 10/1990 |
| EP | 0 410 148 A1 | 1/1991 |
| EP | 0 429 987 A2 | 6/1991 |
| EP | 0 393 529 B1 | 6/1993 |
| EP | 0 947 500 A1 | 10/1999 |
| FR | 2.168.227 | 1/1972 |
| GB | 1 474 296 | 5/1977 |
| JP | 58124766 | 7/1983 |
| JP | 2000-256358 | 9/2000 |
| SU | 1156362 A1 | 7/1991 |
| WO | WO 96/41795 | 12/1996 |
| WO | WO 98/45268 | 3/1998 |
| WO | WO 98/24771 | 6/1998 |
| WO | WO 99/32477 | 7/1999 |
| WO | WO 99/62885 | 12/1999 |
| WO | WO 00/02851 | 1/2000 |
| WO | WO 00/27819 | 5/2000 |
| WO | WO 00/27819 A2 * | 5/2000 |
| WO | WO 00/27820 | 5/2000 |
| WO | WO 0027819 A2 * | 5/2000 |
| WO | WO 00/39111 | 7/2000 |
| WO | WO 00/39117 | 7/2000 |
| WO | WO 00/39118 | 7/2000 |
| WO | WO 01/29009 A1 | 4/2001 |
| WO | WO 01/30745 A1 | 5/2001 |
| WO | WO 01/55114 A1 | 8/2001 |
| WO | WO 01/55115 A1 | 8/2001 |
| WO | WO 01/64643 A2 | 9/2001 |
| WO | WO 01/81311 A1 | 11/2001 |
| WO | WO 01/85671 A2 | 11/2001 |
| WO | WO 01/85691 A1 | 11/2001 |
| WO | WO 01/85715 A2 | 11/2001 |
| WO | WO 02/09349 A2 | 1/2002 |
| WO | WO 02/46148 A1 | 6/2002 |
| WO | WO 02/090352 A3 | 11/2002 |
| WO | WO 03/040101 A1 | 5/2003 |
| WO | WO 03/040102 A1 | 5/2003 |
| WO | WO 03/068232 A1 | 8/2003 |
| WO | WO 03/068235 A1 | 8/2003 |

OTHER PUBLICATIONS

Patani et al. "Bioisosterism: A Rational Approach in Drug Design" Chemical Reviews 1996, vol. 96, pp. 3147-3176.*

Breier et al., "The role of vascular endothelial growth factor in blood vessel formation", Trends in Cell Biology, 6:454-456 (1996).

Connell et al., "Patent foucs on cancer chemotherapeutics. II Angiogenesis agents: Apr. 2000-Sep. 2000", Expert Opinion on Therapeutic Patents, 11(1):77-114 (2001).

Konshin et al., "Synthesis and antimicrobial activity of aryl-amides of N-(4-pyridyl)anthranilic acid", Chemical Abstracts, 97:109837g, p. 596 (1982).

Seto et al., "Molecular Self-Assembly through Hydrogen Bonding: Supramolecular Aggregates Based on the Cyanuric Acid-Melamine Lattice", Journal of the American Chemical Society, 115:905-916 (1993).

Singh et al., "Substituted Imidazolines and their CNS Activity", Indian Journal of Heterocyclic Chemistry, 2:129-132 (1992).

Asakawa et al., "Chemistry of Salicylic Acid and Antrhanilic Acid. IV. Synthesis of 6-Chloro-5-sulfamoyl- and 6-Chloro-3-sulfamoylanthranilic Acid Derivatives", Chem. Pharm. Bull., 27(6):1287-1298 (1979).

Kovac et al., "New Synthesis of 11-Acyl-5, 11-dihydro-6H-pyrido[2,3-b][1,4]-benzodiazepin-6-ones and Related Studies", J. Heterocyclic Chem., 20:1339 (1983).

Partridge et al., "Cyclic Amidines. Part XVIII. The Synthesis of Tricycloquinazolines by Cyclodehydrogenation", J. Chem. Soc., 3670-3671 (1964).

Partridge et al., "Cyclic Amidines. Part XIX. derivatives of Triazabenzonaphthanthracene", J. Chem. Soc. Abstracts, 3673-3678 (1964).

Sanchez et al., "New 7-Anilinobenzo[b][1,8]phenanthrlines", Heterocycles, 31(11):2003-2010 (1990).

Shetty et al., "Synthesis and Activity of Some 3-Aryl- and 3-Aralkyl-1,2,3,4-tetrahydro-4-oxo-6-quinazolinesulfonamides", J. of Med. Chem., 13(5):886-895 (1970).

Proudfoot et al., "Novel Non-nucleoside Inhibitors or HIV-1 Reverse Transcriptase. 3. Dipyrido[2,3-b.2',3'-e]diazepinones", J. Med. Chem., 38:1406-1410 (1995).

Smrckova-Voltrova et al., "Structure and Properties of Quaternized 2- and 4-aminonicotinamides", Collect. Czech. Chem. Commun., 50:1009-1015 (1995).

Samvelyan et al., "Discussion of Some New Amino Acid Derivatives of Nicotinic Acid and Their Antisoporific Properties", Farmakologila Toksikologila, 49(3):35-37 (1986).

Hargrave et al., "Novel Non-Nucleoside Inhibitors of HIV-1 Reverse Transcriptase. 1. Tricyclic Pyridobenzo- and Dipyridodiazepinones", J. Med. Chem., 34:2231-2241 (1991).

Adams et al., "Discovery and Development of a Non-nucleoside Reverse Transcriptase Inhibitor", Royal Society of Chemistry, Recent Advances in the Chemistry of Anti-Infective Agents, 19:282-296 (1993).

* cited by examiner

SUBSTITUTED ANTHRANILIC AMIDE DERIVATIVES AND METHODS OF USE

This application claims the benefit of U.S. Provisional Application No. 60/395,144 filed Jul. 9, 2002, which is hereby incorporated by reference.

FIELD OF THE INVENTION

This invention is in the field of pharmaceutical agents and specifically relates to compounds, compositions, uses and methods for treating cancer and angiogenesis-related disorders.

BACKGROUND OF THE INVENTION

Protein kinases represent a large family of proteins which play a central role in the regulation of a wide variety of cellular processes, maintaining control over cellular function. A partial list of such kinases includes ab1, Akt, bcr-ab1, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed 'Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with anti-sense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Schipper U.S. Pat. No. 3,226,394, issued Dec. 28, 1965, describes anthranilamides as CNS depressants. Japanese patent JP2000256358 describes pyrazole derivatives that block the calcium release-activated calcium channel. EP application 9475000, published 6 Oct. 1999, describes compounds as PGE$_2$ antagonists. PCT publication WO96/41795, published 27 Dec. 1996, describes benzamides as vasopressin antagonists. WO01/29009 describes aminopyridines as KDR inhibitors. WO01/30745 describes anthranilic acids as cGMP phosphodiesterase inhibitors. WO00/02851, published 20 Jan. 2000 describes arylsulfonylaminoaryl amides as guanylate cyclase activators. WO98/45268 describes nicotinamide derivatives as PDE4 inhibitors. WO98/24771 describes benzamides as vasopressin antagonists.

U.S. Pat. No. 5,532,358, issued Jul. 2, 1996, describes the preparation of 2-(cyclopropylamino)-N-(2-methoxy-4-methyl-3-pyridinyl)-3-pyridinecarboxamide as an intermediate for HIV inhibitors. Triazine-substituted amines are described for their aggregating ability (J. Amer. Chem. Soc., 115:905-916 (1993). Substituted imidazolines were tested for their antidepressant activity in Ind. J. Het. Chem., 2:129-132 (1992). N-(4-Pyridyl)anthranilic amides were described in Chem Abstr. 97:109837 (1981). PCT publication WO99/32477, published 1 Jul. 1999, describes anthranilamides as anti-coagulants. U.S. Pat. No. 6,140,351 describes anthranilamides as anti-coagulants. PCT publication WO99/62885, published 9 Dec. 1999, describes 1-(4-aminophenyl)pyrazoles as antiinflammatories. PCT publication WO00/39111, published 6 Jul. 2000, describes amides as factor Xa inhibitors. PCT publication WO00/39117, published 6 Jul. 2000, describes heteroaromatic amides as factor Xa inhibitors. PCT publication WO00/27819, published 18 May 2000, describes anthranilic amides as VEGF inhibitors. PCT publication WO00/27820 published 18 May 2000, describes N-aryl anthranilic amides as VEGF inhibitors. 7-Chloroquinolinylamines are described in FR2168227 as antiinflammatories. WO01/55114, published 2 Aug. 2001, describes nicotinamides for the treatment of cancer. WO01/55115, published 2 Aug. 2001, describes nicotinamides for the treatment of apoptosis. WO01/85715, published 15 Nov. 2001, describes substituted pyridines and pyrimidines as anti-angiogenesis agents. PCT publication WO01/85691 published 15 Nov. 2001, describes anthranilic amides as VEGF inhibitors. PCT publication WO01/85671 published 15 Nov. 2001, describes anthranyl amides as VEGF inhibitors. PCT publication WO01/81311 published 1 Nov. 2001, describes anthranilic amides as VEGF inhibitors. PCT publication WO02/46148, published 13 Jun. 2002, describes anthranilic acids. However, compounds of the current invention have not been described as inhibitors of angiogenesis such as for the treatment of cancer.

DESCRIPTION OF THE INVENTION

A class of compounds useful in treating cancer and angiogenesis is defined by Formula I

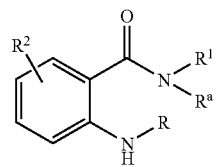

wherein R is selected from
a) unsubstituted or substituted 9- or 10-membered fused heterocyclyl,
preferably 9-membered fused nitrogen-containing heteroaryl;
more preferably indazolyl, indolyl, isoindolyl and benzotriazolyl;
even more preferably 5-indazolyl, 6-indazolyl, indolyl, isoindolyl, and benzotriazolyl, particularly 6-indazolyl; and
preferably 10-membered fused nitrogen-containing heteroaryl;
more preferably quinolinyl, isoquinolinyl, 2-oxo-1,2-dihydroquinolyl, naphthyridinyl and quinazolinyl;
even more preferably 4-quinolyl, 5-quinolyl, 6-quinolyl, 1,2-dihydroquinolyl, quinozalinyl, 4-isoquinolyl, 5-isoquinolyl, naphthyridinyl and 6-isoquinolyl, and
b) —(CH$_2$)$_{1-2}$—R$^3$,
preferably benzyl, 5-indazolyl-CH$_2$—, 4-quinolinyl-CH$_2$—, 5-isoquinolinyl-CH$_2$—, 4-quinazolinyl-CH$_2$—, (3-pyridyl)-(CH$_2$)$_2$—, (4-pyridyl)-CH$_2$—, (4-pyrimidinyl)-CH$_2$—, (5-pyrimidinyl)-CH$_2$—, (6-pyrimidinyl)-CH$_2$—, (4-pyridazinyl)-CH$_2$— and (6-pyridazinyl)-CH$_2$—;
more preferably (4-pyridyl)-CH$_2$—, (4-fluorophenyl-CH$_2$— and 4-quinolinyl-CH$_2$—;
wherein substituted R is substituted with one or more substituents selected from halo, amino, hydroxy, C$_{1-6}$-alkyl, C$_{1-6}$-haloalkyl, C$_{1-6}$-alkoxy, optionally substituted heterocyclylalkoxy, C$_{1-6}$-alkylamino-C$_{2-4}$-alkynyl, C$_{1-6}$-alkylamino-C$_{1-6}$-alkoxy, C$_{1-6}$-alkylamino-C$_{1-6}$-alkoxy-C$_{1-6}$-alkoxy, and optionally substituted heterocyclyl-C$_{2-4}$-alkynyl,
preferably chloro, fluoro, amino, hydroxy, methyl, ethyl, propyl, trifluoromethyl, dimethylaminopropynyl, 1-methylpiperdinylmethoxy, dimethylaminoethoxyethoxy, methoxy and ethoxy;
wherein R$^1$ is selected from unsubstituted or substituted
a) 5-6 membered saturated or partially saturated heterocyclyl,
b) 9-10 membered bicyclic and 13-14 membered tricyclic saturated or partially saturated heterocyclyl, and
c) phenyl;
preferably 9-10 membered saturated or partially un-saturated bicyclic heterocyclyl, and 13-14 membered saturated or partially un-saturated tricyclic heterocyclyl,
more preferably 1,2-dihydroquinolyl, 1,2,3,4-tetrahydro-isoquinolyl, 2,3-dihydro-1H-indolyl, benzo[d]isothiazolyl, 1,4-benzodioxanyl, dihydro-benzimidazolyl, 2,3,4,4a,9,9a-hexahydro-1H-3-aza-fluorenyl, 5,6,7-trihydro-1,2,4-triazolo[3,4-a]isoquinolyl, and tetrahydroquinolinyl,
wherein substituted R$^1$ is heterocyclyl substituted with one or more substituents selected from halo, C$_{1-6}$-alkyl, optionally substituted C$_{3-6}$-cycloalkyl, optionally substituted phenyl, optionally substituted phenyl-C$_1$-C$_4$-alkylenyl, C$_{1-2}$-haloalkoxy, optionally substituted phenyloxy, optionally substituted 4-6 membered heterocyclyl-C$_1$-C$_4$-alkyl, optionally substituted 4-6 membered heterocyclyl-C$_2$-C$_4$-alkenyl, optionally substituted 4-6 membered heterocyclyl, optionally substituted 4-6 membered heterocyclyloxy, optionally substituted 4-6 membered heterocyclyl-C$_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-C$_{1-4}$-alkylcarbonyl, C$_{1-2}$-haloalkyl, C$_{1-4}$-aminoalkyl, nitro, amino, hydroxy, cyano, aminosulfonyl, C$_{1-2}$-alkylsulfonyl, halosulfonyl, C$_{1-4}$-alkylcarbonyl, C$_{1-3}$-alkylamino-C$_{1-3}$-alkyl, C$_{1-3}$-alkylamino-C$_{1-3}$-alkoxy, C$_{1-3}$-alkylamino-C$_{1-3}$-alkoxy-C$_{1-3}$-alkoxy, C$_{1-4}$-alkoxycarbonyl, C$_{1-4}$-alkoxycarbonylamino-C$_{1-4}$-alkyl, C$_{1-4}$-hydroxyalkyl,

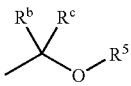

and C$_{1-4}$-alkoxy;

preferably bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-yl-propyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-yl-methoxy, pyrrol-2-ylmethoxy, 1-Boc-pyrrol-2-yl-methoxy, pyrrol-1-ylmethoxy, 1-methyl-pyrrol-2-yl-methoxy, 1-isopropyl-pyrrol-2-ylmethoxy, 1-Boc-piperdin-4-yl-methoxy, piperdin-4-ylmethoxy, 1-methylpiperdin-4-yloxy, isopropoxy, methoxy and ethoxy;

wherein substituted R$^1$ is phenyl substituted with a substituent selected from optionally substituted 4-6 membered heterocyclyl-C$_1$-C$_4$-alkyl, optionally substituted 4-6 membered heterocyclyl-C$_2$-C$_4$-alkenyl, optionally substituted 4-6 membered heterocyclyl, optionally substituted 4-6 membered heterocyclyloxy, optionally substituted 4-6 membered heterocyclyl-C$_{1-4}$-alkoxy, optionally substituted 4-6 membered heterocyclylsulfonyl, optionally substituted 4-6 membered heterocyclylamino, optionally substituted 4-6 membered heterocyclylcarbonyl, and optionally substituted 4-6 membered heterocyclyl-C$_{1-4}$-alkylcarbonyl, and optionally substituted with one or more substituents selected from halo, C$_{1-6}$-alkyl, optionally substituted C$_{3-6}$-cycloalkyl, optionally substituted phenyl, optionally substituted phenyl-C$_1$-C$_4$-alkylenyl, C$_{1-2}$-haloalkoxy, optionally substituted phenyloxy, optionally substituted 4-6 membered heterocyclyl-C$_1$-C$_4$-alkyl, optionally substituted 4-6 membered heterocyclyl-C$_2$-C$_4$-alkenyl, optionally substituted 4-6 membered heterocyclyl, optionally substituted 4-6 membered heterocyclyloxy, optionally substituted 4-6 membered heterocyclyl-C$_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-C$_{1-4}$-alkylcarbonyl, C$_{1-2}$-haloalkyl, C$_{1-4}$-aminoalkyl, nitro, amino, hydroxy, cyano, aminosulfonyl, C$_{1-2}$-alkylsulfonyl, halosulfonyl, C$_{1-4}$-alkylcarbonyl, C$_{1-3}$-alkylamino-C$_{1-3}$-alkyl, C$_{1-3}$-alkylamino-C$_{1-3}$-alkoxy, C$_{1-3}$-alkylamino-C$_{1-3}$-alkoxy-C$_{1-3}$-alkoxy, C$_{1-4}$-alkoxycarbonyl, C$_{1-4}$-alkoxycarbonylamino-C$_{1-4}$-alkyl, C$_{1-4}$-hydroxyalkyl,

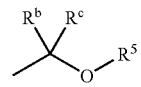

and C$_{1-4}$-alkoxy; and preferably morpholinylmethyl, 1-methylpiperazin-4-ylmethyl, 1-methylpiperazin-4-yl-propyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-yl-methoxy, 1-Boc-piperdin-4-ylmethoxy, piperdin-4-ylmethoxy, 1-methylpiperdin-4-yloxy, 1,1-di(trifluoromethyl)-1-(piperidinylethoxy)methyl, 4-methylpiperazinylsulfonyl, Boc-piperidin-1-ylmethylcarbonyl and 4-methylpiperazin-1-ylcarbonylethyl, and is optionally substituted with one or more substituents selected from bromo, chloro, fluoro, iodo, nitro, amino, cyano, aminoethyl, Boc-aminoethyl, hydroxy, oxo, aminosulfonyl, cyclohexyl, phenyl, phenylmethyl, fluorosulfonyl, methylsulfonyl, methylcarbonyl, methoxycarbonyl, aminomethylcarbonyl, dimethylaminomethylcarbonyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, isopropoxy, methoxy and ethoxy;

wherein R² is one or more substituents independently selected from
H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl,
nitro,
$C_{2-3}$-alkenyl,
$C_{2-3}$-alkynyl,
$C_{1-6}$-haloalkoxy,
$C_{1-6}$-carboxyalkyl,
4-6-membered heterocyclyl-$C_{1-6}$-alkylamino,
unsubstituted or substituted phenyl and
unsubstituted or substituted 4-6 membered heterocyclyl;
preferably H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, propynyl, morpholinylethylamino, unsubstituted or substituted phenyl and unsubstituted or substituted heteroaryl selected from thienyl, furanyl, pyridyl, imidazolyl, and pyrazolyl, and
more preferably H;
wherein R³ is independently selected from substituted or unsubstituted aryl, substituted or unsubstituted 5-6 membered heterocyclyl, and substituted or unsubstituted fused 9-, 10- or 11-membered heterocyclyl;
preferably substituted phenyl, unsubstituted or substituted 6-membered heteroaryl or unsubstituted or substituted 9- or 10-membered heteroaryl,
more preferably 3-pyridyl, 4-pyridyl, 4-pyrimidinyl, 5-pyrimidinyl, 6-pyrimidinyl, 4-pyridazinyl, 6-pyridazinyl, 5-indazolyl, 4-quinolinyl, 5-isoquinolinyl, 4-quinazolinyl and phenyl;
even more preferably 4-pyridyl, and 4-quinolinyl;
wherein substituted R³ is substituted with one or more substituents independently selected from halo, —OR⁴, —SR⁴, —SO₂R⁴, —CO₂R⁴, —CONR⁴R⁴, —COR⁴, —NR⁴R⁴, —SO₂NR⁴R⁴, —NR⁴C(O)OR⁴, —NR⁴C(O)R⁴, cycloalkyl, optionally substituted 5-6 membered heterocyclyl, optionally substituted phenyl, cyano, nitro, lower alkenyl, lower alkynyl lower alkyl substituted with R², and
preferably chloro, fluoro, amino, hydroxy, methyl, ethyl, propyl, trifluoromethyl, methoxy and ethoxy;
wherein R⁴ is independently selected from H, lower alkyl, optionally substituted phenyl, optionally substituted 4-6 membered heterocyclyl, optionally substituted $C_3$-$C_6$ cycloalkyl, phenyl-$C_{1-6}$-alkyl, optionally substituted 4-6 membered heterocyclyl-$C_{1-6}$-alkyl, and lower haloalkyl,
preferably H, $C_{1-4}$-alkyl, optionally substituted phenyl, optionally substituted phenyl-$C_{1-4}$-alkyl, optionally substituted 4-6 membered heterocyclyl, optionally substituted 4-6 membered heterocyclyl-$C_{1-4}$-alkyl, optionally substituted $C_3$-$C_6$ cycloalkyl and $C_{1-2}$-haloalkyl, and
more preferably H, methyl, phenyl, cyclopropyl, cyclohexyl, benzyl, morpholinylmethyl, 4-methylpiperazinylmethyl, azetidinyl, azetidinylmethyl, 4-methylpiperdinylmethyl, 4-morpholinylmethyl, 4-morpholinylethyl, 1-(4-morpholinyl)-2,2-dimethylpropyl, 1-piperdinylethyl, 1-piperdinylpropyl, 1-pyrrolidinylpropyl and trifluoromethyl;
wherein R⁵ is selected from H, $C_{1-3}$-alkyl, optionally substituted phenyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl,
preferably H, optionally substituted 6 membered heterocyclyl-$C_1$-$C_3$-alkyl, and $C_{1-2}$-alkoxy-$C_{1-2}$-alkoxy-$C_{1-2}$-alkyl, and
more preferably H, piperidinylethyl and methoxyethoxyethyl;
wherein Rᵃ is selected from H and $C_{1-2}$-alkyl, and preferably H; and
wherein Rᵇ and Rᶜ are independently selected from H and $C_{1-2}$-haloalkyl, and
preferably H and trifluoromethyl;

and pharmaceutically acceptable derivatives thereof.

A class of compounds useful in treating cancer and angiogenesis is defined by Formula I'

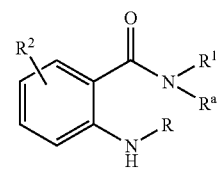

wherein R is selected from
a) unsubstituted 9- or 10-membered fused heterocyclyl and 9- or 10-membered fused heterocyclyl substituted with one or more substituents selected from halo, amino, hydroxy, $C_{1-6}$-alkyl, $C_{1-6}$-haloalkyl, $C_{1-6}$alkoxy, optionally substituted heterocyclylalkoxy, $C_{1-6}$-alkylamino-$C_{2-4}$-alkynyl, $C_{1-6}$-alkylamino-$C_{1-6}$-alkoxy, $C_{1-6}$-alkylamino-$C_{1-6}$-alkoxy-$C_{1-6}$-alkoxy, and optionally substituted heterocyclyl-$C_{2-4}$-alkynyl,
b) —(CH₂)$_{1-2}$—R³, and
c) —(CHCH₃)—R³;
wherein R¹ is selected from unsubstituted or substituted
a) 5-6 membered saturated or partially saturated heterocyclyl,
b) 9-10 membered bicyclic and 11-14 membered tricyclic saturated or partially saturated heterocyclyl, and
c) phenyl;
wherein substituted R¹ is heterocyclyl substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted 4-6 membered heterocycyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$- alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$-alkyl, $C_{1-4}$-hydroxyalkyl,

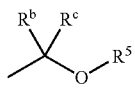

and $C_{1-4}$-alkoxy;

wherein substituted $R^1$ is phenyl substituted with a substituent selected from optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, halo, $C_3$-$C_4$-alkyl and optionally substituted 4-6 membered heterocyclyl-$C_{1-4}$-alkylcarbonyl, and the phenyl ring is optionally further substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, halosulfonyl, $C_{1-4}$-alkylcarbonyl, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-alkoxycarbonylamino-$C_{1-4}$alkyl, $C_{1-4}$-hydroxyalkyl,

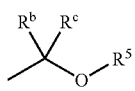

and $C_{1-4}$-alkoxy;

wherein $R^2$ is one or more substituents independently selected from H, halo, hydroxy, amino, $C_{1-6}$-alkyl, $C_{1-6}$-haloalkyl, $C_{1-6}$-alkoxy, $C_{1-2}$-alkylamino, aminosulfonyl, $C_{3-6}$-cycloalkyl, cyano, $C_{1-2}$-hydroxyalkyl, nitro, $C_{2-3}$-alkenyl, $C_{2-3}$-alkynyl, $C_{1-6}$-haloalkoxy, $C_{1-6}$-carboxyalkyl, 4-6-membered heterocyclyl-$C_{1-6}$-alkylamino, unsubstituted or substituted phenyl and unsubstituted or substituted 4-6 membered heterocyclyl;

wherein $R^3$ is independently selected from substituted or unsubstituted aryl, substituted or unsubstituted 5-6 membered heterocyclyl, and substituted or unsubstituted fused 9-, 10- or 11-membered heterocyclyl; wherein substituted $R^3$ is substituted with one or more substituents independently selected from halo, —$OR^4$, —$SR^4$, —$SO_2R^4$, —$CO_2R^4$, —$CONR^4R^4$, —$COR^4$, —$NR^4R^4$, —$SO_2NR^4R^4$, —$NR^4C(O)OR^4$, —$NR^4C(O)R^4$, cycloalkyl, optionally substituted 5-6 membered heterocyclyl, optionally substituted phenyl, lower alkyl substituted with $R^6$, cyano, nitro, lower alkenyl and lower alkynyl;

wherein $R^4$ is independently selected from H, lower alkyl, optionally substituted phenyl, optionally substituted 4-6 membered heterocyclyl, optionally substituted $C_3$-$C_6$ cycloalkyl, phenyl-$C_{1-6}$-alkyl, optionally substituted 4-6 membered heterocyclyl-$C_{1-6}$-alkyl, and lower haloalkyl;

wherein $R^5$ is selected from H, $C_{1-3}$-alkyl, optionally substituted phenyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl;

wherein $R^6$ is selected from H, halo, hydroxy, amino, $C_{1-6}$-alkoxy, $C_{1-2}$-alkylamino, aminosulfonyl, $C_{3-6}$-cycloalkyl, cyano, nitro, $C_{1-6}$-haloalkoxy, carboxy, 4-6-membered heterocyclyl-$C_{1-6}$-alkylamino, unsubstituted or substituted phenyl and unsubstituted or substituted 4-6 membered heterocyclyl;

wherein $R^a$ is selected from H and $C_{1-2}$-alkyl; and wherein $R^b$ and $R^c$ are independently selected from H and $C_{1-2}$-haloalkyl;

and pharmaceutically acceptable derivatives thereof;

provided $R^3$ is not aryl or heteroaryl when $R^1$ is unsubstituted phenyl or phenyl substituted with halo or $C_{1-6}$-alkyl and wherein $R^2$ is H.

The invention also relates to compounds of Formula I' wherein $R^1$ is selected from unsubstituted or substituted 9-10 membered bicyclic saturated or partially saturated heterocyclyl; and wherein $R^a$ is H; in conjunction with any of the above or below embodiments.

The invention also relates to compounds of Formula I' wherein $R^1$ is selected from 1,2-dihydroquinolyl, 1,2,3,4-tetrahydroquinolyl, 1,2,3,4-tetrahydroisoquinolyl, 2,3-dihydro-1H-indolyl, tetrahydroquinolinyl and 1,4-benzodioxanyl; wherein $R^1$ is unsubstituted or substituted with one or more substituents selected from bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-yl-propyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-yl-propyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5- yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-yl-methoxy, 1-isopropyl-pyrrol-2-ylmethoxy, 1-Boc-piperdin-4-yl-methoxy, piperdin-4-ylmethoxy, 1-methylpiperdin-4-yloxy, isopropoxy, methoxy and ethoxy; in conjunction with any of the above or below embodiments.

The invention also relates to compounds of Formula I' wherein $R^1$ is selected from 4,4-dimethyl-2-oxo-1,2,3,4-tetrahydroquinol-7-yl, 4,4-dimethyl-1,2,3,4-tetrahydro-isoquinol-7-yl, 2-acetyl-4,4-dimethyl-1,2,3,4-tetrahydro-isoquinol-7-yl, 2,3-dihydro-1H-indolyl, 3,3-dimethyl-2,3-dihydro-1H-indol-6-yl, 1-ethyl-3,3-dimethyl-2,3-dihydro-1H-indol-6-yl and 1-acetyl-3,3-dimethyl-2,3-dihydro-1H-indol-6-yl; in conjunction with any of the above or below embodiments.

The invention also relates to compounds of Formula I' wherein $R^1$ is 3,3-dimethyl-2,3-dihydro-1H-indol-6-yl; in conjunction with any of the above or below embodiments.

The invention also relates to compounds of Formula I' wherein $R^1$ is 4,4-dimethyl-1,2,3,4-tetrahydro-isoquinol-7-yl; in conjunction with any of the above or below embodiments.

The invention also relates to compounds of Formula I' wherein $R^1$ is selected from phenyl substituted with a substituent selected from optionally substituted 4-6 membered heterocyclyl-$C_{1-}C_4$-alkyl, optionally substituted 4-6 membered heterocyclyl-$C_{2-}C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, chloro, $C_{3-}C_4$-alkyl and optionally substituted 4-6 membered heterocyclyl-$C_{1-4}$-alkylcarbonyl; and wherein $R^a$ is H; in conjunction with any of the above or below embodiments; provided $R^3$ is not aryl or heteroaryl when $R^1$ is phenyl substituted with chloro or alkyl and wherein $R^2$ is H.

The invention also relates to compounds of Formula I' wherein $R^1$ is selected from 4-chlorophenyl, 4-tert-butylphenyl, and 4-[1-methyl-1-(1-methyl-piperidin-4-yl)-ethyl]phenyl; in conjunction with any of the above or below embodiments.

The invention also relates to compounds of Formula I' wherein $R^2$ is selected from H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl; in conjunction with any of the above or below embodiments.

The invention also relates to compounds of Formula I' wherein $R^2$ is H or fluoro; in conjunction with any of the above or below embodiments.

The invention also relates to compounds of Formula I' wherein $R^2$ is H; in conjunction with any of the above or below embodiments.

The invention also relates to compounds of Formula I' wherein R is —$(CH_2)$—$R^3$; and wherein $R^3$ is selected from phenyl substituted with one or more substituents independently selected from halo, amino, $C_{1-3}$-alkoxy, hydroxyl, $C_{1-3}$-alkyl and $C_{1-2}$-haloalkyl; in conjunction with any of the above or below embodiments.

The invention also relates to compounds of Formula I' wherein R is selected from unsubstituted or substituted 9- or 10-membered fused nitrogen-containing heterocyclyl; in conjunction with any of the above or below embodiments.

The invention also relates to compounds of Formula I' wherein R is selected from optionally substituted indazolyl, quinolinyl, [1,7]napthyridinyl, quinazolinyl and isoquinolinyl; in conjunction with any of the above or below embodiments.

The invention also relates to compounds of Formula I' wherein R is selected from [1,7]napthyridin-2-yl, quinazolin-6-yl and 7-isoquinolinyl; in conjunction with any of the above or below embodiments.

The invention also relates to compounds of Formula I' wherein R is —$(CH_2)_{1-2}$—$R^3$; and wherein $R^3$ is selected from substituted or unsubstituted 5-6 membered nitrogen-containing heteroaryl, and substituted or unsubstituted fused 9-, or 10-membered nitrogen-containing heteroaryl; in conjunction with any of the above or below embodiments.

The invention also relates to compounds of Formula I' wherein R is selected from (3-pyridyl)-$(CH_2)_2$—, (4-pyridyl)-$CH_2$—, (4-pyrimidinyl)-$CH_2$—, (5-pyrimidinyl)-$CH_2$—, (6-pyrimidinyl)-$CH_2$—, (4-pyridazinyl)-$CH_2$— and (6-pyridazinyl)-$CH_2$—; wherein R is unsubstituted or substituted with one or more substituents selected from chloro, fluoro, amino, methylamino, hydroxy, methyl, ethyl, propyl, trifluoromethyl, methoxy and ethoxy; in conjunction with any of the above or below embodiments.

The invention also relates to compounds of Formula I' wherein R is selected from 5-indazolyl-$CH_2$—, 4-quinolinyl-$CH_2$—, (1H-pyrrolo[2,3-b]pyridin-3-yl)-$CH_2$—, 5-quinoxalinyl-$CH_2$—, 5-isoquinolinyl-$CH_2$— and 4-quinazolinyl-$CH_2$—; in conjunction with any of the above or below embodiments.

The invention also relates to compounds of Formula I' wherein R is selected from (4-pyridyl)-$CH_2$—, (4-fluorphenyl)-$CH_2$—, (2-methylamino-4-pyrimidinyl)-$CH_2$—, (4-quinolinyl)-$CH_2$—, 5-quinoxalinyl-$CH_2$—, (4-pyridazinyl)-$CH_2$—, (1H-pyrrolo[2,3-b]pyridin-3-yl)-$CH_2$—, (2-methoxy-4-pyridyl)-$CH_2$—, (4-pyridazinyl)-$CH_2$—, (2-amino-4-pyrimidinyl)-$CH_2$—, quinazolin-6-yl and 7-isoquinolinyl; in conjunction with any of the above or below embodiments.

The invention also relates to compounds of Formula I' wherein R is —$(CHCH_3)$—$R^3$; wherein $R^3$ is selected from unsubstituted or substituted 6-membered nitrogen-containing heteroaryl; and wherein substituted $R^3$ is substituted with one or more substituents independently selected from halo, amino, $C_{1-3}$-alkoxy, hydroxyl, $C_{1-3}$-alkyl and $C_{1-2}$-haloalkyl; in conjunction with any of the above or below embodiments.

The invention also relates to compounds of Formula I' wherein R is selected from (4-pyridyl)-$(CHCH_3)$—, (4-pyrimidinyl)-$(CHCH_3)$—, (5-pyrimidinyl)-$(CHCH_3)$—, (6-pyrimidinyl)-$(CHCH_3)$—, (4-pyridazinyl)-$(CHCH_3)$— and (6-pyridazinyl)-(CHCH₃)—; wherein R is unsubstituted or substituted with one or more substituents selected from chloro, fluoro, amino, hydroxy, methyl, ethyl, propyl, trifluoromethyl, methoxy and ethoxy; in conjunction with any of the above or below embodiments.

The invention also relates to compounds of Formula I' wherein R is (2-methylamino-4-pyrimidinyl)-CHCH₃— or (2-amino-4-pyrimidinyl)-CHCH₃—; in conjunction with any of the above or below embodiments.

The invention also relates to compounds of Formula I' wherein $R^5$ is selected from H, piperidinylethyl and methoxyethoxyethyl; in conjunction with any of the above or below embodiments.

The invention also relates to compounds of Formula I' wherein $R^a$ is H; in conjunction with any of the above or below embodiments.

The invention also relates to compounds of Formula I' wherein $R^b$ and $R^c$ are independently selected from H and trifluoromethyl; in conjunction with any of the above or below embodiments.

A family of specific compounds of particular interest within Formulas I-I' consists of compounds and pharmaceutically-acceptable derivatives thereof as follows:

N-(3,3-dimethyl-2,3-dihydro-1H-indol-6-yl)-2-[(pyridin-4-ylmethyl)-amino]-benzamide;
N-(1-acetyl-3,3-dimethyl-2,3-dihydro-1H-indol-6-yl)-2-[(pyridin-4-ylmethyl)-amino]-benzamide;
N-(4,4-dimethyl-1,2,3,4-tetrahydro-quinolin-7-yl)-2-(quinazolin-6-ylamino)-benzamide;
N-(4,4-dimethyl-1,2,3,4-tetrahydro-isoquinolin-7-yl)-2-[(2-methylamino-pyrimidin-4-ylmethyl)-amino]-benzamide;
(R)—N-(4,4-dimethyl-1,2,3,4-tetrahydro-isoquinolin-7-yl)-2-[1-(2-methylamino-pyrimidin-4-yl)-ethylamino]-benzamide;
N-(1-Ethyl-3,3-dimethyl-2,3-dihydro-1H-indol-6-yl)-2-[(pyridin-4-ylmethyl)-amino]-benzamide;
N-(3,3-Dimethyl-2,3-dihydro-1H-indol-6-yl)-2-[(quinolin-4-ylmethyl)-amino]-benzamide;
N-(4-tert-Butyl-phenyl)-2-(isoquinolin-7-ylamino)-benzamide;
N-(4,4-Dimethyl-1,2,3,4-tetrahydro-isoquinolin-7-yl)-2-[(2-methoxy-pyridin-4-ylmethyl)-amino]-benzamide;
N-{4-[1-Methyl-1-(1-methyl-piperidin-4-yl)-ethyl]-phenyl}-2-[(pyridin-4-ylmethyl)-amino]-benzamide;
N-(1-Acetyl-3,3-dimethyl-2,3-dihydro-1H-indol-6-yl)-2-[(quinolin-4-ylmethyl)-amino]-benzamide;
N-(3,3-Dimethyl-2,3-dihydro-1H-indol-6-yl)-2-[(1-oxy-pyridin-4-ylmethyl)-amino]-benzamide;
N-(4,4-Dimethyl-1,2,3,4-tetrahydro-isoquinolin-7-yl)-2-fluoro-6-[(2-methoxy-pyridin-4-ylmethyl)-amino]-benzamide;
N-(4,4-Dimethyl-1,2,3,4-tetrahydro-isoquinolin-7-yl)-3-fluoro-6-[(2-methoxy-pyridin-4-ylmethyl)-amino]-benzamide;
N-(4,4-Dimethyl-1,2,3,4-tetrahydro-quinolin-7-yl)-2-[(1H-pyrrolo[2,3-b]pyridin-3-ylmethyl)-amino]-benzamide;
N-(4,4-Dimethyl-1,2,3,4-tetrahydro-isoquinolin-7-yl)-2-[(pyridazin-4-ylmethyl)-amino]-benzamide;
2-[1-(2-Amino-pyrimidin-4-yl)-ethylamino]-N-(4,4-dimethyl-1,2,3,4-tetrahydro-isoquinolin-7-yl)-benzamide;
N-(4,4-Dimethyl-1,2,3,4-tetrahydro-isoquinolin-7-yl)-2-[1-(2-methylamino-pyrimidin-4-yl)-ethylamino]-benzamide;
2-(4-Fluoro-benzylamino)-N-{4-[1-methyl-1-(1-methyl-piperidin-4-yl)-ethyl]-phenyl}-benzamide;
N-{4-[1-Methyl-1-(1-methyl-piperidin-4-yl)-ethyl]-phenyl}-2-[(quinolin-4-ylmethyl)-amino]-benzamide;
N-(4,4-Dimethyl-1,2,3,4-tetrahydro-isoquinolin-7-yl)-2-(4-fluoro-benzylamino)-benzamide;
N-(4,4-Dimethyl-1,2,3,4-tetrahydro-isoquinolin-7-yl)-2-fluoro-2-(4-fluoro-benzylamino)-benzamide;
N-(4,4-Dimethyl-1,2,3,4-tetrahydro-isoquinolin-7-yl)-3-fluoro-2-(4-fluoro-benzylamino)-benzamide;
N-(4,4-Dimethyl-1,2,3,4-tetrahydro-isoquinolin-7-yl)-4-fluoro-6-[(2-methoxy-pyridin-4-ylmethyl)-amino]-benzamide; and
N-(4,4-Dimethyl-2-oxo-1,2,3,4-tetrahydro-quinolin-7-yl)-2-[(1H-pyrrolo[2,3-b]pyridin-3-ylmethyl)-amino]-benzamide.

Indications

Compounds of the present invention would be useful for, but not limited to, the prevention or treatment of angiogenesis-related diseases. The compounds of the invention have kinase inhibitory activity, such as VEGFR/KDR inhibitory activity. The compounds of the invention are useful in therapy as anti-neoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, be consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anaemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of the present invention are also useful in reducing blood flow in a tumor or reducing tumor size.

The compounds of this invention may also act as inhibitors of other protein kinases, e.g. c-KIT, Flt-4, IKK, PDGFR, and bFGFR, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "treatment" includes therapeutic treatment as well as prophylactic treatment (either preventing the onset of disorders altogether or delaying the onset of a preclinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

"Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "alkoxycarbonyl" embraces alkoxy radicals, as defined above, attached to a carbonyl group. More preferred alkoxycarbonyl esters have $C_{1-4}$ alkyl portions.

The term "carbonyl", whether used alone or with other terms, such as "aminocarbonyl", denotes —(C=O)—.

The term "aminocarbonyl" denotes an amide group of the formula —$C(=O)NH_2$.

The terms "N-alkylaminocarbonyl" and "N,N-dialkylaminocarbonyl", denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkylenyl radicals are "5- or 6-membered heteroarylalkylenyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "heterocyclylalkenyl" embraces heterocyclic-substituted alkenyl radicals. More preferred heterocyclylalkenyl radicals are "5- or 6-membered heteroarylalkenyl" radicals having alkenyl portions of two to six carbon atoms and a 5- or 6-membered heteroaryl radical. Even more preferred are lower heteroarylalkenyl radicals having alkyl portions of 2-4 carbon atoms.

The term "heterocyclylalkynyl" embraces heterocyclic-substituted alkynyl radicals. More preferred heterocyclylalkynyl radicals are "5- or 6-membered heteroarylalkynyl" radicals having alkynyl portions of two to six carbon atoms and a 5- or 6-membered heteroaryl radical. Even more preferred are lower heteroarylalkynyl radicals having alkynyl portions of 2-4 carbon atoms.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heterocyclylamino" denotes amino groups which have been substituted with one or two heterocyclyl radicals. More preferred heterocyclylamino groups are "hetearylamino" wherein the heteroaryl groups are 5-6-membered heteroaryl, such as N-thienylamino. The "heteroarylamino" radicals may be further substituted on the heteroaryl ring portion of the radical. Othered preferred heterocyclylamino groups are "4-6 membered hetercyclylamino" wherein the heterocyclyl groups are 4-6-membered saturated or partially saturated heterocyclyl, optionally substituted on the hetercyclyl ring.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkoxycarbonylaminoalkyl" embraces aminoalkyl radicals substituted with alkoxycarbonyl radicals. More preferred alkoxycarbonylaminoalkyl radicals are "lower alkoxycarbonylaminoalkyl" radicals having alkyl radicals of one to six carbon atoms. Even more preferred are lower alkoxycarbonylaminoalkyl radicals having alkyl radicals of one to three carbon atoms.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkynyl" embraces alkynyl radicals substituted with alkylamino radicals. More preferred alkylaminoalkynyl radicals are "lower alkylaminoalkynyl" radicals having alkynyl radicals of two to four carbon atoms. Even more preferred are lower alkylaminoalkynyl radicals having alkyl radicals of one to six carbon atoms.

The term "alkoxyalkyl" embraces linear or branched alkyl radicals having one to about ten carbon atoms any one of which may be substituted with one or more alkoxy radicals. More preferred alkoxyalkyl radicals are "lower alkoxyalkyl" radicals having one to three carbon atoms and one or more alkoxy radicals.

The term "alkoxyalkoxyalkyl" embraces linear or branched alkoxyalkyl radicals having one to about ten carbon atoms any one of which may be substituted with an alkoxy radical. More preferred alkoxyalkoxyalkyl radicals are "lower alkoxyalkoxyalkyl" radicals having $C_{1-3}$ alkyl portions.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "alkylsulfonyl" embraces alkyl radicals, as defined above, attached to a sulfonyl group. More preferred alkylsulfonyl have $C_{1-2}$ alkyl portions.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclyloxy" embraces optionally substituted heterocyclyl radicals, as defined above, attached to an oxygen atom. More preferred heterocyclyloxy radicals are "heteroaryloxy" radicals having optionally substituted 5-6 membered heteroaryl radicals.

The term "heterocyclylalkoxy" embraces heterocyclylalkyl radicals attached through an oxygen atom to lower alkoxy radical as described above. More preferred heterocyclylalkoxy radicals are "lower heteroarylalkoxy" radicals having optionally substituted 5-6 membered heteroaryl radicals attached to an $C_{1-4}$ alkoxy radical as described above.

The term "alkylcarbonyl" embraces alkyl radicals, as defined above, attached to a carbonyl group. More preferred alkylcarbonyl have $C_{1-4}$ alkyl portions.

The term "arylcarbonyl" embraces optionally substituted aryl radicals, as defined above, attached to a carbonyl group. Examples of such radicals include phenylcarbonyl.

The term "aralkylcarbonyl" embraces aralkyl radicals attached through a carbonyl to other radicals. More preferred aralkylcarbonyl groups have $C_{1-4}$ alkyl portions.

The term "heterocyclylcarbonyl" embraces optionally substituted heterocyclyl radicals, as defined above, attached to a carbonyl group. More preferred heterocyclylcarbonyl radicals have optionally substituted 4-6 membered saturated or partially saturated heterocyclyl radicals.

The term "heterocyclylalkylcarbonyl" embraces heterocyclylalkyl radicals attached through a carbonyl group. More preferred heterocyclylalkylcarbonyl radicals are have optionally substituted 4-6 membered saturated or partially saturated heterocyclyl radicals and $C_{1-4}$ alkyl portions.

The term "heterocyclylsulfonyl" embraces optionally substituted heterocyclyl radicals; as defined above, attached to a sulfonyl group. More preferred heterocyclylsulfonyl radicals are "heteroarylsulfonyl" radicals having optionally substituted 5-6 membered heteroaryl radicals.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

The compounds of the invention are endowed with kinase inhibitory activity, such as VEGFR/KDR inhibitory activity.

The present invention also comprises the use of a compound of the invention, or a pharmaceutically-acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of VEGFR/KDR.

The present invention comprises a pharmaceutical composition comprising a therapeutically-effective amount of a compound of Formulas I-I' in association with a least one pharmaceutically-acceptable carrier, adjuvant or diluent.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formulas I-I' may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consist of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consist of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucinyttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), valspodar, Gleevec, Iressa or Avastin.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises processes for the preparation of a compound of Formulas I-I'.

Also included in the family of compounds of Formulas I-I' are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-I' may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formulas I-I' include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formulas I-I'.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically-acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases. Preferred salts include hydrochloride, phosphate and edisylate.

Additional examples of such salts can be found in Berge et al., J. Pharm. Sci., 66:1 (1977).

General Synthetic Procedures

The compounds of the invention can be synthesized according to the following procedures of Schemes 1-17, wherein the substituents are as defined for Formulas I-I', above, except where further noted.

Scheme 1

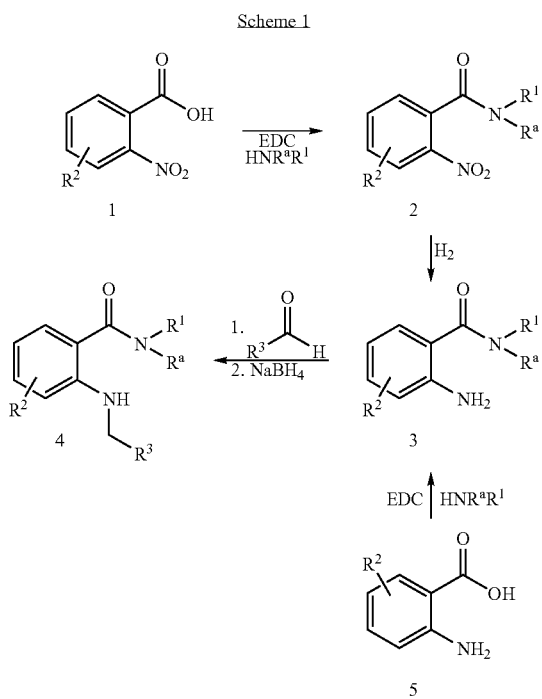

Substituted anthranilic amides 4 can be prepared from the corresponding nitro analogs 1 or the 2-aminobenzoic acids 5 by the process outlined in Scheme 1. Substituted 2-nitrobenzamides 2 are prepared from the corresponding nitro compounds 1 such as by reacting with an amine at a suitable temperature, such as about 80° C. The 2-nitrobenzamide 2 is reduced, such as with $H_2$, in the presence of a catalyst, to form the 2-aminobenzamide 3. Reductive amination of 2-aminobenzamide 3, such as by treatment with $NaBH_4$ and an aldehyde, yields the anthranilic amides 4. Alternatively, 2-aminobenzamide 3 can be prepared from 2-aminobenzoic acid 5, such as with an amine, preferably in the presence of coupling agents such as EDC and HOBt, and a base, such as DIEA.

Scheme 2

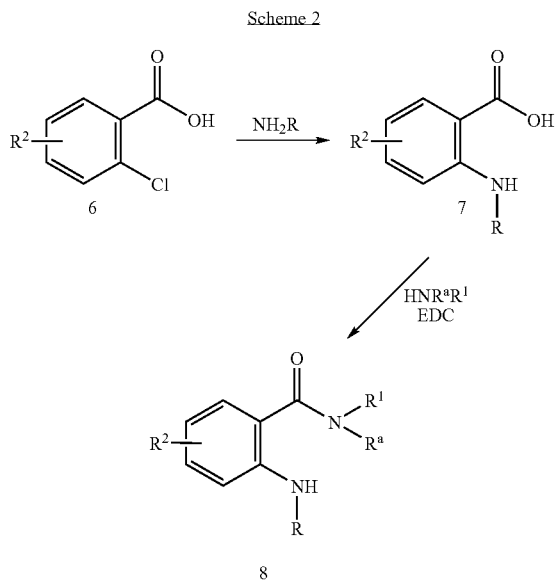

Substituted anthranilic amides 8 can be prepared from the corresponding halo analogs 6 by the process outlined in Scheme 2. Substituted 2-aminobenzoic acids 7 are prepared from the corresponding halo compounds 6 (where X is Cl, Br or I) such as by reacting with an amine at a suitable temperature, such as about 80° C. The benzoic acid 7 is coupled with an amine, preferably in the presence of a coupling agent such as EDC, to form the corresponding benzamide 8. The amination process can be carried out as an Ullmann type reaction using a copper catalyst, such as copper[0] or a copper[I] compound such as copper[I]oxide, copper[I]bromide or copper[I]iodide in the presence of a suitable base (such as a metal carbonate, for example $K_2CO_3$ to neutralize the acid generated in the reaction.

This type of reaction is reviewed in Houben-Weyl "Methoden der Organischen Chemie", Band 11/1:32-33 (1958), in Organic Reactions, 14:19-24 (1965) and by J. Lindley (1984) in Tetrahedron, 40:1433-1456. The amount of catalyst is typically in the range of 1 to 20 mole percent. The reaction is carried out in an inert, aprotic solvent such as an $Et_2O$ (for example dimethoxyethane or dioxane) or an amide (for example DMF or N-methylpyrrolidone), under an inert atmosphere in the temperature range of 60-180° C.

An alternative amination process involves using a Group VIII element, where the metal core of the catalyst should be a zero-valent transition metal, such as palladium or nickel, which has the ability to undergo oxidative addition to the aryl-halogen bond. The zero valent state of the metal may be generated in situ from the M[II] state. The catalyst complexes may include chelating ligands, such as alkyl, aryl or heteroaryl derivatives of phosphines or biphosphines, imines or arsines. Preferred catalysts contain palladium or nickel. Examples of such catalysts include palladium[II]chloride, $Pd(OAc)_2$, $Pd(PPh_3)_4$, $Pd_2(dba)_3$ and nickel[II]acetylacetonate. The metal catalyst is typically in the range of 0.1 to 10 mole percent. The chelating ligands may be either monodentate, as in the case for example of trialkyphosphines, such as tributylphosphine, triarylphosphines, such as tri-(ortho-tolyl)phosphine, and triheteroaryl phosphines, such as tri-2-furylphosphine; or they may be bidentate such as in the case of BINAP, 1,2-bis(diphenylphosphino)ethane, dppf, and 1-(N,N-dimethylamino)-1'-(dicyclohexylphosphino)biphenyl. The supporting ligand may be complexed to the metal center in the form of a metal complex prior to being added to the reaction mixture or may be added to the reaction mixture as a separate compound. The supporting ligand is typically present in the range 0.01 to 20 mole percent. It is often necessary to add a suitable base to the reaction mixture, such as a trialkylamine (for example, DIEA or 1,5-diazabicyclo[5,4,0]undec-5-ene), a Group I alkali metal alkoxide (for example potassium tert-butoxide) or carbonate (for example $Cs_2CO_3$) or potassium phosphate. The reaction is typically carried out in an inert aprotic solvent such as an ether (for example dimethoxyethane or dioxane) or an amide (for example, DMF or N-methylpyrrolidone), under an inert atmosphere in the temperature range of 60-180° C.

The amination is preferably carried out in an inert, aprotic, preferably anhydrous, solvent or solvent mixture, for example in a carboxylic acid amide, for example DMF or dimethylacetamide, a cyclic ether, for example THF or dioxane, or a nitrile, for example $CH_3CN$, or in a mixture thereof, at an appropriate temperature, for example in a temperature range of from about 40° C. to about 180° C., and if necessary under an inert gas atmosphere, for example a nitrogen or argon atmosphere.

Scheme 3

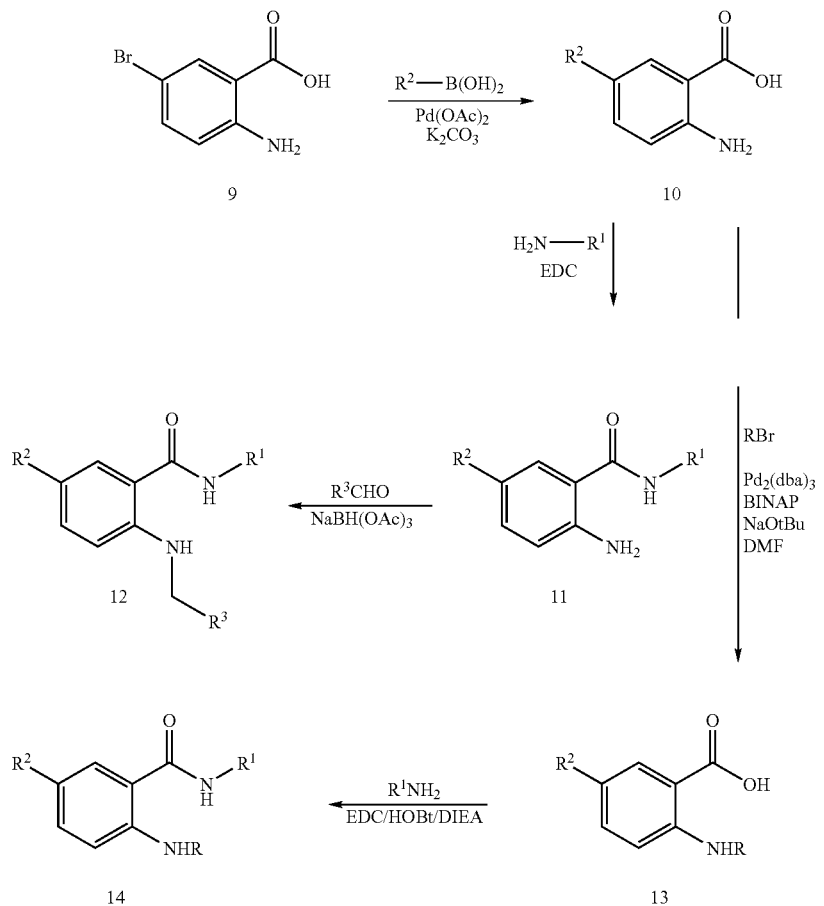

Aryl substituted anthranilamides can be prepared by the process outlined in Scheme 3. Suzuki coupling of bromoanthranilic acid 9 with a suitable boronic acid provides a substituted anthranilic acid 10, which is then converted to an amide 11 through a standard amide coupling conditions. An alkalation to the amino function with a proper aldehyde under the reductive amination conditions affords the desired compound 12. Alternatively, the aminoacid 10 can also be coupled via the Buchwald conditions with an arylbromide to produce compound 13 which is then converted to the final compound 14 via standard amide coupling conditions with a suitable amine.

Scheme 4

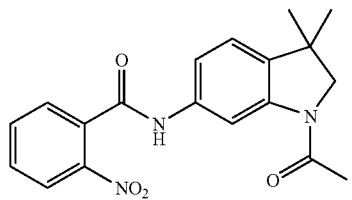

-continued

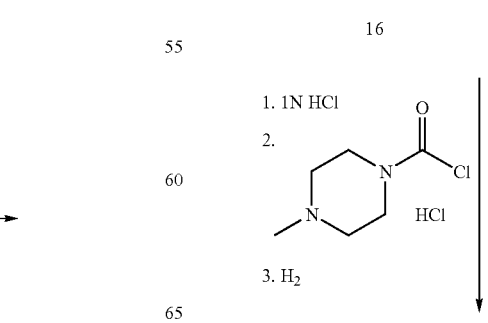

-continued

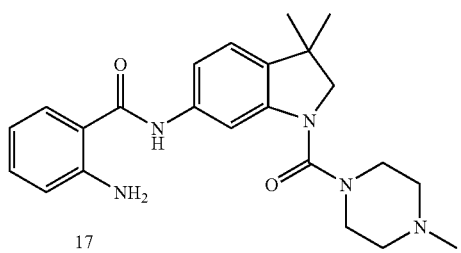

17

Substituted anthranilic amides 17 can be prepared from the corresponding nitro analogs 15 by the process outlined in Scheme 4. Substituted 2-nitrobenzamides 16 are prepared from the corresponding nitro compounds 15 such as by reacting with an amine in the presence of a coupling reagent such as EDC. The acylindoline 16 is deprotected, and then reacylated with N-methylpiperazinecarbonyl chloirde, and reduced, such as with $H_2$, in the presence of a catalyst, to form the 2-aminobenzamide 17. Reductive amination of 2-aminobenzamide 17, such as described in Scheme 1, yields the anthranilic amide.

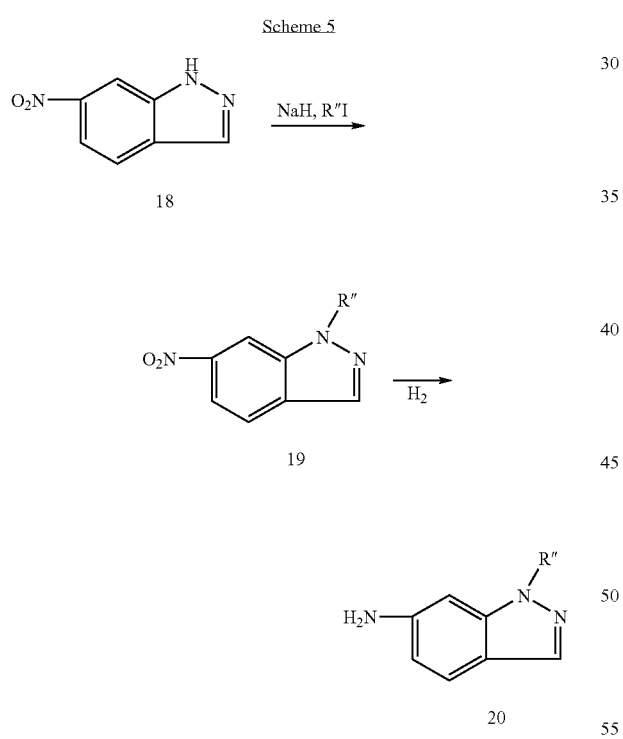

Alkylated indazoles can be prepared by the process outlined in Scheme 5. To a solution of 6-nitroindazole 18 in a solvent such as THF is added strong base, such as NaH at a temperature below RT, preferably at about 0° C. Alkylhalides, such as where R" is methyl, are added and reacted at a temperature about RT to give 1-alkyl-6-nitro-1H-indazole 19. The nitro indazole 19 is hydrogenated, such as with an $H_2$ atmosphere in the presence of a catalyst, such as Pd/C to give the 1-substituted-6-amino-1H-indazole 20.

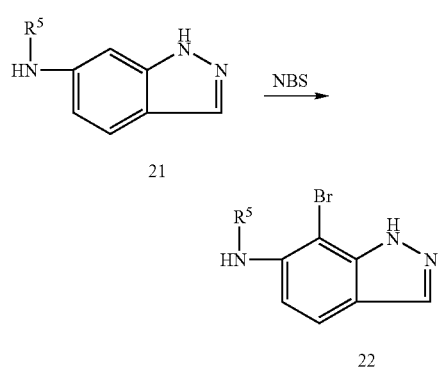

Brominated indazoles can be prepared by the process outlined in Scheme 6. NBS is slowly added to an acidic solution, such as a mixture of TFA:$H_2SO_4$ (5:1) and indazole compound 21 at a temperature of about RT to yield the brominated compound 22.

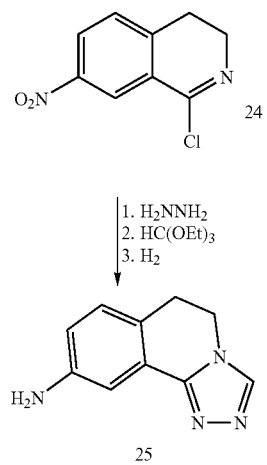

Tricyclic heterocycles can be prepared by the process outlined in Scheme 7. 7-Nitro-3,4-dihydro-2H-isoquinolin-1-one 23 is heated in $POCl_3$ at a temperature above RT, preferably at a temperature sufficient for reflux, to form the 1-chloro-7-nitro-3,4-dihydroisoquinoline 24. The 1-chloro-7-nitro-3,4-dihydroisoquinoline 24 is dissolved in a solvent, such as THF, and $H_2NNH_2$ is added. The reaction is heated with $HC(OEt)_3$ at a temperature above RT, preferably at a temperature above about 75° C., and more preferably at a temperature at about 115° C. to give the nitro-substituted tricyclic. Hydrogenation, such as with an $H_2$ atmosphere in the presence of a catalyst, such as Pd/C, gives 2-amino-5,6,7-trihydro-1,2,4-triazolo[3,4-a]isoquinoline 25.

Scheme 8

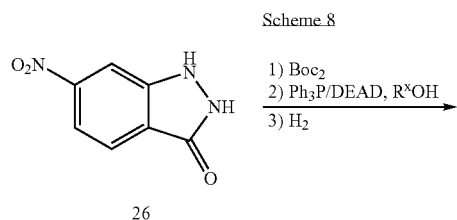

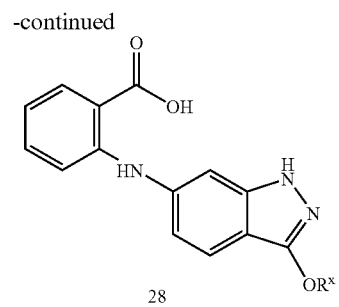

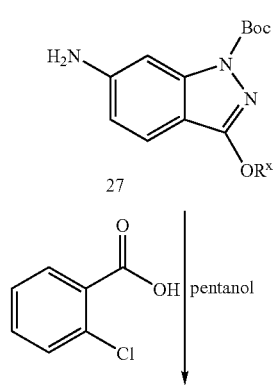

Indazolyl ethers can be prepared by the process outlined in Scheme 8. 6-Nitro-1H-2-hydroindazol-3-one 26 is protected such as with $Boc_2O$ and DMAP in $CH_2Cl_2$ at a temperature of about RT, to give the protected 6-nitro-2-hydroindazol-3-one. The protected 6-nitro-2-hydroindazol-3-one is reacted with an alcohol (where $R^x$ is an appropriate substituent selected from the possible substituents on $R^1$) and $Ph_3P$ in a solvent, such as THF, and DEAD, at a temperature of about RT, to give the protected 6-nitro (indazol-3-yl) ether. The nitro intermediate is hydrogenated, such as with an $H_2$ atmosphere in the presence of a catalyst, such as Pd/C, to give the protected 6-amino(indazol-3-yl) ether 27. The amine 27 is coupled with 2-chlorobenzoic acid, with copper as catalyst, in a solvent, such as an alcohol, preferably pentanol, at a temperature above RT, preferably at a temperature above about 75° C., and more preferably at a temperature at about 130° C. to give the coupled and deprotected compound 28.

Scheme 9

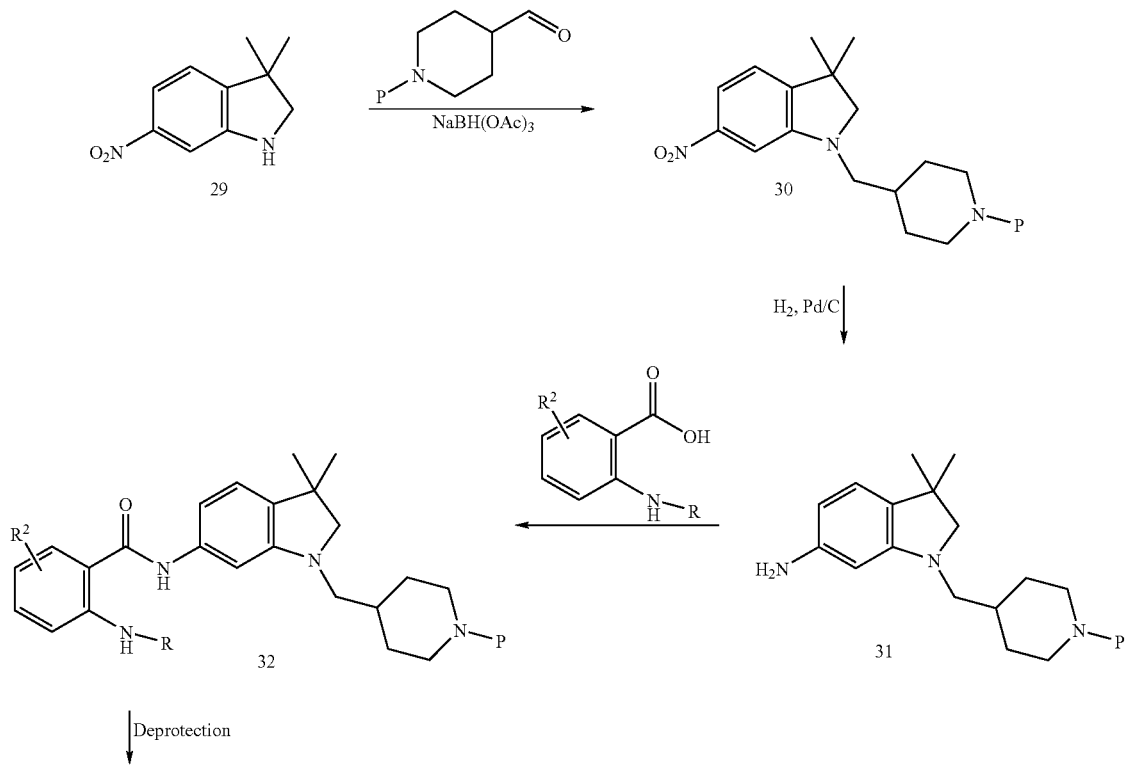

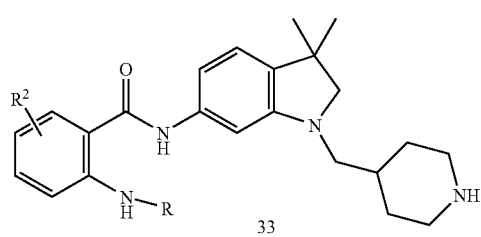
33

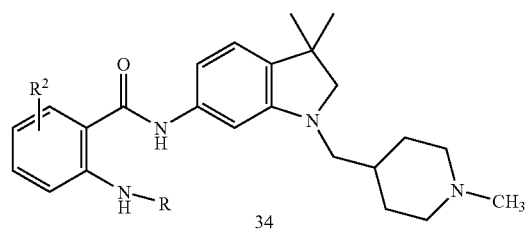
34

Indolinyl substituted carboxamides can be prepared from the corresponding nitro-indoline 29 by the process outlined in Scheme 9. For example, 3,3-dimethyl-6-nitro-indoline 29 is alkylated, such as with N-protected-4-formyl-piperidine in the presence of NaHB(OAc)$_3$ and acid, such as glacial AcOH, and solvent, such as CH$_2$Cl$_2$, at a temperature of about RT, to afford the alkylated indoline 30. Hydrogenation of the alkylated indoline 30, such as with an H$_2$ atmosphere in the presence of a catalyst, such as Pd/C, in the presence of a solvent, such as an alcohol, preferably MeOH, to give the amino intermediate 31. Alternatively, other hydrogenation methods can be used, such as SnCl$_2$ in EtOH or Fe powder with NH$_4$Cl. Coupling of the amine 31, such as with 2-chlorobenzoic acid and DIEA, HOBt and EDC, in a solvent such as CH$_2$Cl$_2$ at a temperature of about RT provides the protected carboxamide 32, which upon deprotection and alkylation yields other compounds of the invention, 33 and 34, respectively.

Substituted indolines are prepared such as by the procedures described in Scheme 10. Substituted amino-indolines 37 are prepared from the nitroindoline 35 and a ketone in the presence of NaHB(OAc)$_3$ to form the 1-substituted indoline 36. The nitroindoline 36 is hydrogenated, such as with H$_2$ in the presence of a catalyst, such as Pd/C, to yield the amino-indoline 37.

Alternatively, substituted amino-indolines 40 are prepared from the nitroindoline 35. Nitroindoline 35, is reacted with an acid chloride to form an amide. Further treatment with a primary or secondary amine, preferably a secondary amine, such as in the presence of NaI, at a temperature above about 50° C., and preferably at about 70° C. yields the nitroindoline 38. The nitro compound 38 is hydrogenated, such as with H$_2$ in the presence of a catalyst, such as Pd/C, to yield the amino-indoline 39. The carbonyl is reduced, such as with BH$_3$-THF, to yield the 1-aminoalkyl-indolines 40.

Scheme 10

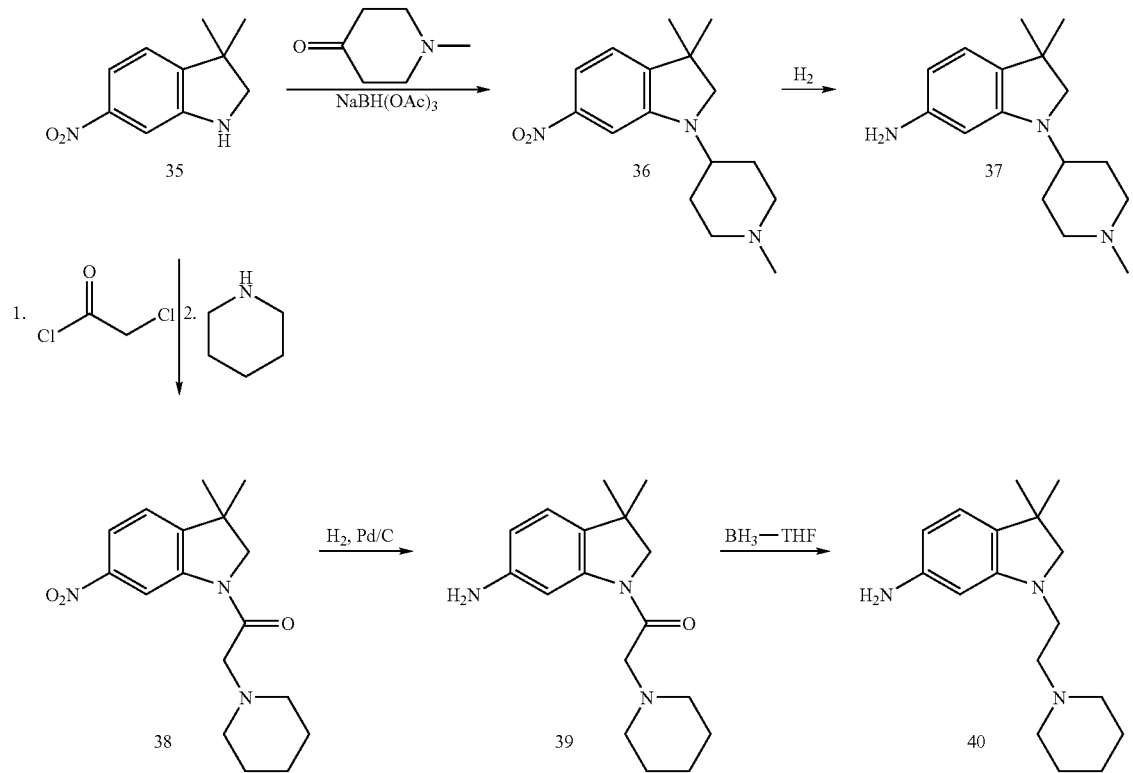

Scheme 11

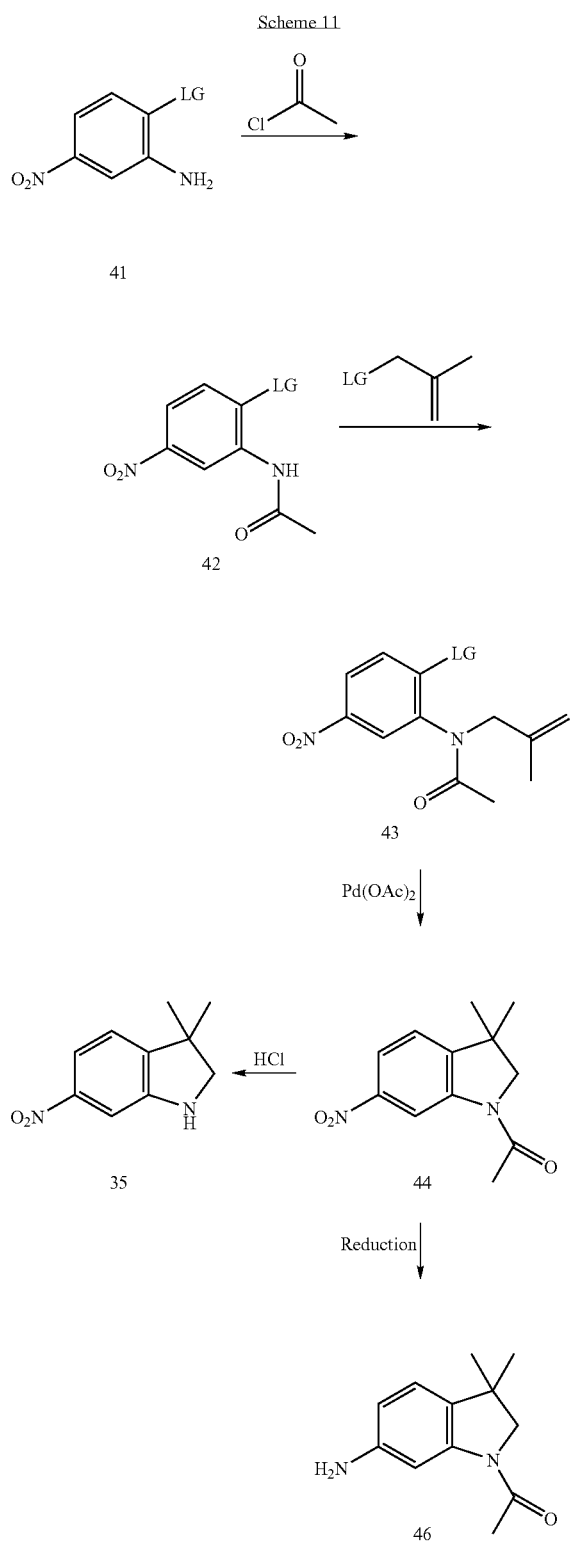

acylation conditions, such as with a base like DIEA, and DMAP or NaHCO$_3$, at a temperature of about RT, in a suitable solvent, such as CH$_2$Cl$_2$, DMF and/or DMAC. The N-(2-methylprop-2-enyl)acetamide 43 is prepared from the acetamide 42, such as by the treatment of base, such as NaH in a suitable solvent such as NMP or anhydrous DMF and a 3-halo-2-methylpropene such as 3-bromo-2-methylpropene or 3-chloro-2-methylpropene, at a temperature between about 0° C. and RT, and preferably at about RT; or with Cs$_2$CO$_3$ at a temperature above RT, preferably above about 50° C. and more preferably above about 60° C. Cyclization of the N-(2-methylprop-2-enyl)acetamide 43, such as by the Heck-type reaction (treatment with Pd(OAc)$_2$ in the presence of base, for example TEA, sodium carbonate, and NaOAc) at a temperature above about 50° C., and preferably at about 80° C., yields the protected (3,3-dimethyl-6-nitro-2,3-dihydro-indol-1-yl)ethanone 44. Deprotection, such as with strong acid such as HCl or AcOH at a temperature above about 50° C., and preferably at about 70-80° C., yields the 3,3-dimethyl-6-nitro-2,3-dihydro-indol-1-yl 35. Alternatively, the protected dihydro-6-nitro indoline 44 can be reduced, such as with Fe, or with 10% Pd/C in the presence of an excess of NH$_4$CO$_2$H, or with H$_2$ in the presence of a catalyst to form the protected dihydro-6-amino indoline 46.

Scheme 12

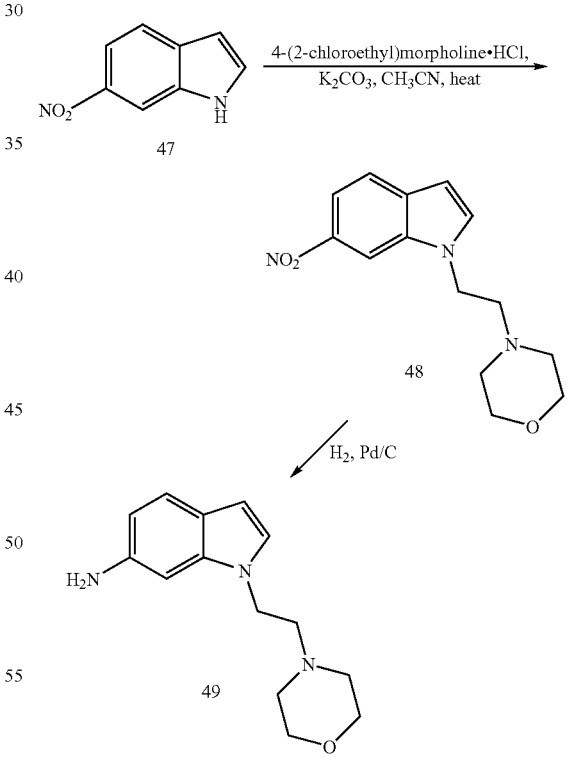

Substituted indolines are prepared such as by the procedures described in Scheme 11. Substituted acetamides 42 are prepared from the coupling of halo-5-nitroanilines 41 (where LG is bromo or chloro, preferably chloro) and an acylating agent, such as acetyl chloride, under standard Substituted indoles are prepared such as by the procedure described in Scheme 12. A nitroindole 47 is coupled with a halo compound, in the presence of base, for example K$_2$CO$_3$. Heating at a temperature above about 50° C., and preferably at about reflux yields the substituted-nitro-1H-indole 48. Hydrogenation similar to conditions described above yield the amino derivative 49.

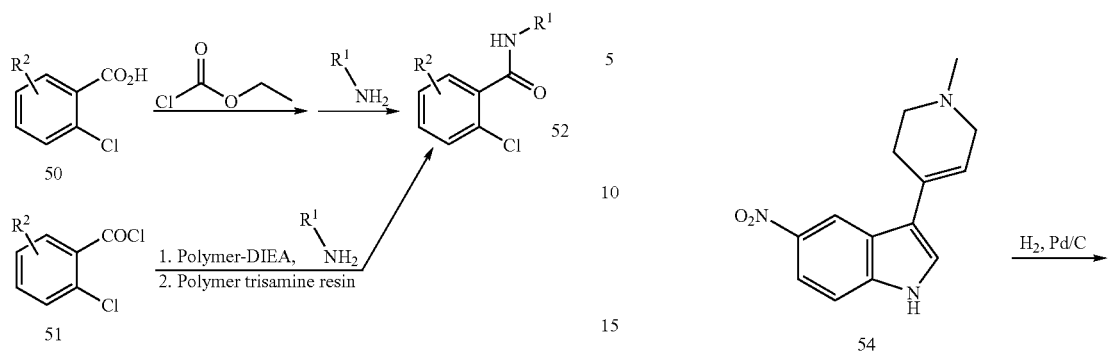

Chloro-substituted benzenes 52 are prepared such as by the procedure described in Scheme 13. 2-Chlorobenzoic acid 50 is activated with ethyl chloroformate, in the presence of a base, such as TEA, at a temperature of about RT. Reaction with an amine produces amide 52. Alternatively, the amine can be coupled with the acid chloride 51, such as with polymer-supported DIEA. Excess acid chloride is removed by treating the reaction mixture with polymer-supported trisamine resin, to form amide 52.

Amino-substituted indoles 55 are prepared such as by the procedure described in Scheme 14. Nitroindole 53 is reacted with N-methyl-4-piperidone in the presence of NaOMe at a temperature above about 50° C., and preferably at about reflux, to form the 3-substituted indole 54. Hydrogenation as previously discussed yields the amino indole 55.

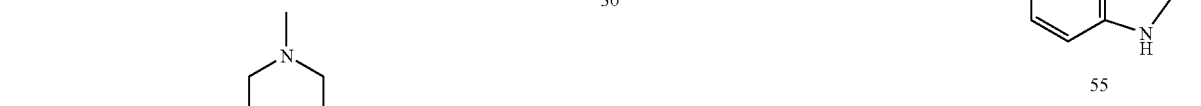

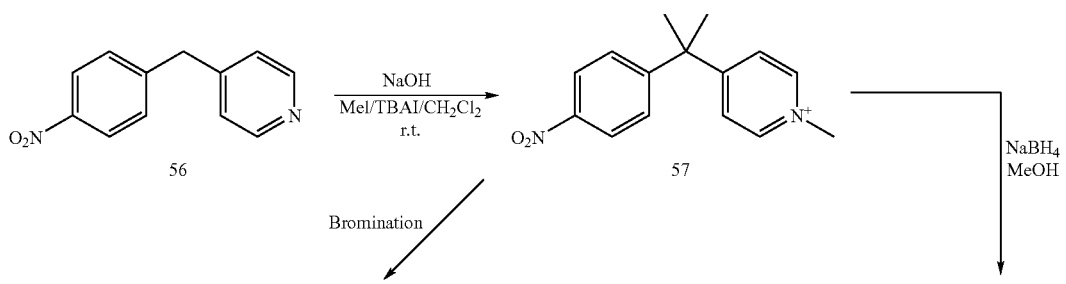

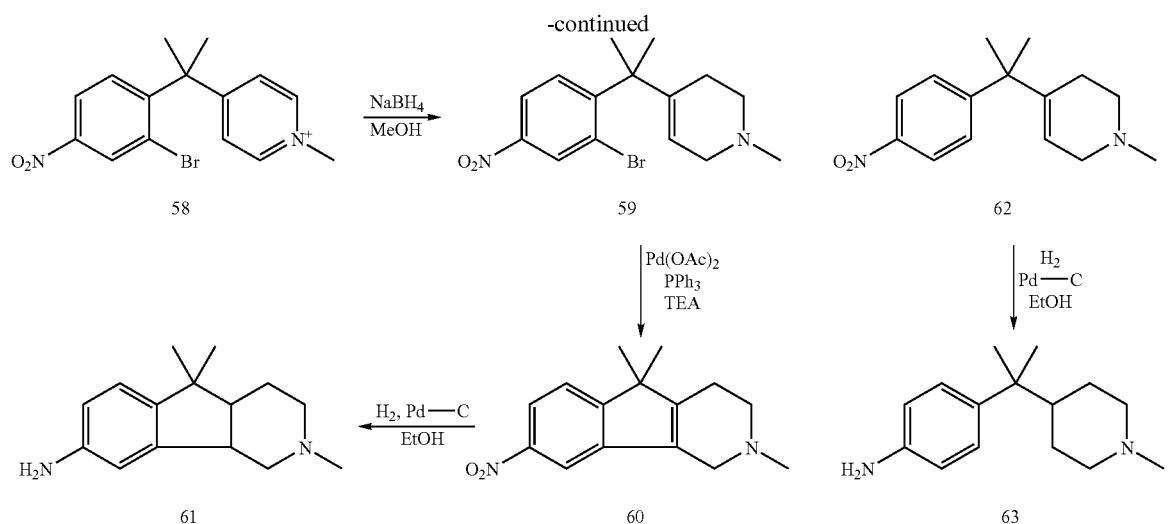

2,3,4,4a,9,9a-Hexahydro-1H-3-aza-fluoren-6-ylamine may be prepared by the method found in Scheme 15. Nitrobenzylpyridines 56 are alkylated, such as with MeI, in the presence of TBAI and base to form the pyridinium compound 57. The pyridinium compounds 57 are halogenated, such as brominated with NBS, to form the brominated pyridinium compounds 58 which are reduced such as with NaBH$_4$, to form the tetrahydropyridine 59. Heck-Type coupling delivers the tricyclic compound 60, which was reduced via catalytic hydrogenation using Pd-C to form the hexahydro-fluorenes 61. On the other hand, pyridinium salt 57 can be reduced to tetrahydropyridine 62 via such as NaBH4 in a solvent such as MeOH. The intermediate 62 was then further reduced under catalytic hydrogenation conditions to yield the bicyclic aniline 63.

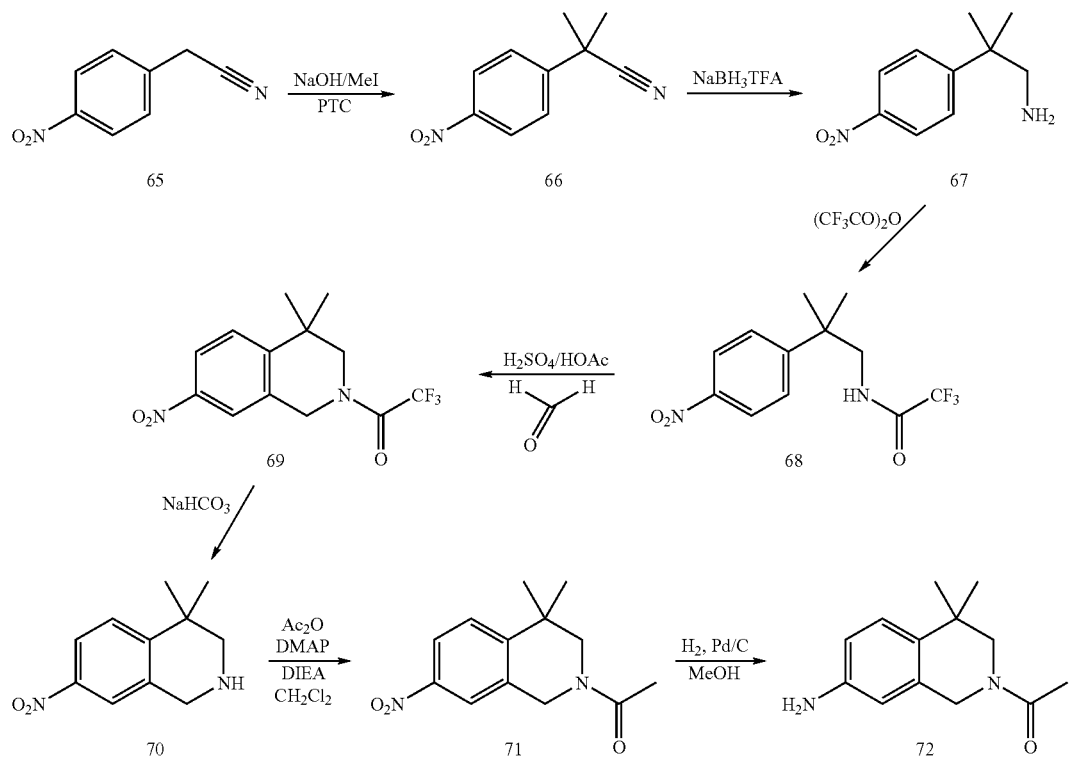

Amino-substituted 3,4-dihydro-1H-isoquinolines 72 are prepared such as by the procedure described in Scheme 16. (4-Nitro-phenyl)-acetonitrile 65 is alkylated, such as with base and alkyl halides under phase transfer conditions (PTC) using tetrabutylammonium chloride or iodide as the phase transfer reagent, to provide the alkylnitrile 66. The alkylnitrile 66 is reduced, such as by $NaBH_4$ to provide the alkylamine 67 which is protected, such as with trifluoracetic anhydride. The protected amine 68 is cyclized, such as with formaldehyde in the presence of acid, such as $H_2SO_4$ and HOAc, to form the trifluoroacetyl protected nitroisoquinline 69. The trifluoroacetyl protected nitro-isoquinline 69 is deprotected, such as with base, acylated, such as with acetic anhydride in the presence of DMAP and DIEA, then reduced to form the amino-substituted 3,4-dihydro-1H-isoquinolines 72, such as with hydrogen in the presence of catalyst, such as Pd/C.

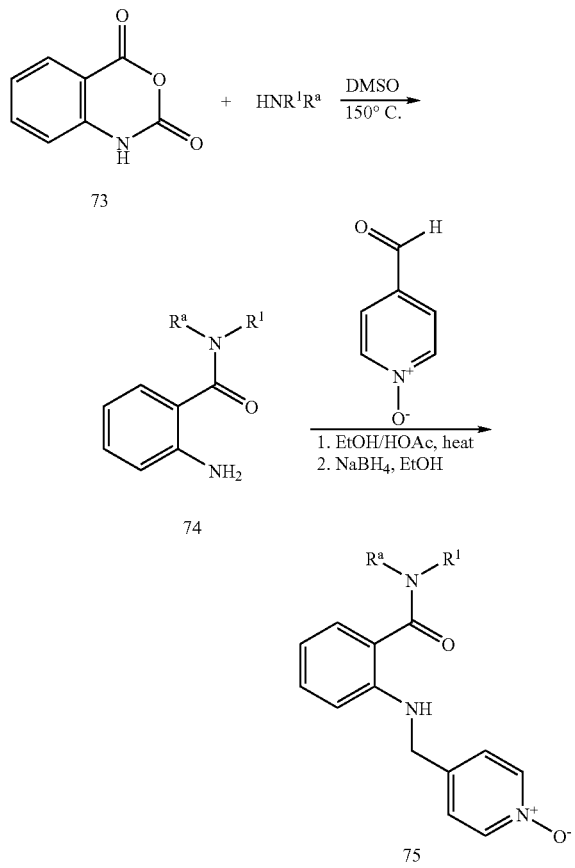

Pyridine oxide methyl amine substituted benzamides 75 can be prepared by the process outlined in Scheme 17. A mixture of a substituted amine and isatoic anhydride 73 in a solvent such as DMSO is converted to the amide 74 at a temperature above RT, preferably above about 100° C., more preferably at about 150° C. Reductive amination, such as that described in Scheme 1, with the N-oxypyridine carbaldehyde provides the benzamides 75.

The starting compounds defined in Schemes 1-17 may also be present with functional groups in protected form if necessary and/or in the form of salts, provided a salt-forming group is present and the reaction in salt form is possible. If so desired, one compound of Formulas I-I' can be converted into another compound of Formulas I-I' or a N-oxide thereof; a compound of Formulas I-I' can be converted into a salt; a salt of a compound of Formulas I-I' can be converted into the free compound or another salt; and/or a mixture of isomeric compounds of Formulas I-I' can be separated into the individual isomers.

N-Oxides can be obtained in a known matter by reacting a compound of Formulas I-I' with hydrogen peroxide, oxone, or a peracid, e.g. 3-chloroperoxy-benzoic acid, in an inert solvent, e.g. dichloromethane, or a mixture of water and an alcohol such as MeoH or EtOH, at a temperature between about −10-35° C., such as about 0° C.-RT.

If one or more other functional groups, for example carboxy, hydroxy, amino, or mercapto, are or need to be protected in a compound of Formulas I-I' or in the preparation of compounds of Formulas I-I', because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides"; Volume 3, eds. E. Gross and J. Meienhofer, Academic Press, London and New York (1981), in "Methoden der Organischen Chemie" (Methods of Organic Chemistry), Houben Weyl, $4^{th}$ edition, Volume 15(1), Georg Thieme Verlag, Stuttgart (1974), in H. -D. Jakubke and H. Jescheit, "Aminosäuren, Peptide, Proteine" (Amino acids, peptides, proteins), Verlag Chemie, Weinheim, Deerfield Beach, and Basel (1982), and in Jochen Lehmann, "Chemie der Kohlenhydrate: Monosaccharide und Derivate" (Chemistry of Carbohydrates: Monosaccharides and Derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formulas I-I' with a salt-forming group may be prepared in a manner known per se. Acid addition salts of compounds of Formulas I-I' may thus be obtained by treatment with an acid or with a suitable anion exchange reagent. A salt with two acid molecules (for example a dihalogenide of a compound of Formulas I-I') may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of Formulas I-I'.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about –100° C. to about 190° C., preferably from about –80° C. to about 150° C., for example at about –80 to about 60° C., at RT, at about –20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., EtOAc, ethers, typically aliphatic ethers, e.g., Et$_2$O, or cyclic ethers, e.g., THF, liquid aromatic hydrocarbons, typically benzene or toluene, alcohols, typically MeOH, EtOH or 1-propanol, IPOH, nitriles, typically CH$_3$CN, halogenated hydrocarbons, typically CH$_2$Cl$_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred. One may also form the compounds of Formula I-I' in vivo.

The compounds of Formulas I-I', including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

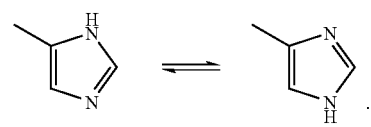

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ ed., John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ ed. (2001); M. Bodanszky, A. Bodanszky: The Practice of Peptide Synthesis Springer-Verlag, Berlin Heidelberg (1984); J. Seyden-Penne: Reductions by the Alumino- and Borohydrides in Organic Synthesis, $2^{nd}$ ed., Wiley-VCH (1997); and L. Paquette, ed., Encyclopedia of Reagents for Organic Synthesis, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a nitrogen atmosphere. Flash chromatography was performed using Aldrich Chemical Company silica gel (200-400 mesh, 60A) or Biotage pre-packed column. Thin-layer chromatography (TLC) was performed with Analtech gel TLC plates (250μ). Preparative TLC was performed with Analtech silica gel plates (1000-2000μ). Preparative HPLC was conducted on a Beckman or Waters HPLC system with 0.1% $TFA/H_2O$ and 0.1% $TFA/CH_3CN$ as mobile phase. The flow rate was at 20 mL/min. and gradient method was used. $^1H$ NMR spectra were determined with super conducting FT NMR spectrometers operating at 400 MHz or a Varian 300 MHz instrument. Chemical shifts are expressed in ppm downfield from internal standard tetramethylsilane. All compounds showed NMR spectra consistent with their assigned structures. Mass spectra (MS) were determined on a Perkin Elmer-SCIEX API 165 electrospray mass spectrometer (positive and/or negative) or an HP 1100 MSD LC-MS with electrospray ionization and quadrupole detection. All parts are by weight and temperatures are in Degrees centigrade unless otherwise indicated.

The following abbreviations are used:

| | |
|---|---|
| AcOH, HOAc - | acetic acid |
| $Ac_2O$ - | acetic anhydride |
| $Al_2O_3$ - | alumina |
| AIBN - | 2,2'-azobisisobutyronitrile |
| Ar - | argon |
| $AgSO_4$ - | silver sulfate |
| ATP - | adenosine triphosphate |
| 9-BBN - | 9-borabicyclo[3.3.1]nonane |
| $BH_3$ - | borane |
| BINAP - | 2,2'-bis(diphenylphosphino)-1,1'-binaphthyl |
| Boc - | tert-butyloxycarbonyl |
| $Boc_2O$ - | Boc anhydride |
| BOP-Cl - | bis(2-oxo-3-oxazolidinyl)phosphinic chloride |
| $Br_2$ - | bromine |
| BSA - | bovine serum albumin |
| t-BuOH - | tert-butanol |
| CAN - | ammonium cerium(IV) nitrate |
| $CH_3CN$, AcCN - | acetonitrile |
| $CH_2Cl_2$ - | dichloromethane |
| $CH_3I$, MeT - | iodomethane, methyl iodide |
| $CCl_4$ - | carbon tetrachloride |
| $CCl_3$ - | chloroform |
| $CO_2$ - | carbon dioxide |
| $Cs_2CO_3$ - | cesium carbonate |
| DIEA - | diisopropylethylamine |
| CuI - | copper iodide |
| DCE - | 1,2-dichloroethane |
| DEA - | diethylamine |
| DEAD - | diethyl azodicarboxylate |
| DIEA - | diisopropylethylamine |
| dppf - | 1,1-diphenylphosphinoferrocene |
| DMAP - | 4-(dimethylamino)pyridine |
| DMAC - | N,N-dimethylacetamide |
| DMF - | dimethylformamide |
| DMSO - | dimethylsulfoxide |
| DTT - | dithiothreitol |
| EDC, EDAC- | 1-(3-dimethylaminopropyl)-3-ethylcarbodiimide hydrochloride |

| | |
|---|---|
| EGTA - | ethylene glycol-bis(β-aminoethyl ether)-N,N,N',N'-tetraacetic acid |
| EtOAc - | ethyl acetate |
| EtOH - | ethanol |
| $Et_2O$ - | diethyl ether |
| Fe - | iron |
| g - | gram |
| h - | hour |
| HATU - | O-(7-azabenzotriazol-1-yl)-N,N,N',N'-tetramethyluronium hexafluorophosphate |
| $H_2$ - | hydrogen |
| $H_2O$ - | water |
| HCl - | hydrochloric acid |
| $H_2SO_4$ - | sulfuric acid |
| $H_2NNH_2$ - | hydrazine |
| $HC(OEt)_3$ - | triethylorthoformate |
| HCHO, $H_2CO$ - | formaldehyde |
| HCOOH - | formic acid |
| $HCO_2Na$ - | sodium formate |
| HOAc, AcOH - | acetic acid |
| HOAt - | 1-hydroxy-7-azabenzotriazole |
| HOBt - | hydroxybenzotriazole |
| IpOH, I-PrOH - | isopropanol |
| $K_2CO_3$ - | potassium carbonate |
| KHMDS - | potassium hexamethylsilazane |
| $KNO_3$ - | potassium nitrate |
| KOAc - | potassium acetate |
| KOH - | potassium hydroxide |
| LAH, $LiAlH_4$ - | lithium aluminum hydride |
| LDA - | lithium diisopropylamide |
| LiCl - | lithium chloride |
| LiHMDS - | lithium hexamethyldisilazide |
| LiOH - | lithium hydroxide |
| $LiN(TMS)_2$ - | lithium bis(trimethylsilyl)amide |
| MeOH - | methanol |
| $MgCl_2$ - | magnesium chloride |
| $MgSO_4$ - | magnesium sulfate |
| mg - | milligram |
| min - | minute |
| mL - | milliliter |
| $NnCl_2$ - | manganese chloride |
| NBS - | N-bromosuccinimide |
| NMO - | 4-methylmorpholine, N-oxide |
| NMP - | N-methylpyrrolidone |
| $Na_2SO_4$ - | sodium sulfate |
| $Na_2S_2O_5$ - | sodium metabisulfite |
| $NaHCO_3$ - | sodium bicarbonate |
| $Na_2CO_3$ - | sodium carbonate |
| NaCl - | sodium chloride |
| NaH - | sodium hydride |
| NaI - | sodium iodide |
| NaOH - | sodium hydroxide |
| NaOMe - | sodium methoxide |
| NaOtBu - | sodium tert-butoxide |
| $NaCNBH_3$ - | sodium cyanoborohydride |
| $NaBH_4$ - | sodium borohydride |
| $NaNO_2$ - | sodium nitrate |
| $NaBH(OAc)_3$ - | sodium triacetoxyborohydride |
| $NH_4Cl$ - | ammonium chloride |
| $N_2$ - | nitrogen |
| Pd/C - | palladium on carbon |
| $PdCl_2(PPh_3)_2$ - | palladium chloride bis(triphenylphosphine) |
| $Pd_2(dba)_3$ - | palladium dibenzylideneacetone |
| $PdCl_2(dppf)$ - | 1,1-bis(diphenylphosphino)ferrocene palladium chloride |
| $Pd(PPh_3)_4$ - | palladium tetrakis triphenylphosphine |
| $Pd(OH)_2$ - | palladium hydroxide |
| $Pd(OAc)_2$ - | palladium acetate |
| PMB - | para methoxybenzyl |
| $POCl_3$ - | phosphorus oxychloride |
| $PPh_3$ - | triphenylphosphine |
| $PtO_2$ - | platinum oxide |
| RT - | room temperature |
| $SiO_2$ - | silica |
| $SOCl_2$ - | thionyl chloride |
| TBAI - | tetrabutylammonium iodide |
| TBTU - | O-(1H-Benzatriazol-1-yl)-N,N,N,N-tetramethyluronium tetrafluoroborate |
| TEA - | triethylamine |
| $Tf_2NPh$ - | N-phenyltrifluoromethanesulfonimide |
| TFA - | trifluoroacetic acid |
| THF - | tetrahydrofuran |
| TPAP - | tetrapropylammoniumperruthenate |
| Tris-HCl - | Tris(hydroxymethyl)aminomethane hydrochloride salt |
| Zn - | zinc |

Preparation I—3-nitro-5-trifluoromethyl-phenol

1-Methoxy-3-nitro-5-trifluoromethyl-benzene (10 g, Aldrich) and pyridine-HCl (41.8 g, Aldrich) were mixed together and heated neat at 210° C. in an open flask. After 2.5 h the mixture was cooled to RT and partitioned between 1N HCl and EtOAc. The EtOAc fraction was washed with 1 N HCl (4×), brine (1×), dried with $Na_2SO_4$, filtered and concentrated in vacuo to form 3-nitro-5-trifluoromethyl-phenol as an off-white solid.

Preparation II—1-Boc-4-(3-nitro-5-trifluoromethyl-phenoxy)-piperidine

3-Nitro-5-trifluoromethyl-phenol (8.81 g) was dissolved in THF (76 mL). 1-Boc-4-hydroxy-piperidine (8.81 g, Aldrich) and $Ph_3P$ (11.15 g) were added and the solution was cooled to −20° C. A solution of DEAD (6.8 mL, Aldrich) in THF (36 mL) was added dropwise, maintaining the temperature between −20 and −10° C. The reaction was warmed to RT and stirred overnight. The reaction was concentrated in vacuo and triturated with hexane. The yellow solid was removed by filtration and washed with $Et_2O$ (25 mL), and hexane. The white filtrate was washed with 1 N NaOH (2×), brine (1×) and the hexane layer was dried over $Na_2SO_4$, filtered and concentrated in vacuo. The crude material was purified with flash chromatography ($SiO_2$, 5-10% EtOAc/hexane) to obtain 1-Boc-4-(3-nitro-5-trifluoromethyl-phenoxy)-piperidine.

The following compounds were prepared similarly to the procedure outlined above:

a) (S)-1-Boc-[2-(5-nitro-2-trifluoromethylphenoxymethyl]-pyrrolidine b) (R)-1-Boc-[2-(5-nitro-2-trifluoromethylphenoxymethyl]-pyrrolidine.

c) (R) 1-Boc-2-(3-Nitro-5-trifluoromethyl-phenoxymethyl)-pyrrolidine d) 4-(2-tert-Butyl-5-nitro-phenoxymethyl)-1-methyl-piperidine.

e) (S) 1-Boc-2-(3-Nitro-5-trifluoromethyl-phenoxymethyl)-pyrrolidine f) 1-Boc-3-(5-nitro-2-pentafluoroethyl-phenoxymethyl)-azetidine.

g) N-Boc-[2-(5-nitro-2-pentafluoroethyl-phenoxy)-ethyl] amine.

h) (R) 3-(2-tert-Butyl-5-nitro-phenoxymethyl)-1-Boc-pyrrolidine.

i) 3-(2-tert-Butyl-5-nitro-phenoxymethyl)-1-Boc-azetidine.

j) (S)-1-Boc-[2-(5-nitro-2-tert-butylphenoxymethyl]-pyrrolidine k) (S) 3-(2-tert-Butyl-5-nitro-phenoxymethyl)-1-Boc-pyrrolidine.

l) (R)-1-Boc-[2-(5-nitro-2-tert-butylphenoxymethyl]-pyrrolidine

Preparation III—1-Boc-4-(3-amino-5-trifluoromethyl-phenoxy)-piperidine

1-Boc-4-(3-nitro-5-trifluoromethyl-phenoxy)-piperidine (470 mg) was dissolved in MeOH (12 mL) and Pd/C (10 mg) was added. After sparging briefly with $H_2$, the mixture was stirred under $H_2$ for 6 h. The catalyst was removed by filtration and the MeOH solution was concentrated in vacuo to yield 1-Boc-4-(3-amino-5-trifluoromethyl-phenoxy)-piperidine as an off-white foam.

The following compounds were prepared similarly to the procedure outlined above:

a) 1-Boc-2-(3-Amino-5-trifluoromethyl-phenoxymethyl)-pyrrolidine.
b) 2-(3-Amino-5-trifluoromethyl-phenoxymethyl)-1-methyl-pyrrolidine.
c) [2-(1-Methylpiperidin-4-yloxy)-pyridin-4-yl]methylamine. ESI (M+H)=222.
d) [2-(2-Morpholin-4-yl-ethoxy)-pyridin-4-yl]methylamine.
e) [2-(2-Morpholin-4-yl-propoxy)-pyridin-4-yl]methylamine.
f) [2-(1-Methyl-pyrrolidin-2-ylmethoxy)-pyridin-4-yl]methylamine. ESI MS: (M+H)=222.
g) (4-Aminomethyl-pyridin-2-yl)-(3-morpholin-4-yl-propyl)-amine. ESI MS: (M+H)=251.
h) 4-tert-Butyl-3-(1-methyl-piperidin-4-ylmethoxy)-phenylamine.
i) 4-tert-Butyl-3-(2-piperidin-1-yl-ethoxy)-phenylamine.
j) 3-(1-Methyl-piperidin-4-ylmethoxy)-4-pentafluoroethyl-phenylamine.
k) 3-(1-Isopropyl-piperidin-4-ylmethoxy)-4-pentafluoroethyl-phenylamine.
l) (S) 3-Oxiranylmethoxy-4-pentafluoroethyl-phenylamine.
m) 3-(2-Pyrrolidin-1-yl-ethoxy)-4-trifluoromethyl-phenylamine.
n) 3-(2-Piperidin-1-yl-ethoxy)-4-trifluoromethyl-phenylamine.
o) (S) 3-(1-Boc-pyrrolidin-2-ylmethoxy)-4-pentafluoroethyl-phenylamine.
p) (R) 3-(1-Boc-pyrrolidin-2-ylmethoxy)-4-pentafluoroethyl-phenylamine.
q) (R) 3-(1-Methyl-pyrrolidin-2-ylmethoxy)-5-trifluoromethyl-phenylamine.
r) (S) 3-(1-Methyl-pyrrolidin-2-ylmethoxy)-5-trifluoromethyl-phenylamine
s) (R) 3-Oxiranylmethoxy-4-pentafluoroethyl-phenylamine.
t) (R) 2-(5-Amino-2-pentafluoroethyl-phenoxy)-1-pyrrolidin-1-yl-ethanol.
u) 3-(1-Boc-azetidin-3-ylmethoxy)-4-pentafluoroethyl-phenylamine.
v) 3-(2-(Boc-amino)ethoxy)-4-pentafluoroethyl-phenylamine.
w) 6-Amino-2,2-dimethyl-4H-benzo[1,4]oxazin-3-one. M+H 193.2. Calc'd 192.1.
x) 2,2,4-Trimethyl-3,4-dihydro-2H-benzo[1,4]oxazin-6-ylamine.
y) 1-(6-Amino-2,2-dimethyl-2,3-dihydro-benzo[1,4]oxazin-4-yl)-ethanone. M+H 221.4. Calc'd 220.3.
z) [2-(1-Benzhydryl-azetidin-3-yloxy)-pyridin-4-yl]-methylamine.
aa) [2-(1-Methyl-piperidin-4-ylmethoxy)-pyridin-4-yl]-methylamine. M+H 236.3. Calc'd 235.2.
ab) 3-(4-Boc-piperazin-1-ylmethyl)-5-trifluoromethyl-phenylamine. M+H 360.3.
ac) 2-Boc-4,4-dimethyl-1,2,3,4-tetrahydro-isoquinolin-7-ylamine.
ad) 3-Morpholin-4-ylmethyl-4-pentafluoroethyl-phenylamine.
ae) 3-(4-Methyl-piperazin-1-ylmethyl)-4-pentafluoroethyl-phenylamine. M+H 410.3. Calc'd 409.4.
af) 7-Amino-2-(4-methoxy-benzyl)-4,4-dimethyl-3,4-dihydro-2H-isoquinolin-1-one. M+H 311.1.
ag) 7-Amino-4,4-dimethyl-3,4-dihydro-2H-isoquinolin-1-one.
ah) (3-Amino-5-trifluoromethyl-phenyl)-(4-Boc-piperazin-1-yl)-methanone. M+H 374.3; Calc'd 373.
ai) 3-(4-Boc-Piperazin-1-ylmethyl)-5-trifluoromethyl-phenylamine.
aj) 1-(7-Amino-4,4-dimethyl-3,4-dihydro-1H-isoquinolin-2-yl)-ethanone. M+H 219.2.
ak) {2-[2-(1-Methylpiperidin-4-yl)ethoxy]-pyridin-4-yl}-methylamine.
al) {2-[2-(1-Pyrrolidinyl)ethoxy]-pyridin-4-yl}-methylamine.
am) {2-[2-(1-Methylpyrrolin-2-yl)ethoxy]-pyridin-4-yl}-methylamine.
an) (2-Chloro-pyrimidin-4-yl)-methylamine.
ao) 3-(1-Boc-azetidin-3-ylmethoxy)-5-trifluoromethyl-phenylamine.
ap) 4-tert-Butyl-3-(1-Boc-pyrrolidin-3-ylmethoxy)phenylamine. M+H 385.
aq) 4-tert-Butyl-3-(1-Boc-azetidin-3-ylmethoxy)-phenylamine. M+Na 357.
ar) (S) 4-tert-Butyl-3-(1-Boc-pyrrolidin-2-ylmethoxy)-phenylamine. M+Na 371.
as) 3-tert-Butyl-4-(4-Boc-piperazin-1-yl)-phenylamine
at) 3-(1-Methyl-piperidin-4-yl)-5-trifluoromethyl-phenylamine.
au) 3,3-Dimethyl-2,3-dihydro-benzofuran-6-ylamine.
av) 3,9,9-Trimethyl-2,3,4,4a,9,9a-hexahydro-1H-3-azafluoren-6-ylamine.
aw) 4-[1-Methyl-1-(1-methyl-piperidin-4-yl)-ethyl]-phenylamine was prepared using EtOH as the solvent.
ax) 4-tert-Butyl-3-(4-pyrrolidin-1-yl-but-1-enyl)-phenylamine.
ay) (R) 3-(1-Boc-pyrrolidin-2-ylmethoxy)-5-trifluoromethyl-phenylamine.
az) (S) 3-(1-Boc-pyrrolidin-2-ylmethoxy)-5-trifluoromethyl-phenylamine.

Preparation IV—2-(3-nitro-5-trifluoromethyl-phenoxymethyl)-pyrrolidine

1-Boc-2-(3-nitro-5-trifluoromethyl-phenoxymethyl)-pyrrolidine (2.35 g) was dissolved in $CH_2Cl_2$ (60 mL) and TFA (20 mL) was added. After stirring for 1 h at RT, the mixture was concentrated in vacuo to yield 2-(3-nitro-5-trifluoromethyl-phenoxymethyl)-pyrrolidine as an oil that solidified upon standing. The material was used as is without further purification.

The following compounds were prepared similarly to the procedure outlined above:

a) (4-Aminomethyl-pyrimidin-2-yl)-(3-morpholin-4-yl-propyl)-amine.
b) (4-Aminomethyl-pyrimidin-2-yl)-[2-(1-methyl-pyrrolidin-2-yl)-ethyl]-amine.

Preparation V—1-methyl-2-(3-nitro-5-trifluoromethyl-phenoxymethyl)-pyrrolidine 2-(3-Nitro-5-trifluoromethyl-phenoxymethyl)-pyrrolidine (6 mmol) was dissolved in $CH_3CN$ (20 mL) and formaldehyde (2.4 mL, 37% aqueous) was added. $NaBH_3CN$ (607 mg) was added, an exotherm was observed. The pH is monitored every 15 min and adjusted to ~7 with AcOH. After 45 min, the mixture was concentrated in vacuo and the residue is dissolved in EtOAc, washed with 6N NaOH, 1N NaOH, and 2N HCl (3×). The acid washings were combined, adjusted to ~pH 10 with solid $Na_2CO_3$ and extracted with EtOAc (2×) The EtOAc fractions were combined, dried with $Na_2SO_4$, and purified with flash chromatography ($SiO_2$, 95:5:0.5 $CH_2Cl_2$:MeOH:$NH_4OH$) to afford 1-methyl-2-(3-nitro-5-trifluoromethyl-phenoxymethyl)-pyrrolidine.

The following compounds were prepared similarly to the procedure outlined above:
a) 2-(1-Methylpiperidin-4-yl)-ethanol.
b) 2-{3-[(2-Fluoro-pyridine-3-carbonyl)-amino]-5-trifluoromethyl-phenoxymethyl}-1-methylpyrrolidine.

Preparation VI—4-tert-butyl-3-nitro-phenylamine

A mixture of 1,3-dinitro-4-tert-butylbenzene (10.0 g) in $H_2O$ (56 mL) was heated to reflux. A mixture of $Na_2S$ (21.42 g) and sulfur (2.85 g) in $H_2O$ (34 mL) was added over 1 h via an addition funnel. The reaction maintained at reflux for 1.5 h then cooled to RT and extracted with EtOAc. The organic extracts were combined and washed with $H_2O$, brine, dried over $MgSO_4$ and concentrated in vacuo to afford 4-tert-butyl-3-nitro-phenylamine which was used as is without further purification.

Preparation VII—N-(3-bromo-5-trifluoromethyl-phenyl)-acetamide

3-Bromo-5-(trifluoromethyl)phenylamine (5 g, Alfa-Aesar) was dissolved in AcOH (140 mL) and $Ac_2O$ (5.9 mL, Aldrich) was added. The reaction was stirred at RT overnight. The mixture was added slowly to $H_2O$ (~700 mL) forming a white precipitate. The solid was isolated by filtration, washed with $H_2O$ and dried under vacuum to yield N-(3-bromo-5-trifluoromethyl-phenyl)-acetamide.

Preparation VIII—N-[3-(3-piperidin-1-yl-propyl)-5-trifluoromethyl-phenyl]-acetamide Allylpiperidine (1.96 g, Lancaster) was degassed under vacuum, dissolved in 0.5 M 9-BBN in THF (31.2 mL, Aldrich), and heated to reflux for 1 h, then cooled to RT. Pd(dppf)$Cl_2$/$CH_2Cl_2$ was added to a degassed mixture of N-(3-bromo-5-trifluoromethyl-phenyl)-acetamide, $K_2CO_3$ (9.8 g) DMF (32.1 mL and $H_2O$ (3 mL). The allyl piperidine solution was added heated to 60° C. for 3 h. After cooling to RT and reheating at 60° C. for 6 h, the mixture was cooled to RT and poured into $H_2O$. The mixture was extracted with EtOAc (2×), and the EtOAc portion was washed with 2 N HCl (2×) and brine. The aqueous phases were combined and the pH was adjusted to ~11 with NaOH (15%) forming a cloudy suspension. The cloudy suspension was extracted with EtOAc (2×) and the EtOAc portion was dried with $Na_2SO_4$, filtered and concentrated in vacuo. The crude material was purified by flash chromatography ($SiO_2$, 95:5:0.5 $CH_2Cl_2$:MeOH:$NH_4OH$) to afford N-[3-(3-piperidin-1-yl-propyl)-5-trifluoromethyl-phenyl]-acetamide as a brown oil that solidified under vacuum.

The following compounds were prepared similarly to the procedure outlined above:
a) N-(3-Morpholin-4-ylpropyl-5-trifluoromethyl-phenyl)-acetamide from 4-allyl-morpholine.
b) N-(3-(1-methylpiperdin-4-ylmethyl-5-trifluoromethyl-phenyl)-acetamide from 1-Methyl-4-methylene-piperidine.

Preparation IX—3-(3-piperidin-1-yl-propyl)-5-trifluoromethyl-\phenylamne

N-[3-(3-Piperidin-1-yl-propyl)-5-trifluoromethyl-phenyl]-acetamide (1.33 g) was dissolved in EtOH (40 mL) and 12 N HCl (40 mL) was added. After stirring overnight at 70° C. and RT, the mixture was concentrated in vacuo, affording 3-(3-piperidin-1-yl-propyl)-5-trifluoromethyl-phenylamine as a brown oil.

The following compounds were prepared similarly to the procedure outlined above:
a) 3,3-Dimethyl-6-nitro-2,3-dihydro-1H-indole. M+H 193.1; Calc'd 192.2.
b) 3-(1-Methyl-piperidin-4-ylmethyl)-5-trifluoromethyl-phenylamine.
c) 3-Morpholin-4-ylmethyl-5-trifluoromethyl-phenylamine.

Preparation X—3,3-Dimethyl-6-nitro-1-piperidin-4-ylmethyl-2,3-dihydro-1H-indole 3,3-dimethyl-1-(1-Boc-piperidin-4-ylmethyl)-6-nitro-2,3-dihydro-1H-indole was dissolved in HCl/EtOAc and stirred for 2 h. The mixture was concentrated in vacuo and partitioned between DCE and 1N NaOH. The organic layer was removed, washed with brine, dried ($Na_2SO_4$) and filtered. The material was used without further purification.

Preparation XI—N-[3-(3-morpholin-4-yl-propyl)-5-trifluoromethyl-phenyl]-acetamide N-[3-(3-Morpholin-4-yl-propyl)-5-trifluoromethyl-phenyl]-acetamide was prepared from allyl morpholine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XII—3-(3-morpholin-4-yl-propyl)-5-trifluoromethyl-phenylamine 3-(3-Morpholin-4-yl-propyl)-5-trifluoromethyl-phenylamine was prepared from N-[3-(3-morpholin-4-yl-propyl)-5-trifluoromethyl-phenyl]-acetamide similar to that described in the preparation of 3-(3-piperidin-1-yl-propyl)-5-trifluoromethyl-phenylamine.

Preparation XIII—1-methyl-4-methylene-piperidine $Ph_3PCH_3I$ (50 g, Aldrich) was suspended in $Et_2O$ (20 mL) and butyllithium (77.3 mL, 1.6 M in hexanes, Aldrich) was added dropwise. The reaction was stirred for 2 h at RT then 1-methylpiperidone (12.3 mL, Aldrich) was added slowly. The mixture was stirred at RT overnight. The solid was removed by filtration, the volume was reduced to ~400 mL and additional solid was removed by filtration. The $Et_2O$ was washed with $H_2O$ (2×) and 2 N HCl (4×). The pH of the acid washings was adjusted to ~11 with 6 N NaOH, then they were extracted with $CH_2Cl_2$ (4×). The $CH_2Cl_2$ washings were dried over $Na_2SO_4$ and concentrated cold in vacuo to provide 1-methyl-4-methylene-piperidine which was used as is.

Preparation XIV—N-[3-(1-methylpiperidin-4-yl)-5-trifluoromethyl-phenyl]-acetamide N-[3-(1-Methylpiperidin-4-yl)-5-trifluoromethyl-phenyl]-acetamide was prepared from 1-methyl-4-methylene-piperidine and N-(3-bromo-5-trifluoromethyl-phenyl)-acetamide similar to that described in the preparation of N-[3-(3-piperidin-1-yl-propyl)-5-trifluoromethyl-phenyl]-acetamide.

Preparation XV—3-(1-methylpiperidin-4-yl)-5-trifluoromethyl-phenylamine 3-(1-Methylpiperidin-4-yl)-5-trifluoromethyl-phenylamine was prepared from N-[3-(1-methylpiperidin-4-yl)-5-trifluoromethyl-phenyl]-acetamide similar to the procedure described in the preparation of 3-(3-piperidin-1-yl-propyl)-5-trifluoromethyl-phenylamine.

Preparation XVI—2-morpholin-4-yl-propanol

LAH powder (1.6 g) was added to a flask while under $N_2$ atmosphere, immediately followed by THF (50 mL). The mixture was chilled to 0° C., methyl 2-morpholin-4-yl-propionate (5 g) was added dropwise to the reaction mixture and stirred at 0° C. After 1 h, the mixture was worked up by adding $H_2O$ (44 mL), 2N NaOH (44 mL), then $H_2O$ (44 mL, 3×). After 30 min of stirring, the mixture was filtered through Celite® and the organic portion was concentrated in vacuo providing 2-morpholin-4-yl-propanol as a colorless oil.

a) (1-Methyl-piperidin-4-yl)-methanol. (M+H 130.2. Calc'd 129.1) was prepared similarly to that outlined above.

Preparation XVII—5-Nitro-2-pentafluoroethylphenol

Combined 2-methoxy-4-nitro-1-pentafluoroethyl-benzene (9.35 g) and pyridine hydrochloride in a round bottom flask and heated at 210° C. for 1 h then cooled to RT. The mixture was diluted with EtOAc and 2 N HCl (>500 mL) until all residue dissolved. The organic layer was removed, washed with 2 N HCl (2×) and concentrated in vacuo. The residue was dissolved in hexanes and $Et_2O$, washed with 2 N HCl, then brine. Dried organic layer over $Na_2SO_4$, filtered, concentrated in vacuo and dried under high vacuum to provide 5-nitro-2-pentafluoromethylphenol.

Preparation XVIII—2-tert-Butyl-5-nitro-aniline

To $H_2SO_4$ (98%, 389 mL) in a 500 mL 3-neck flask was added 2-tert-butyl aniline (4 0.6 mL). The reaction was cooled to −10° C. and $KNO_3$ in 3.89 g aliquots was added every 6 min for a total of 10 aliquots. Tried to maintain temperature at −5° C. to −10° C. After final addition of $KNO_3$, stirred the reaction for five min then it was poured onto ice (50 g). The black mix was diluted with $H_2O$ and extracted with EtOAc. The aqueous layer was basified with solid NaOH slowly then extracted with EtOAc (2×). The combined organic layers were washed with 6N NaOH and then with a mix of 6 N NaOH and brine, dried over $Na_2SO_4$, filtered and concentrated in vacuo to obtain crude 2-tert-butyl-5-nitro-aniline as a dark red-black oil which solidified when standing at RT. The crude material was triturated with about 130 mL hexanes. After decanting the hexanes, the material was dried to obtain a dark red-black solid.

Preparation XIX—2-tert-Butyl-5-nitrophenol

In a 250 mL round bottom flask, 20 mL concentrated $H_2SO_4$ was added to 2-tert-butyl-5-nitro-aniline (7.15 g) by adding 5 mL aliquots of acid and sonicating with occasional heating until all of the starting aniline went into solution. $H_2O$ (84 mL) was added with stirring, then the reaction was cooled to 0° C. forming a yellow-orange suspension. A solution of $NaNO_2$ (2.792 g) in $H_2O$ (11.2 mL) was added dropwise to the suspension and stirred for 5 min. Excess $NaNO_2$ was neutralized with urea, then the cloudy solution was transferred to 500 mL 3-necked round bottom flask then added 17 mL of 1:2$H_2SO_4$:$H_2O$ solution, and heated at reflux. Two additional 5 mL aliquots of 1:2$H_2SO_4$:$H_2O$ solution, a 7 mL aliquot of 1:2$H_2SO_4$:$H_2O$ solution and another 10 mL of 1:2$H_2SO_4$: $H_2O$ were added while heating at reflux. The mixture was cooled to RT forming a black layer floating on top of the aqueous layer. The black layer was diluted with EtOAc (300 mL) and separated. The organic layer was washed with $H_2O$ then brine, dried over $Na_2SO_4$ and concentrated in vacuo. Crude oil was purified on silica gel column with 8% EtOAc/Hexanes. Upon drying under vacuum, the 2-tert-butyl-5-nitrophenol was isolated as a brown solid.

Preparation XX—1-methylpiperidine-4-carboxylic acid ethyl ester

Piperidine-4-carboxylic acid ethyl ester (78 g) was dissolved in MeOH (1.2 L) at RT then formaldehyde (37%, 90 mL) and acetic acid (42 mL) were added and stirred for 2 h. The mixture was cooled to 0° C., $NaCNBH_3$ (70 g) was added, and the mix was stirred for 20 min at 0° C., then overnight at RT. The mixture was cooled to 0° C. then quenched with 6N NaOH. The mixture was concentrated in vacuo to an aqueous layer, which was extracted with EtOAc (4×), brine-washed, dried over $Na_2SO_4$, and concentrated in vacuo to provide 1-methylpiperidine-4-carboxylic acid ethyl ester.

a) (1-Methyl-piperidin-4-yl)-methanol. (M+H 130.2. Calc'd 129.1) was prepared similarly to that outlined above.

Preparation XXI—1-[2-(2-tert-Butyl-5-nitro-phenoxy)-ethyl]-piperidine

To 2-tert-butyl-5-nitrophenol (1.01 g) and $K_2CO_3$ (1.72 g) was added acetone (35 mL) and $H_2O$ (10.5 mL), then 1-(2-chloroethyl)piperidine HCl (1.909 g) and TBAI (153 mg). The mixture was stirred at reflux overnight. Additional $K_2CO_3$ (850 mg) and 1-(2-chloroethyl)-piperidine HCl (950 mg) were added and the mixture was heated at reflux for 6 h. The mixture was concentrated in vacuo to an aqueous layer which was acidified with 2 N HCl and extracted with EtOAc. The aqueous layer was basified with 6 N NaOH and washed with $CH_2Cl_2$ (3×). The combined organic layers were washed with brine/1 N NaOH and dried over $Na_2SO_4$. Washed the EtOAc layer with 2 N NaOH/brine and dried over $Na_2SO_4$. The crude material was purified by silica gel column chromatography with 15% EtOAc/Hexanes to yield 1-[2-(2-tert-butyl-5-nitro-phenoxy)-ethyl]-piperidine as a light tan solid.

(M+1)=307.3.

Preparation XXII—1-Boc-Piperidine-4-carboxylic acid ethyl ester

To a stirred solution of piperidine-4-carboxylic acid ethyl ester (23.5 g) in EtOAc (118 mL) at 0° C. was added dropwise $Boc_2O$ in EtOAc (60 mL). The reaction was warmed to RT and stirred overnight. Washed reaction with $H_2O$, 0.1 N HCl, $H_2O$, $NaHCO_3$ and brine. The organic layer was dried over $Na_2SO_4$, filtered and concentrated in vacuo.

The liquid was dried under vacuum to provide 1-Boc-piperidine-4-carboxylic acid ethyl ester.

The following compounds were prepared similarly to the procedure outlined above:
a) N-Boc-(2-chloropyrimidin-4-yl)-methylamine.
b) 1-(2-tert-Butyl-4-nitrophenyl)-4-Boc-piperazine.
c) 1-Boc-azetidine-3-carboxylic acid
d) 1-Boc-4-Hydroxymethyl-piperidine using TEA.

Preparation XXIII—1-Boc-4-hydroxymethyl-piperidine

1-Boc-4-Hydroxymethyl-piperidine was prepared from 1-Boc-piperidine-4-carboxylic acid ethyl ester by a procedure similar to that described in the preparation of 2-morpholin-4-yl-propanol.

Preparation XXIV—1-Boc-4-Methylsulfonyloxymethyl-piperidine

Dissolved 1-Boc-4-hydroxymethyl-piperidine in anhydrous $CH_2Cl_2$ (50 mL) and TEA (4.5 mL) and cooled to 0° C. Mesyl chloride (840 µL) was added and the mixture was stirred for 15 min then at RT for 45 min. The mixture was washed with brine/1 N HCl and then brine, dried over $Na_2SO_4$, concentrated in vacuo and dried under high vacuum to provide 1-Boc-4-methylsulfonyloxymethyl-piperidine as a yellow orange thick oil.

a) 1-Boc-3-methylsulfonyloxymethyl-azetidine was prepared similarly to the procedure outlined above.

Preparation XXV—1-Boc-4-(3-nitro-6-pentafluoroethyl-phenoxymethyl)-piperidine

To a slurry of 60% NaH suspension in DMF (30 mL) at RT added a solution of 5-nitro-2-pentafluoroethyl-phenol (3.6 g) in 5 mL DMF. The dark red mixture was stirred at RT for 10 min then added a solution of 1-Boc-4-methylsulfonyloxymethyl-piperidine (3.1 g) in 5 mL DMF. The reaction was stirred at 60° C. and 95° C. After 1 h, added 2.94 g $K_2CO_3$ and stirred overnight at 105° C. After cooling to RT, the reaction was diluted with hexanes and 1N NaOH. Separated layers, and washed organic layer with 1 N NaOH and with brine, dried over $Na_2SO_4$, filtered and concentrated in vacuo. Purification with silica gel column chromatography with 8% EtOAc/Hexanes yielded 1-Boc-4-(3-nitro-6-pentafluoroethyl-phenoxymethyl)-piperidine as a light yellow thick oil.

Preparation XXVI—4-(3-nitro-6-pentafluoroethyl-phenoxymethyl)-piperidine 4-(3-Nitro-6-pentafluoroethyl-phenoxymethyl)-piperidine was prepared from 1-Boc-4-(3-nitro-6-pentafluoroethyl-phenoxymethyl)-piperidine by a procedure similar to that described in the preparation of 2-(3-nitro-5-trifluoromethyl-phenoxymethyl)-pyrrolidine.

Preparation XXVII—1-methyl-4-(3-nitro-6-pentafluoroethyl-phenoxymethyl)-piperidine 4-(3-Nitro-6-pentafluoroethyl-phenoxymethyl)-piperidine (316.5 mg) was dissolved in 2.7 mL acetonitrile, then added 37% formaldehyde/$H_2O$ (360 µL) and then $NaBH_3CN$ (90 mg). Upon addition of $NaCNBH_3$ the reaction exothermed slightly. The reaction was stirred at RT and pH was maintained at ~7 by addition of drops of glacial acetic acid. After about 1 h, the mixture was concentrated in vacuo, treated with 8 mL 2 N KOH and extracted (2×) with 10 mL $Et_2O$. The organic layers were washed with 0.5 N KOH and then the combined organic layers were extracted (2×) with 1 N HCl. The aqueous layer was basified with solid KOH and extracted two times with $Et_2O$. This organic layer was then washed with brine/1 N NaOH, dried over $Na_2SO_4$, filtered, concentrated in vacuo and dried under high vacuum to give pure compound.

Preparation XXVIII—1-Isopropyl-4-(5-nitro-2-pentafluoroethyl-phenoxymethyl)-piperidine Dissolved 4-(5-nitro-2-pentafluoroethyl-phenoxymethyl)-piperidine (646 mg) in DCE(6.4 mL), then added acetone (136 µl), $NaBH(OAc)_3$ (541 mg) and finally acetic acid (105 µL). Stirred the cloudy yellow solution under $N_2$ at RT overnight. Added another 130 µL acetone and stirred at RT over weekend. Quenched the reaction with 30 mL N NaOH/$H_2O$ and stirred 10 min. Extracted with $Et_2O$ and the organic layer was brine-washed, dried over $Na_2SO_4$, filtered and concentrated in vacuo. Dried under high vacuum for several h to obtain 1-isopropyl-4-(5-nitro-2-pentafluoroethyl-phenoxymethyl)-piperidine as a yellow orange solid.

The following compounds were prepared similarly to the procedure outlined above:
a) 3,3-Dimethyl-1-(1-methyl-piperidin-4-yl)-6-nitro-2,3-dihydro-1H-indole was prepared using 1-methyl-piperidin-4-one. M+H 290; Calc'd 289.4.
b) 3,3-Dimethyl-1-(1-Boc-piperidin-4-ylmethyl)-6-nitro-2,3-dihydro-1H-indole using 1-Boc-4-formyl-piperidine.

Preparation XXIX—3,3-Dimethyl-1-(1-methyl-piperidin-4-ylmethyl)-6-nitro-2,3-dihydro-1H-indole 3,3-Dimethyl-1-piperidin-4-ylmethyl-6-nitro-2,3-dihydro-1H-indole was treated with an excess of formaldehyde and $NaBH(OAc)_3$ and stirred overnight at RT. The reaction was quenched with MeOH and concentrated in vacuo. The residue was partitioned between EtOAc and 1 N NaOH. The organic layer was removed, washed with brine, dried ($Na_2SO_4$), filtered and concentrated to provide the compound.

Preparation XXX—(S) 2-(5-Nitro-2-pentafluoroethyl-phenoxymethyl)-oxirane

Combined 5-nitro-2-pentafluoromethylphenol (2.69 g), DMF (25 mL) $K_2CO_3$ (3.03 g) and (S) toluene-4-sulfonic acid oxiranyl-methyl ester (2.27 g) and stirred the mixture at 90° C. After about 4 h, the mix was cooled, diluted with EtOAc, washed with $H_2O$, 1 N NaOH (2×), 1 N HCl and then with brine. Dried over $Na_2SO_4$, filtered and concentrated in vacuo. Purified the crude on silica gel column with 5% EtOAc/hexane and drying under high vacuum provided the (S)-2-(5-nitro-2-pentafluoroethyl-phenoxymethyl)-oxirane.

a) (R)-2-(5-Nitro-2-pentafluoroethyl-phenoxymethyl)-oxirane was prepared similar to the procedure outlined above.

Preparation XXXI—5-nitro-2-trifluoromethylanisole

Cooled 140 mL pyridine in a large sealable vessel to −40° C. Bubbled in trifluoromethyl iodide from a gas cylinder which had been kept in freezer overnight. After adding $ICF_3$ for 20 min, added 2-iodo-5-nitroanisole (24.63 g) and copper powder (67.25 g). Sealed vessel and stirred vigorously for 22 h at 140° C. After cooling to −50° C., carefully unsealed reaction vessel and poured onto ice and Et$_2$O. Repeatedly washed with Et$_2$O and H$_2$O. Allowed the ice—Et$_2$O mixture to warm to RT. Separated layers, washed organic layer with 1 N HCl (3×), then brine, dried over Na$_2$SO$_4$, filtered and concentrated in vacuo. Eluted material through silica gel plug (4.5:1 Hex:CH$_2$Cl$_2$) to provide 5-nitro-2-trifluoromethylanisole.

Preparation XXXII—1-[2-(5-nitro-2-trifluoromethylphenoxy)ethyl]pyrrolidine

1-[2-(5-Nitro-2-trifluoromethylphenoxy)ethyl]-pyrrolidine was prepared from 5-nitro-2-trifluoromethyl-phenol and 1-(2-chloroethyl)pyrrolidine by a procedure similar to that described for 1-[2-(2-tert-butyl-5-nitro-phenoxy)-ethyl]-piperidine.

Preparation XXXIII—1-[2-(5-Nitro-2-pentafluoroethyl-phenoxy)-ethyl]-piperidine

1-[2-(5-Nitro-2-pentafluoroethyl-phenoxy)-ethyl]-piperidine was prepared from 5-nitro-2-pentafluoroethylphenol and 1-(2-chloroethyl)piperidine by a procedure similar to that described in the preparation of 1-[2-(2-tert-butyl-5-nitro-phenoxy)-ethyl]-piperidine.

Preparation XXXIV—3-(1-Boc-pyrrolidin-2-ylmethoxy)-4-pentafluoroethyl-phenylamine 3-(2-Pyrrolidin-1-yl-methoxy)-4-trifluoromethyl-phenylamine was prepared from 1-[2-(5-nitro-2-trifluoromethylphenoxy)methyl]-pyrrolidine by a procedure similar to that described in the preparation of 1-Boc-4-(3-amino-5-trifluoromethyl-phenoxy)-piperidine.

Preparation XXXV—(R) Acetic acid 2-(5-nitro-2-pentafluoroethyl-phenoxy)-1-pyrrolidin-1-ylmethylethyl ester Dissolved 1-(5-nitro-2-pentafluoroethyl-phenoxy)-3-pyrrolidin-1-yl-propan-2-ol (3.5 g) in CH$_2$Cl$_2$ (15 mL), added TEA (2.55 mL) and cooled to 0° C. Acetyl chloride (781.3 μL) was added dropwise, forming a suspension. The mixture was warmed to RT and stirred for 1.5 h. Additional acetyl chloride (200 μL) was added and the mix was stirred for another h. The mixture was diluted with CH$_2$Cl$_2$ and washed with sat. NaHCO$_3$. The organic layer was removed, washed with brine and back extracted with CH$_2$Cl$_2$. Dried the combined organic layers over Na$_2$SO$_4$, filtered and concentrated in vacuo. The residue was purified over silica gel column (5:94.5:0.5 MeOH:CH$_2$Cl$_2$:NH$_4$OH) to provide the titled compound as a yellow brown oil.

The following compounds were prepared similarly to the procedure outlined above:
a) (R) Acetic acid 2-(5-amino-2-pentafluoroethyl-phenoxy)-1-pyrrolidin-1-yl-methyl-ethyl ester.
b) 1-(2,2-Dimethyl-6-nitro-2,3-dihydro-benzo[1,4]oxazin-4-yl)-ethanone. M-NO$_2$ 206.4; Calc'd 250.1.

Preparation XXXVI—2-Dimethylamino-1-(3,3-dimethyl-6-nitro-2,3-dihydro-indol-1-yl)-ethanone 3,3-Dimethyl-6-nitro-2,3-dihydro-1H-indole (5 g) was dissolved in DMF (100 mL) and HOAt (3.89 g) dimethylamino-acetic acid (5.83 g) and EDC (3.89 g) were added. The reaction was stirred overnight. The mixture was diluted with CH$_2$Cl$_2$ (1 L) and washed with sat'd NaHCO$_3$ (3×200 mL). The organic layer was washed with brine, dried over Na$_2$SO$_4$, filtered and concentrated in vacuo. The residue was purified by flash chromatography (SiO$_2$, EtOAc to 5% MeOH/EtOAc) to afford the title compound.

a) 1-(3,3-Dimethyl-6-nitro-2,3-dihydro-indol-1-yl)-2-(N-Boc-amino)-ethanone was prepared similar to that outlined above.

Preparation XXXVII—1-(6-Amino-3,3-dimethyl-2,3-dihydro-indol-1-yl)-2-(N-Boc-amino)-ethanone 1-(3,3-dimethyl-6-nitro-2,3-dihydro-indol-1-yl)-2-(N-Boc-amino)-ethanone (3.9 g) was dissolved in EtOH (30 mL) and Fe powder (3.1 g) NH$_4$Cl (299 mg) and H$_2$O (5 mL) were added. The reaction was stirred at 80° C. overnight. The reaction was filtered through Celite® and evaporated off the MeOH. The residue was partitioned between CH$_2$Cl$_2$ and sat'd NaHCO$_3$. The organic layer was removed, washed with brine, dried over Na$_2$SO$_4$, filtered and concentrated in vacuo. The residue was purified by flash chromatography (SiO$_2$, 25% EtOAc/hexane). The purified fractions were concentrated in vacuo to afford the compound as a white powder.

The following compounds were prepared similarly to the procedure outlined above:
a) 1-(6-Amino-3,3-dimethyl-2,3-dihydro-indol-1-yl)-2-dimethylamino-ethanone.
b) 3,3-Dimethyl-1-(1-methyl-piperidin-4-ylmethyl)-2,3-dihydro-1H-indol-6-ylamine.
c) 3-(4-Methyl-piperazin-1-ylmethyl)-4-pentafluoroethyl-phenylamine. M+H 324.2. Calc'd 323.
d) 3,3-Dimethyl-1-(1-methyl-piperidin-4-yl)-2,3-dihydro-1H-indol-6-ylamine. M+H 259.6; Calc'd 259.3.
e) 3,3-Dimethyl-1,1-dioxo-2,3-dihydro-1H-116-benzo[d]isothiazol-6-ylamine
f) 1,1,4,4-Tetramethyl-1,2,3,4-tetrahydro-naphth-6-ylamine.
g) 3,3-Dimethyl-1-(1-Boc-piperidin-4-ylmethyl)-2,3-dihydro-1H-indol-6-ylamine.

Preparation XXXVIII—2-Boc-4,4-dimethyl-7-nitro-1,2,3,4-tetrahydro-isoquinoline 4,4-dimethyl-7-nitro-1,2,3,4-tetrahydro-isoquinoline (150 mg) was dissolved with CH$_2$Cl$_2$ (3 mL) DIEA (100 μL) DMAP (208 mg and Boc$_2$O (204 mg) and the mixture was stirred for 6 h at RT. The reaction was diluted with CH$_2$Cl$_2$, washed with sat'd NaHCO$_3$ and dried over MgSO$_4$, filtered and concentrated to provide the compound which was used without further purification.

a) 1-(4,4-Dimethyl-7-nitro-3,4-dihydro-1H-isoquinolin-2-yl)-ethanone. (M+H 249.3) was prepared similarly to the procedure outlined above substituting Ac$_2$O.

Preparation XXXIX—2-Bromo-N-(4-methoxy-benzyl)-5-nitro-benzamide

PMB-amine (5.35 mL) in CH$_2$Cl$_2$ (130 mL) was slowly added to 2-bromo-5-nitro-benzoyl chloride (10.55 g) and NaHCO$_3$ (9.6 g) and the mixture was stirred at RT for 1 h. The mixture was diluted with CH$_2$Cl$_2$ (1 L), filtered, washed with dilute HCl, dried, filtered again, concentrated and dried under vacuum to provide the compound as a white solid. M+H 367. Calc'd 366.

Preparation XL—2-Bromo-N-(4-methoxy-benzyl)-N-(2-methyl-allyl)-5-nitro-benzamide To a suspension of NaH (1.22 g) in DMF (130 mL) was added 2-bromo-N-(4-methoxy-benzyl)-5-nitro-benzamide (6.2 g) in DMF (60 mL) at −78° C. The mixture was warmed to 0° C., 3-bromo-2-methyl-propene (4.57 g) was added and the mixture was stirred for 2 h at 0° C. The reaction was poured into ice water, extracted with EtOAc (2×400 mL), dried over $MgSO_4$, filtered and concentrated to a DMF solution which was used without further purification.

Preparation XLI—of 2-(4-Methoxy-benzyl)-4,4-dimethyl-7-nitro-3,4-dihydro-2H-isoquinolin-1-one 2-Bromo-N-(4-methoxy-benzyl)-N-(2-methyl-allyl)-5-nitro-benzamide (23.4 mmol) was dissolved in DMF (150 mL) and $Et_4NCl$ (4.25 g), $HCO_2Na$ (1.75 g) and NaOAc (4.99 g) were added. $N_2$ was bubbled through the solution for 10 min, then $Pd(OAc)_2$ (490 mg) was added and the mixture was stirred overnight at 70° C. The mixture was extracted with EtOAc, washed with sat'd $NH_4Cl$, dried over $MgSO_4$, filtered and concentrated until the compound precipitated as a white solid.

The following compounds were prepared similarly to the procedure outlined above:

a) 3,3-Dimethyl-6-nitro-2,3-dihydro-benzofuran was prepared from 1-bromo-2-(2-methyl-allyloxy)-4-nitro-benzene.

b) 3,9,9-Trimethyl-6-nitro-4,9-dihydro-3H-3-aza-fluorene was prepared from 4-[1-(2-bromo-4-nitro-phenyl)-1-methyl-ethyl]-1-methyl-1,2,3,6-tetrahydro-pyridine.

Preparation XLII—4,4-Dimethyl-7-nitro-3,4-dihydro-2H-isoquinolin-1-one 2-(4-Methoxy-benzyl)-4,4-dimethyl-7-nitro-3,4-dihydro-2H-isoquinolin-1-one (2.0 g) was dissolved in $CH_3CN$ (100 mL) and $H_2O$ (50 mL) and cooled to 0° C. CAN (9.64 g) was added and the reaction was stirred at 0° C. for 30 min, then warmed to RT and stirred for 6 h. The mixture was extracted with $CH_2Cl_2$ (2×300 mL) washed with sat'd $NH_4Cl$, dried over $MgSO_4$, filtered and concentrated. The crude material was recrystallized in $CH_2Cl_2$/EtOAc (1:1) to give 4,4-dimethyl-7-nitro-3,4-dihydro-2H-isoquinolin-1-one as a white solid.

Preparation XLIII—4,4-Dimethyl-7-nitro-1,2,3,4-tetrahydro-isoquinoline 4,4-Dimethyl-7-nitro-3,4-dihydro-2H-isoquinolin-1-one (230 mg) was dissolved in THF (10 mL) and $BH_3Me_2S$ (400 µl) was added and the reaction was stirred overnight at RT. The reaction was quenched with MeOH (10 mL) and NaOH (200 mg) and heating at reflux for 20 min. The mixture was extracted with EtOAc, washed with sat'd $NH_4Cl$, extracted with 10% HCl (20 mL). The acidic solution was treated with 5 N NaOH (15 mL), extracted with EtOAc (30 mL) dried, filtered and evaporated to give the compound as a yellow solid. M+H 207.2, Calc'd 206.

a) 4-Boc-2,2-dimethyl-6-nitro-3,4-dihydro-2H-benzo[1,4]oxazine was prepared similarly to that outlined above.

Preparation XLIV—2-Bromomethyl-4-nitro-1-pentafluoroethyl-benzene

2-Methyl-4-nitro-1-pentafluoroethyl-benzene (2.55 g) was dissolved in $CCl_4$ (30 mL) and AIBN (164 mg) and NBS (1.96 g) were added. The reaction was heated to reflux and stirred for 24 h. The mix was diluted with $CH_2Cl_2$, washed with sat'd $NaHCO_3$, dried over $MgSO_4$ and concentrated to give the compound as an oil which was used without further purification.

Preparation XLV—1-Methyl-4-(5-nitro-2-pentafluoroethyl-benzyl)-piperazine

2-Bromomethyl-4-nitro-1-pentafluoroethyl-benzene (2.6 g) was added to N-methylpiperazine (5 mL) and stirred at RT for 3 h. The mixture was filtered and the filtrate was treated with 1-chlorobutane, extracted with 2 N HCl (100 mL). The acidic solution was treated with 5 N NaOH (6 mL) then extracted with EtOAc. The organic layer was removed, dried over $MgSO_4$ and concentrated to give the compound as an oil.

a) 4-(5-Nitro-2-pentafluoroethyl-benzyl)-morpholine was prepared similarly to the procedure outlined above.

Preparation XLVI—1-Boc-4-(5-nitro-2-pentafluoroethyl-benzyl)-piperazine.

2-Bromomethyl-4-nitro-1-pentafluoroethyl-benzene (2.5 g) was dissolved in $CH_2Cl_2$ and added to N-Boc-piperazine (2.5 g) and $NaHCO_3$ (1 g) and stirred at RT overnight. The mixture was diluted with $CH_2Cl_2$ (100 mL), washed with sat'd $NH_4Cl$, dried over $MgSO_4$, filtered and concentrated. The residue was purified by silica gel chromatography (hexane, $CH_2Cl_2$:hexane 2:8) to give the compound as an yellow solid.

Preparation XLVII—(4-Boc-piperazin-1-yl)-(3-nitro-5-trifluoromethyl-phenyl)-methanone A mixture of 3-nitro-5-trifluoromethyl-benzoic acid (4.13 g), 4-Boc-piperazine (2.97 g), EDC (3.88 g), HOBt (2.74 g), DIEA (3.33 mL) in $CH_2Cl_2$ (120 mL) was stirred at RT for 3 h. The mixture was diluted with $CH_2Cl_2$ (100 mL), washed with sat'd $NH_4Cl$, dried over $MgSO_4$, filtered and concentrated. The residue was purified by silica gel chromatography (hexane, $CH_2Cl_2$:hexane 1:2) to give the compound as a white solid.

Preparation XLVIII—1-Boc-4-(3-nitro-5-trifluoromethyl-benzyl)-piperazine (4-Boc-piperazin-1-yl)-(3-nitro-5-trifluoromethyl-phenyl)-methanone (403 mg) was dissolved in THF (6 mL) and $BH_3Me_2S$ (300 µL) was added and the reaction was stirred for 3 h at 60° C. and 2 h at RT. The reaction was quenched with MeOH (5 mL) and NaOH (100 mg) and stirred at RT for 1 h. The mixture was concentrated and dissolved in $CH_2Cl_2$, washed with sat'd $NH_4Cl/NaHCO_3$, dried ($MgSO_4$), filtered and evaporated to give the compound as an oil. M+H 390.3.

Preparation XLIX—2-Ethyl-4-aminomethyl pyridine

To a solution of 2-ethyl-4-thiopyridylamide (10 g) in MeOH (250 mL) was added Raney 2800 Nickel (5 g, Aldrich) in one portion. The mixture was stirred at RT for 2 days then at 60° C. for 16 h. The mixture was filtered, concentrated to provide the desired compound.

Preparation L—N-Boc-[2-(4-morpholin-4-yl-butyl)-pyrimidin-4-ylmethyl]-amine

N-Boc-(2-chloropyrimidine)-methylamine (663 mg) and 4-(aminopropyl)morpholine (786 mg) were dissolved in MeOH and concentrated in vacuo. The residue was heated at 100° C. for 15 min, forming a solid which was dissolved in $CH_2Cl_2$/MeOH then concentrated again and heated 15 min more. Concentrated in vacuo and dried under high vacuum. Triturated with a small amount of IpOH and allowed to settle over a weekend. Filtered, rinsing with a small amount of IpOH to provide the compound as a white solid.

a) (4-Bocaminomethyl-pyrimidin-2-yl)-[2-(1-methyl-pyrrolidin-2-yl)-ethyl]-amine. (M+H 336.5; Calc'd 335.45) was prepared similarly to the procedure outlined above.

Preparation LI—4-cyano-2-methoxypyridine

Under a stream of $N_2$ and with cooling, Na metal (2.7 g) was added to MeOH (36 mL) with a considerable exotherm. After the Na is dissolved, a solution of 2-chloro-4-cyanopyridine (15 g) in dioxane:MeOH (1:1, 110 mL) was added via dropping funnel over a 10 min period. The reaction was heated to reflux for 3.5 h then cooled at ~10° C. overnight. Solid was filtered off and the solid was washed with MeOH. The filtrate was concentrated to ~60 mL and $H_2O$ (60 mL) was added to redissolve a precipitate. Upon further concentration, a precipitate formed which was washed with $H_2O$. Further concentration produced additional solids. The solids were combined and dried in vacuo overnight at 35° C. to provide 4-cyano-2-methoxypyridine which was used as is.

Preparation LII—(2-methoxypyridin-4-yl)methylamine

4-Cyano-2-methoxypyridine (1.7 g) was dissolved in MeOH (50 mL) and conc. HCl (4.96 mL) was added. Pd/C (10%) was added and $H_2$ was added and let stand overnight. The solids were filtered through Celite® and the cake was washed with MeOH (~250 mL). Concentration in vacuo produced an oil which was dissolved in MeOH (~20 mL). $Et_2O$ (200 mL) was added and stirred for 1 h. The resulting precipitate was filtered and washed with $Et_2O$ to afford (2-methoxypyridin-4-yl)methylamine (hydrochloride salt) as an off-white solid.

Preparation LIII—2-(4-Amino-phenyl)-2-methyl-propionic acid methyl ester

2-Methyl-2-(4-nitro-phenyl)-propionic acid methyl ester (2.1 g) was dissolved in THF (70 mL) and acetic acid (5 mL) and Zn (10 g) were added. The mixture was stirred for 1 h and filtered through Celite®. The filtrate was rinsed with EtOAc and the organics were evaporated to a residue which was purified on silica gel chromatography (40% EtOAc/hexanes) to provide the desired compound as a yellow oil. M+H 194.

Preparation LIV—1-(2-tert-Butyl-phenyl)-4-methyl-piperazine 2-tert-Butyl-phenylamine and bis-(2-chloro-ethyl)-methylamine were mixed together with $K_2CO_3$ (25 g), NaI (10 g) and diglyme (250 mL) and heated at 170° C. for 8 h. Cooled and filtered solid and evaporated solvent. Diluted with EtOAc, washed with $NaHCO_3$ solution, extracted twice more with EtOAc, washed with brine, dried over $Na_2SO_4$ and evaporated to give the compound as a dark solid.

a) 1-Bromo-2-(2-methyl-allyloxy)-4-nitro-benzene was prepared from methallyl bromide was prepared similarly to the procedure outlined above.

Preparation LV 3-(1-Methyl-1,2,3,6-tetrahydro-pyridin-4-yl)-5-trifluoromethyl-phenylamine 3-(5,5-dimethyl-[1,3,2]dioxaborinan-2-yl)-5-trifluoromethyl-phenylamine (8.8 g, 0.032 mmol) was added to trifluoro-methanesulfonic acid 1-methyl-1,2,3,6-tetrahydro-pyridin-4-yl ester (7.91 g, 0.032 mmol) and 2 N $Na_2CO_3$ aqueous solution (25 mL) was bubbled through $N_2$ for 5 min. $Pd(PPh_3)_4$ (3.7 g, 3.2 mmol) was added and the reaction was heated to 80° C. for 16 h. The reaction was cooled to RT and diluted with $Et_2O$ (100 mL). The mixture was filtered through Celite® and the filtrate was washed with $NaHCO_3$ aqueous solution (25 mL) followed by brine (25 mL). The organic phase was dried over $Na_2SO_4$ and concentrated in vacuo. The desired product was isolated by passing through silica gel column chromatography (EtOAc, then (2 M $NH_3$) in MeOH/EtOAc) to provide a yellow oil.

Preparation LVI—3,3-Dimethyl-6-nitro-2,3-dihydro-benzo[d]isothiazole 1,1-dioxide 3,3-dimethyl-2,3-dihydro-benzo[d]isothiazole 1,1-dioxide was added to $KNO_3$ in $H_2SO_4$ cooled to 0° C. and stirred for 15 min. The reaction was warmed to RT and stirred overnight. The mix was poured into ice and extracted with EtOAc (3×), washed with $H_2O$ and brine, dried and evaporated to give the product which was used without further purification.

a) 1,1,4,4-Tetramethyl-6-nitro-1,2,3,4-tetrahydro-naphthalene was prepared similarly to the procedure outlined above.

Preparation LVII—3-(1-Methyl-1,2,3,4-tetrahydro-pyridin-4-yl)-5-trifluoromethyl-phenylamine 3-(5,5-Dimethyl-[1,3,2]dioxaborinan-2-yl)-5-trifluoromethyl-phenylamine (1.2 g) was added to trifluoro-methanesulfonic acid 1-methyl-1,2,3,6-tetrahydro-pyridin-4-yl ester (1.0 g), LiCl (500 mg, Aldrich), $PPh_3$ (300 mg, Aldrich) and 2M $Na_2CO_3$ aqueous solution (6 mL) and was bubbled with $N_2$ for 5 min. $Pd(PPh_3)_4$ (300 mg, Aldrich) was added and the reaction was heated to 80° C. for 16 h. The reaction was cooled to RT and diluted with $Et_2O$ (100 mL). The mixture was filtered through Celite® and the filtrate was washed with $NaHCO_3$ aqueous solution (25 mL) followed by brine (25 mL). The organic phase was dried over $Na_2SO_4$ and concentrated in vacuo. The desired compound was isolated by silica gel column chromatography (EtOAc 10% (2 M $NH_3$) in MeOH/EtOAc) to provide yellow oil. M+H 257.2; Calc'd 256.1.

Preparation LVIII—Trifluoromethylsulfonic acid 1-methyl-1,2,3,6-tetrahydro-pyridin-4-yl ester In a three-necked round bottom flask equipped with a thermometer and an additional funnel was placed anhydrous THF (200 mL) and 2 M LDA (82.8 mL). The solution was cooled to −78° C. and a solution of 1-methyl-piperidin-4-one (20 mL) in anhydrous THF (70 mL) was added dropwise. The reaction was warmed to −10° C. over 30 min and cooled down again to −78° C. $Tf_2NPh$ (54.32 g) in 200 mL of anhydrous THF was added through the additional funnel over 30 min and anhydrous THF (30 mL) was added to rinse the funnel. The reaction was warmed to RT and the reaction solution was concentrated in vacuo. The residue was dissolved in $Et_2O$ purified on neutral $Al_2O_3$ column chromatography ($Et_2O$ as elutant). The product was obtained as orange oil.

Preparation LIX—3-(5,5-Dimethyl-[1,3,2]dioxaborinan-2-yl)-5-trifluoromethyl-phenylamine $N_2$ was bubbled through a solution of 3-bromo-5-trifluoromethyl-phenylamine (2.38 g), 5,5,5',5'-tetramethyl-[2,2'] bi[[1,3,2]dioxaborinanyl] (2.24 g, Frontier Scientific) and KOAc (2.92 g), dppf (165 mg, Aldrich) in anhydrous dioxane (50 mL) for 2 min. $PdCl_2$ (dppf) (243 mg, Aldrich) was added and the reaction was heated to 80° C. for 4 h. After cooling to RT, the mix was diluted with 50 mL of $Et_2O$, filtered through Celite®, and the filtrate was concentrated in vacuo. The residue was dissolved in $Et_2O$ (100 mL), washed with sat. $NaHCO_3$ aqueous solution (50 mL) followed by brine (50 mL). The organic phase was dried over $Na_2SO_4$ and concentrated in vacuo. The residue was dissolved in 3:2 $Et_2O$/Hex (100 mL), filtered through Celite® and the filtrate was concentrated in vacuo to afford a dark brown semi-solid.

Preparation LX—1-Boc-3-Hydroxymethyl-azetidine

A solution of 1-Boc-azetidine-3-carboxylic acid (1.6 g) and $Et_3N$ (2 mL) in anhydrous THF (60 mL) was cooled to 0° C. Isopropyl chloroformate (1.3 g) was added via a syringe slowly; forming a white precipitate almost immediately. The reaction was stirred for 1 h at 0° C. and the precipitate was filtered out. The filtrate was cooled to 0° C. again and aqueous $NaBH_4$ solution (900 mg, 5 mL) was added via pipette and stirred for 1 h. The reaction was quenched with $NaHCO_3$ solution (50 mL) and the product was extracted with EtOAc (200 mL). The organic phase was washed with brine (50 mL), dried over $Na_2SO_4$ and concentrated in vacuo. The residue was dissolved in EtOAc and passed through a short silica gel pad. Concentrating the filtrate in vacuo provided the compound as a light yellow oil.

Preparation LXI—1-Boc-3-(3-nitro-5-trifluoromethyl-phenoxymethyl)-azetidine

A mixture of 1-Boc-3-methylsulfonyloxymethyl-azetidine (1.47 g), 3-nitro-5-trifluoromethyl-phenol (1.15 g) and $K_2CO_3$ (1.15 g) in DMF (20 mL) at 80° C. was stirred overnight. The reaction was cooled to RT and diluted with 25 mL of sat. $NaHCO_3$ and 50 mL of EtOAc. The organic phase was separated and washed with brine (25 mL), dried over $Na_2SO_4$ and concentrated in vacuo. The crude compound was purified by column chromatography (50% EtOAc/hex).

Preparation LXII—2,2-Dimethyl-6-nitro-3,4-dihydro-2H-benzo[1,4]oxazine 2,2-Dimethyl-6-nitro-4H-benzo[1,4]oxazin-3-one was added to $BH_3$-THF complex (Aldrich) in THF with ice cooling. The mixture was heated to reflux for 2 h then carefully diluted with 12 mL of MeOH and heated to reflux for an additional 1 h. Concentrated HCl (12 mL) was added and heated to reflux for 1 h. The mixture was concentrated and the resulting solid was suspended in a dilute aqueous solution of NaOH (1 M) and extracted with EtOAc, (100 mL×4). The organic layers were washed with $H_2O$ and dried over $MgSO_4$. Evaporation of solvent gave a yellow solid.

Preparation LXIII—2,2,4-Trimethyl-6-nitro-4H-benzo[1,4]oxazin-3-one 2,2-Dimethyl-6-nitro-4H-benzo[1,4]oxazin-3-one (1.1 g) was mixed with MeI (850 mg, Aldrich), $K_2CO_3$ (1.38 g, Aldrich) and DMF (30 mL, Aldrich) at 40° C. for 48 h. The DMF was removed in vacuo and the residue was diluted with EtOAc (80 mL). The organic phase was washed with $H_2O$ (50 mL), aqueous $Na_2SO_3$ (50 mL) and brine (50 mL). The resulting solution was dried ($MgSO_4$) and concentrated to provide the compound which was used as is.

Preparation LXIV—2-Bromo-N-(2-hydroxy-5-nitro-phenyl)-2-methyl-propionamide

2-Amino-4-nitro-phenol (3.08 g, Aldrich) was stirred with THF (30 mL, Aldrich) in an ice bath. 2-Bromo-2-methyl-propionyl bromide (2.47 mL, Aldrich) and $Et_3N$ (2.0 g, Aldrich) was slowly added via syringe. The mixture was stirred for 45 min then poured into ice. The aqueous phase was extracted by EtOAc (50 mL×4). The organic layer was dried and concentrated. The desired product was crystallized from EtOAc. (*Chem. Pharm. Bull* 1996, 44(1): 103-114).

Preparation LXV—2,2-Dimethyl-6-nitro-4H-benzo[1,4]oxazin-3-one

2-Bromo-N-(2-hydroxy-5-nitro-phenyl)-2-methyl-propionamide was mixed with $K_2CO_3$ in 20 mL of DMF and stirred overnight at 50° C. The reaction mixture was poured into ice water. The precipitate was collected by filtration and washed with $H_2O$. The crude compound was recrystallized from EtOH.

Preparation LXVI—4-[1-(2-Bromo-4-nitro-phenyl)-1-methyl-ethyl]-1-methyl-pyridinium iodide 1-Methyl-4-[1-methyl-1-(4-nitro-phenyl)-ethyl]-pyridinium (8 g) was dissolved in glacial HOAc (10 mL) then diluted with $H_2SO_4$ (50 mL), then NBS (3.8 g) was added. After 1 h, additional NBS (1.2 g) was added, 30 min later another 0.5 g of NBS, then 15 min later 200 mg more NBS. After 1 h, the mixture was neutralized with $NH_4OH$ (conc.) with ice bath cooling. The neutralized mixture was then concentrated and used as is.

Preparation LXVII—4-[1-(2-Bromo-4-nitro-phenyl)-1-methyl-ethyl]-1-methyl-1,2,3,6-tetrahydropyridine 4-[1-(2-Bromo-4-nitro-phenyl)-1-methyl-ethyl]-1-methyl-pyridiniumiodide was mixed with MeOH (400 mL) and $CH_2Cl_2$ (200 mL), then treated with $NaBH_4$ (2.5 g) in portions. After stirring at RT for 2 h, the mixture was extracted with $CH_2Cl_2$ (300 mL×3). The $CH_2Cl_2$ layer was washed with brine, dried over $Na_2SO_4$ and concentrated in vacuo, to provide the desired product.

Preparation LXVIII—1-Methyl-4-[1-methyl-1-(4-nitro-phenyl)-ethyl]-pyridinium iodide 4-(4-Nitro-benzyl)-pyridine (4.3 g) was mixed with MeI (4 mL, 9.12 g)/NaOH (5 N, 30 mL), $Bu_4NI$ (150 mg) and $CH_2Cl_2$ (50 mL) and stirred at RT overnight. Additional MeI (2 mL) was added along with 50 mL of NaOH (5N). 6 h later, more MeI (2 mL) was added. The mixture was stirred at RT over the weekend. The mixture was cooled on ice bath and the base was neutralized by conc. HCl (aq) addition dropwise to pH 7. The compound was used as is.

Preparation LXIX—1-Methyl-4-(4-nitro-benzyl)-1,2,3,6-tetrahydro-pyridine 4-(4-Nitrobenzyl)pyridine (64 g) and TBAI (6 g) were dissolved in $CH_2Cl_2$ (500 mL) and the solution was suspended with NaOH (aq. 5 N, 450 mL) in a 3 L 3-necked round bottom flask. With vigorous stirring, iodomethane (213 g) was added and stirred vigorously at RT for 60 h (or until blue color disappears). The reaction was quenched with dimethylamine (100 mL) and MeOH (300 mL) and stirred for 2 h. $NaBH_4$ (19 g) was added to the mixture in small portions. The reaction mixture was stirred for 30 min at RT, then partitioned between $CH_2Cl_2/H_2O$ (500 mL/500 mL). The organic layer was collected and the aqueous layer was washed with $CH_2Cl_2$ (300 mL×3). The combined organic layers was washed with brine then concentrated in vacuo. The residue was purified on a silica wash-column (7% TEA in EtOAc). The desired fractions were combined and concentrated under vacuum to give the desired compound as a dark gray solid. (MS: M+1=261).

Preparation LXX—1-Boc-4-formyl-piperidine

4 Å Molecular sieves were heated to 100° C. and a vacuum was applied. They were cooled to RT and purged with $N_2$. $CH_2Cl_2$ (420 mL) and $CH_3CN$ (40 mL), NMO (40 g) and 1-Boc-4-hydroxymethylpiperidine (50 g) were added and the mix was stirred for 5 min then cooled to 15° C. TPAP (4.1 g) was added and an exotherm was observed. The reaction was maintained at RT with external cooling. The reaction was stirred at RT for 3 h, filtered, concentrated, diluted with 50% EtOAc/hexanes and purified on a silica gel plug (50% EtOAc/hexanes). The eluant fractions were concentrated to afford a yellow oil.

Preparation LXXI—2-Chloro-4-cyanopyridine

2-Chloro-4-cyanopyridine was prepared similar to the method described by Daves et al., J. Het. Chem., 1:130-132 (1964).

Preparation LXXII—4-(2-tert-Butyl-5-nitro-phenyl)-but-3-en-1-ol

A mix of 1-(tert-butyl)-2-bromo-4-nitrobenzene (3.652 g), TEA (5.92 mL), 3-buten-1-ol (5.48 mL), $Pd(OAc)_2$ (32 mg), $Pd(PPh_3)_4$ (327 mg) and toluene (40 mL) was degassed with nitrogen and heated in a sealed vessel for 16 h at 120° C. The next day, the reaction mixture was cooled to RT, filtered, and concentrated in vacuo. The crude was eluted on a silica gel column with 15% to 22% EtOAc/hexanes gradient system to yield a yellow-brown oil.

Preparation LXXIII—4-(2-tert-Butyl-5-nitro-phenyl)-but-3-enal 4-(2-tert-Butyl-5-nitro-phenyl)-but-3-en-1-ol (1.024 g) was dissolved in 10 mL of $CH_2Cl_2$ and added dropwise over 5 min to a −78° C. mix of oxalyl chloride (0.645 mL), DMSO (0.583 mL), and 10 mL $CH_2Cl_2$. The reaction was stirred at −78° C. for 1 h, then treated with a solution of TEA (1.52 mL) in 7 mL $CH_2Cl_2$ and stirred at −78° C. for an additional 25 min, then warmed to −30° C. for 35 min. The reaction was treated with 50 mL of saturated aqueous $NH_4Cl$, diluted with $H_2O$ and extracted with EtOAc. The organic layer was brine-washed, dried over $Na_2SO_4$, filtered, and concentrated in vacuo to yield a yellow oil which was used as is in Preparation LXXVI.

Preparation LXXIV—1-[4-(2-tert-Butyl-5-nitro-phenyl)-but-3-enyl]-pyrrolidine 4-(2-tert-Butyl-5-nitro-phenyl)-but-3-enal (895 mg) was dissolved in 40 mL THF, and to the solution was added pyrrolidine (0.317 mL). To the deep-orange solution was added $NaBH(OAc)_3$ (1.151 g) and glacial AcOH (0.207 mL). The reaction was stirred at RT overnight, then treated with saturated aqueous $NaHCO_3$ and diluted with $Et_2O$ and some 1 N NaOH. The layers were separated, and the organic layer was extracted with aqueous 2 N HCl. The acidic aqueous layer was basified to pH>12 with 6 N NaOH, extracted with $Et_2O$, brine-washed, dried over $Na_2SO_4$, filtered, and concentrated in vacuo to provide 1-[4-(2-tert-butyl-5-nitro-phenyl)-but-3-enyl]-pyrrolidine as a orange-brown oil.

Preparation LXXV—N-(2-bromo-5-nitrophenyl)acetamide

2-Bromo-5-nitroaniline (10 g) was dissolved in 500 mL of $CH_2Cl_2$, DIEA (6.6 g) was added to the mixture, followed by DMAP (100 mg). The mixture was cooled to 0° C. in ice bath. Acetyl chloride (4 g in 50 mL $CH_2Cl_2$) was added dropwise to the reaction mixture. After the mixture was stirred at RT over 3 h, extracted once with saturated $NaHCO_3$ solution and once with brine, the resulting organic layer was dried over $MgSO_4$, filtered and concentrated in vacuo. The crude material was purified by flash chromatography on silica gel with 1:1 EtOAc:Hexane to 100% EtOAc to afford N-(2-bromo-5-nitrophenyl)acetamide as a white solid. MS: 258 (M−1). Calc'd. for $C_8H_7BrN_2O_3$-259.06.

Preparation LXXVI—N-(2-bromo-5-nitrophenyl)-N-(2-methylprop-2-enyl)acetamide

A suspension of 2 g NaH (95% powder) in anhydrous DMF (100 mL) was cooled to −78° C., N-(2-bromo-5-nitrophenyl)acetamide (7 g) in dry DMF (50 mL) was added to the mixture under $N_2$ atmosphere. After the mixture was warmed to 0° C., 3-bromo-2-methylpropene (7.3 g in 20 dry DMF) was added to the mixture. The mixture was stirred at RT overnight. Next morning, the mixture was poured into a container of ice and extracted between saturated $NaHCO_3$ solution and EtOAc. The resulting organic layer was dried over $MgSO_4$, filtered and concentrated in vacuo. The crude material was purified by flash chromatography on silica gel with 7:2 hexane:EtOAc to afford the title compound as a yellow gum. MS: 314 (M+1). Calc'd. for $C_{12}H_{13}BrN_2O_3$-313.15.

Preparation LXXVII—1-(3,3-dimethyl-6-nitro-2,3-dihydro-indol-1-yl)ethanone

N-(2-Bromo-5-nitrophenyl)-N-(2-methylprop-2-enyl)acetamide (4.5 g) was dissolved in anhydrous DMF (50 mL), tetraethyl-ammonium chloride (2.5 g), sodium formate (1.2 g), NaOAc (3 g) were added, and the resulting mixture was bubbled with $N_2$ gas for 10 min. $Pd(OAc)_2$ (350 mg) was added and the mixture was heated at 80° C. under $N_2$ atmosphere overnight. After the mixture was concentrated in vacuo, it was partitioned between saturated $NaHCO_3$ solution and EtOAc, the resulting organic layer was dried over $MgSO_4$, filtered and concentrated in vacuo. The crude material was purified by flash chromatography on silica gel with 2:1 Hexane:EtOAc to afford the title compound as a yellow gum. MS: 235 (M+1). Calc'd. for $C_{12}H_{14}N_2O_3$-234.25.

Preparation LXXVIII—3,3-dimethyl-6-nitroindoline 1-(3,3-dimethyl-6-nitro-2,3-dihydro-indol-1-yl)ethanone (1.8 g) was dissolved in EtOH (50 mL), 12 N HCl (50 mL) was added and the resulting mixture was heated at 70° C. overnight. After the mixture was concentrated in vacuo, it was partitioned between saturated $NaHCO_3$ solution and EtOAc, the resulting organic layer was dried over $MgSO_4$, filtered and concentrated in vacuo to afford a yellow solid. MS: 193 (M+1). Calc'd. for $C_{10}H_{12}N_2O_2$-192.21.

Preparation LXXIX: 1-Acetyl-6-amino-3,3-dimethylindoline 1-(3,3-dimethyl-6-nitro-2,3-dihydro-indol-1-yl)ethanone (250 mg) was dissolved in MeOH (20 mL), the mixture was bubbled with $H_2$ for 10 min. 10% Pd/C (50 mg) was added and the mixture was stirred under $H_2$ overnight. The mixture was filtered through Celite® and concentrated in vacuo. The crude material was purified by flash chromatography on silica gel with 1:1 EtOAc:$CH_2Cl_2$ to afford the title compound as a white crystalline material. MS: 205 (M+1). Calc'd. for $C_{12}H_{16}N_2O$-204.27.

Preparation LXXX
N-Boc-(2-chloropyrimidin-4-yl)-methylamine

To 2-chloropyrimidine-4-carbonitrile [2.5 g, prepared by the procedure of Daves et. al. (J. Het. Chem., 1:130-132 (1964))] in EtOH (250 mL) under $N_2$ was added $Boc_2O$ (7.3 g). After the mixture was briefly placed under high vacuum and flushed with $N_2$, 10% Pd/C (219 mg) was added. $H_2$ was bubbled though the mixture (using balloon pressure with a needle outlet) as it stirred 4.2 h at RT. After filtration through Celite®, addition of 1.0 g additional $Boc_2O$, and concentration, the residue was purified by silica gel chromatography (5:1→4:1 hexanes/EtOAc) to obtain N-Boc-(2-chloropyrimidin-4-yl)-methylamine.

N-{4-[1-Methyl-1-(1-methyl-piperidin-4-yl)-ethyl]-phenyl}-2-[(pyridin-4-ylmethyl)-amino]-benzamide Step A: Preparation of 2-nitro-N-{4-[1-methyl-1-(1-methylpiperidin-4-yl)ethyl]phenyl}benzamide To a mixture of 2-nitrobenzoic acid (400 mg), 4-[1-methyl-1-(1-methylpiperidin-4-yl)-ethyl]phenylamine (Preparation IV (aw)) (600 mg) and DIEA (0.6 mL) in $CH_2Cl_2$ (80 mL) was added EDC (600 mg) and HOBt (350 mg). The reaction was stirred at RT overnight and washed with saturated $NaHCO_3$ (30 mL), $H_2O$ (50 mL) and brine (30 mL). The organic layer was dried over $Na_2SO_4$ and evaporated to give 2-nitro-N-{4-[1-methyl-1-(1-methylpiperidin-4-yl)ethyl]phenyl}benzamide which was used in the next step without further purification.

Step B: Preparation of 2-amino-N-{4-[1-methyl-1-(1-methyl-piperidin-4-yl)-ethyl]-phenyl}-benzamide 2-Nitro-N-{4-[1-methyl-1-(1-methylpiperidin-4-yl)ethyl]phenyl}benzamide (Step A, 750 mg) was mixed with Pd/C (10%, 200 mg) in EtOH (80 mL) and hydrogenated under a hydrogen atmosphere for 1 h. The solution was filtered through Celite® and evaporated to give the amine used in the next step without further purification.

Step C: Preparation of N-{4-[1-methyl-1-(1-methyl-piperidin-4-yl)-ethyl]-phenyl}-2-[(pyridin-4-ylmethyl)-amino]-benzamide A mixture of 2-amino-N-{4-[1-methyl-1-(1-methyl-piperidin-4-yl)ethyl]phenyl}benzamide (600 mg, Step B) and 4-pyridinecarboxaldehyde (0.22 mL) was heated at reflux in EtOH (50 mL) overnight. $NaBH_4$ (250 mg) was added and the mixture was heated at reflux for 10 min and evaporated. The residue was mixed with $CH_2Cl_2$ and washed with $H_2O$ twice, followed by brine. The organic layer was dried over $Na_2SO_4$ and evaporated under reduced pressure. The residue was purified by column chromatography using 10% MeOH/$CH_2Cl_2$ to provide the title compound. MS (ES+): 443 $(M+H)^+$. Calc'd. for $C_{28}H_{34}N_4O$-442.27.

Examples 2-6 were synthesized by methods similar to that described in Example 1 unless specifically described.

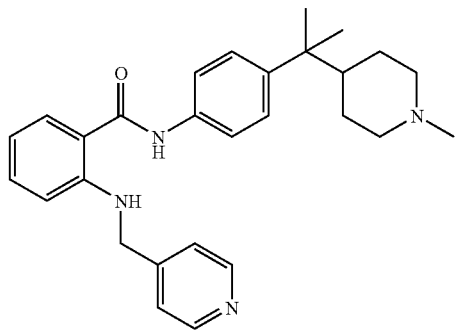

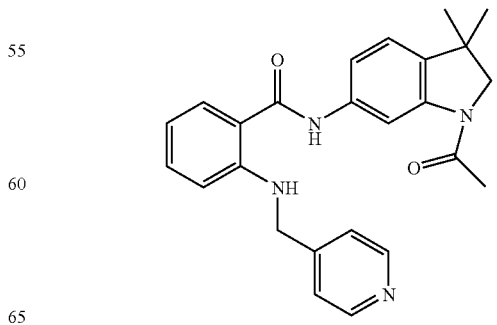

N-(1-Acetyl-3,3-dimethyl-2,3-dihydro-1H-indol-6-yl)-2-[(pyridin-4-ylmethyl)-amino]-benzamide MS: (ES+) 415 (M+H). Calc'd. for $C_{25}H_{26}N_4O_2$-414.21.

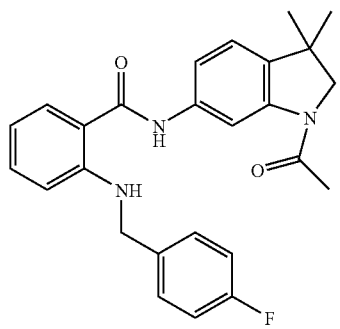

N-(1-Acetyl-3,3-dimethyl-2,3-dihydro-1H-indol-6-yl)-2-(4-fluoro-benzylamino)-benzamide MS: (ES+) 432(M+H). Calc'd. for $C_{26}H_{26}FN_3O_2$-431.20.

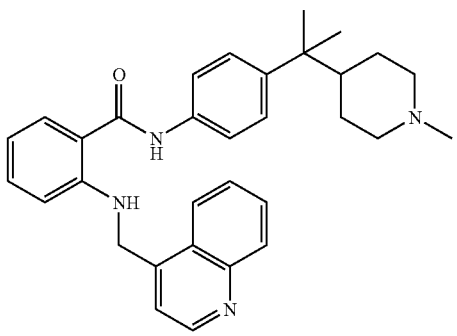

N-{4-[1-Methyl-1-(1-methyl-piperidin-4-yl)-ethyl]-phenyl}-2-[(quinolin-4-ylmethyl)-amino]-benzamide MS: (ES+) 493(M+H). Calc'd. for $C_{32}H_{36}N_4O$-492.29.

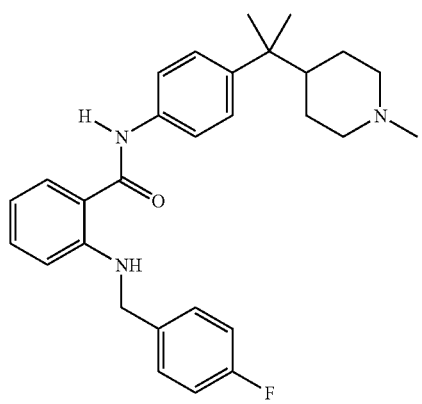

2-(4-Fluoro-benzylamino)-N-{4-[1-methyl-1-(1-methyl-piperidin-4-yl)-ethyl]-phenyl}-benzamide MS: (ES+) 460 (M+H). Calc'd. for $C_{29}H_{34}FN_3O$-459.61.

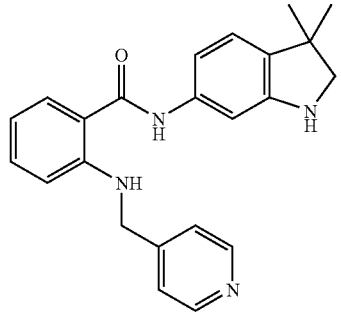

N-(3,3-Dimethyl-2,3-dihydro-1H-indol-6-yl)-2-[(pyridin-4-ylmethyl)-amino]-benzamide N-(1-Acetyl-3,3-dimethyl-2,3-dihydro-1H-indol-6-yl)-2-[(pyridin-4-ylmethyl)-amino]-benzamide (Example 2, 120 mg) was heated with HCl (5 N, 2.5 mL) and H₂O (2.5 mL) to reflux for 2 h. The solvent was evaporated and the residue was washed with MeOH. The desired compound was collected after filtration as an off-white solid. MS: (ES+) 373 (M+H). Calc'd. for $C_{23}H_{24}N_4O$-372.20.

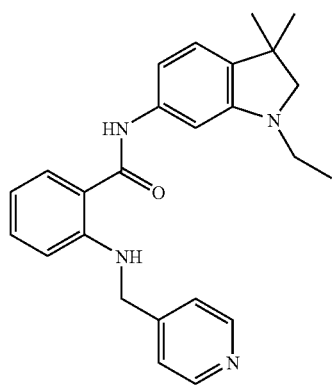

N-(1-Ethyl-3,3-dimethyl-2,3-dihydro-1H-indol-6-yl)-2-[(pyridin-4-ylmethyl)-amino]-benzamide Step A: Preparation of N-(1-acetyl-3,3-dimethyl-2,3-dihydro-1H-indol-6-yl)-2-nitro-benzamide N-(1-Acetyl-3,3-dimethyl-2,3-dihydro-1H-indol-6-yl)-2-nitro-benzamide was prepared from N-[1-acetyl-3,3-dimethyl-2,3-dihydro-6-(1H-indole)] and 2-nitrobenzoic acid similar to the method described in Example 1, Step A.

Step B: Preparation of N-(3,3-dimethyl-2,3-dihydro-1H-indol-6-yl)-2-nitro-benzamide N-(1-Acetyl-3,3-dimethyl-2,3-dihydro-1H-indol-6-yl)-2-nitro-benzamide (Step A) (3.0 g, 8.5 mmol) was dissolved in EtOH (80 mL) in the presence of HCl (1 N, 18 mL). The solution was heated to 70° C. overnight. Solvent was removed in vacuo and the residue was partitioned in EtOAc and a solution of NaHCO$_3$ (aq. sat.). A yellow precipitate formed in the organic layer. After separation from the aqueous layer, the organic layer was filtered to give a solid. The filtrate was concentrated to give a second batch. The combined batches were used without further purification.

Step C: Preparation of N-(1-ethyl-3,3-dimethyl-2,3-dihydro-1H-indol-6-yl)-2-nitro-benzamide N-(3,3-Dimethyl-2,3-dihydro-1H-indol-6-yl)-2-nitro-benzamide (Step B) (300 mg, 0.96 mmol) was treated with acetaldehyde (70 μL) and NaBH(OAc)$_3$ (300 mg, 1.4 mmol) in CH$_2$Cl$_2$ (50 mL) overnight. After drying in vacuo, the reaction mixture was purified via flash chromatography on silica gel using EtOAc to afford the desired compound.

Step D: Preparation of N-(1-ethyl-3,3-dimethyl-2,3-dihydro-1H-indol-6-yl)-2-[(pyridin-4-ylmethyl)-amino]-benzamide The title compound was prepared following a procedure analogous to that described for Example 1 Steps B-C. MS (ES+): 401 (M+H)$^+$. Calc'd. for C$_{25}$H$_{28}$N$_4$O-400.52.

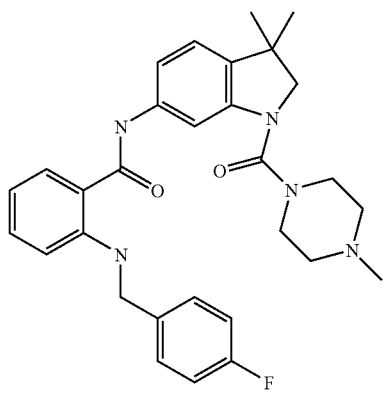

N-[3,3-Dimethyl-1-(4-methyl-piperazine-1-carbonyl)-2,3-dihydro-1H-indol-6-yl]-2-(4-fluoro-benzylamino)-benzamide Step A: Preparation of N-[3,3-dimethyl-1-(4-methyl-piperazine-1-carbonyl)-2,3-dihydro-1H-indol-6-yl]-2-nitro-benzamide N-(3,3-dimethyl-2,3-dihydro-1H-indol-6-yl)-2-nitro-benzamide (Example 7, Step A)(300 mg, 0.96 mmol) was treated with 4-methyl-piperazine-1-carbonyl chloride (200 mg, 1 mmol) in the presence of DIEA (40 mL) in THF overnight at 65° C. The mixture was partitioned between EtOAc and saturated aqueous NaHCO$_3$. The organic layer was washed with H$_2$O and brine, then dried over Na$_2$SO$_4$. The organic solution was concentrated in vacuo to yield the desired compound.

Step B: Preparation of N-[3,3-dimethyl-1-(4-methyl-piperazine-1-carbonyl)-2,3-dihydro-1H-indol-6-yl]-2-(4-fluoro-benzylamino)-benzamide N-[3,3-Dimethyl-1-(4-methyl-piperazine-1-carbonyl)-2,3-dihydro-1H-indol-6-yl]-2-nitro-benzamide (Step A) was used to prepare the title compound following procedures analogous to that described for Example 1. MS: (ES+) 516, (M+H). Calc'd. for C$_{30}$H$_{34}$FN$_5$O$_2$-515.63.

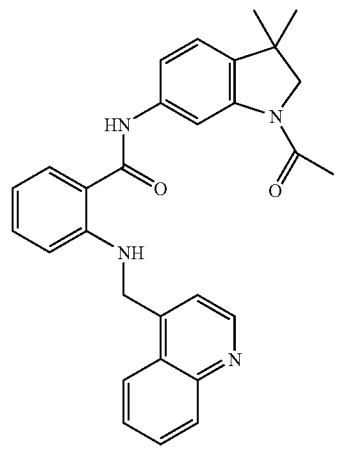

N-(1-Acetyl-3,3-dimethyl-2,3-dihydro-1H-indol-6-yl)-2-[(quinolin-4-ylmethyl)-amino]-benzamide Step A: Preparation of N-(1-acetyl-3,3-dimethyl-2,3-dihydro-1H-indol-6-yl)-2-amino-benzamide A mixture of 1-(6-amino-3,3-dimethyl-2,3-dihydro-indol-1-yl)-ethanone (1.02 g, 5 mmol) and isatoic anhydride (0.85 g, 5.2 mmol) in DMSO (5 mL) was heated to 150° C. for 6 h. After cooling to RT, the mixture was suspended in a NaHCO$_3$ solution (40 mL) and extracted with CH$_2$Cl$_2$ (20 mL×3). The organic solution was combined and concentrated in vacuo. The residue was purified via flash chromatography on silica gel (EtOAc:hexanes 9:2) to give the desired compound as an off-white solid.

Step B: Preparation of N-(1-acetyl-3,3-dimethyl-2,3-dihydro-1H-indol-6-yl)-2-[(quinolin-4-ylmethyl)-amino]-benzamide The preparation of the title compound was prepared analogous to that described for Example 1 (Step C). MS: (ES+) 465, (M+H). Calc'd. for C$_{29}$H$_{28}$N$_4$O$_2$-464.57.

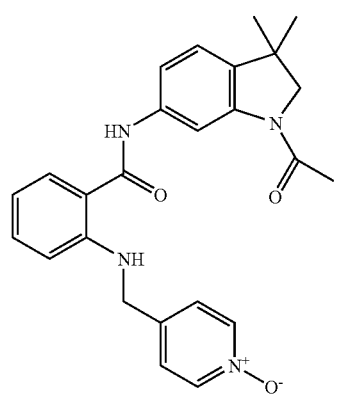

N-(1-Acetyl-3,3-dim thyl-2,3-dihydro-1H-indol-6-yl)-2-[(1-oxy-pyridin-4-ylmethyl)-amino]-benzamide The compound was prepared analogous to that described for Example 9. MS: (ES+) 431, (M+H). Calc'd. for $C_{25}H_{26}N_4O_3$-430.50.

N-(3,3-Dimethyl-2,3-dihydro-1H-indol-6-yl)-2-[(quinolin-4-ylmethyl)-amino]-benzamide N-(1-Acetyl-3,3-dimethyl-2,3-dihydro-1H-indol-6-yl)-2-[(quinolin-4-ylmethyl)-amino]-benzamide (Example 9) (150 mg, 0.32 mmol) was dissolved in EtOH (15 mL) and concentrated aqueous HCl (5 mL) and the mixture was heated to 50° C. overnight, then 80° C. for 2 h. After drying in vacuo, the residue was partitioned between $CH_2Cl_2$ and aqueous $NaHCO_3$. The organic layer was collected, washed with brine, and dried over $Na_2SO_4$. After concentrated in vacuo, the desired product was isolated as a white solid. MS: (ES+) 423, (M+H). Calc'd. for $C_{27}H_{26}N_4O$-422.53.

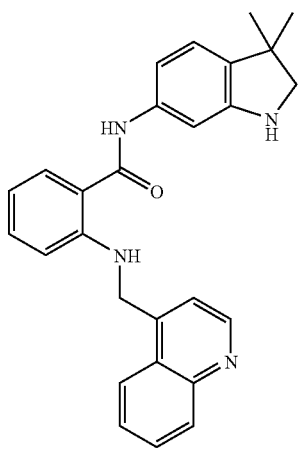

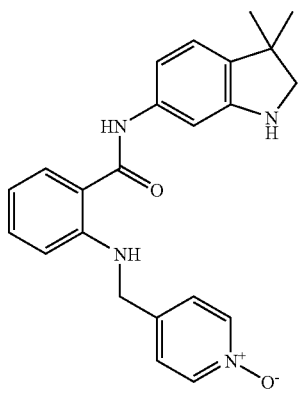

N-(3,3-Dimethyl-2,3-dihydro-1H-indol-6-yl)-2-[(1-oxy-pyridin-4-ylmethyl)-amino]-benzamide The title compound was prepared analogously to that described in Example 11 from N-(1-acetyl-3,3-dimethyl-2,3-dihydro-1H-indol-6-yl)-2-[(1-oxy-pyridin-4-ylmethyl)-amino]-benzamide (Example 10). MS: (ES+) 389, (M+H). Calc'd. for $C_{23}H_{24}N_4O_2$-388.47.

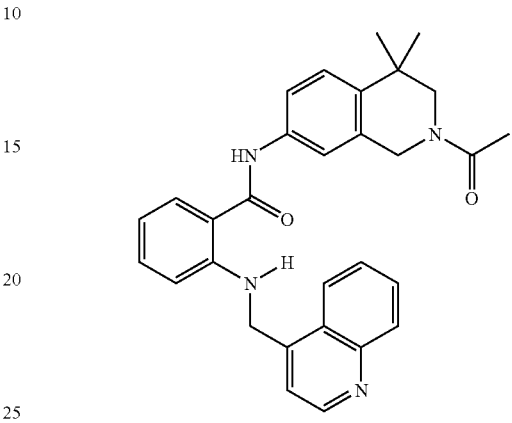

N-(2-Acetyl-4,4-dim thyl-1,2,3,4-tetrahydro-isoquinolin-7-yl)-2-[(quinolin-4-ylmethyl)-amino]-benzamide Step A: Preparation of 1-(4,4-Dimethyl-7-nitro-3,4-dihydro-1H-isoquinolin-2-yl)-ethanone A mixture of 4-(dimethylamino)pyridine (0.125 g, 1.02 mmol), 4,4-dimethyl-7-nitro-1,2,3,4-tetrahydro-isoquinoline (0.21 g, 1.02 mmol), DIEA (0.53 mL, 3.06 mmol), and $Ac_2O$ (0.19 mL, 2.04 mmol) in 7 mL of $CH_2Cl_2$ was stirred at RT under $N_2$ for two days. The volatiles were removed under vacuum. The residue was partitioned between EtOAc and brine, and the organic portion was dried with $Na_2SO_4$, filtered, and concentrated. The crude material was purified by flash column chromatography (2-3% MeOH in $CH_2Cl_2$), to yield the desired compound as a light yellowish solid. MS (ES+): 249.3 (M+H)+. Calc'd for $C_{13}H_{16}N_2O_3$-248.28.

Step B: Preparation of 1-(7-amino-4,4-dimethyl-1,2,3,4-tetrahydro-naphthalen-2-yl)-ethanone A mixture of 1-(4,4-dimethyl-7-nitro-3,4-dihydro-1H-isoquinolin-2-yl)-ethanone (Step A) (0.25 g) and Pd/C (10 wt %, 50 mg) in MeOH (10 mL) was placed under $H_2$ and stirred at RT for 4 h, filtered through Celite®, the solvents were removed to yield the title compound as light brownish oil. MS (ES+): 219.1 (M+H)+. Calc'd for $C_{14}H_{19}NO$-218.29.

Step C: Preparation of N-(2-acetyl-4,4-dimethyl-1,2,3,4-tetrahydro-isoquinolin-7-yl)-2-[(quinolin-4-ylmethyl)-amino]-benzamide The preparation of the title compound was analogous to that described for Example 1 starting with 1-(7-amino-4,4-dimethyl-1,2,3,4-tetrahydro-naphthalen-2-yl)-ethanone. The compound was obtained as an off-white solid. MS (ES+): 479. (M+H)+. Calc'd for $C_{30}H_{30}N_4O_2$-478.58.

Other compounds included in this invention are set forth in Tables 1-4 below.

TABLE 1

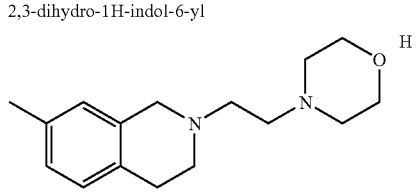

| # | R¹ | R² |
|---|---|---|
| 14. | 1,2,3,4-tetrahydroquinolin-7-yl | H |
| 15. | 1-oxo-1,2,3,4-tetrahydroisoquinolin-7-yl | H |
| 16. | 5,6,7-trihydro-1,2,4-triazolo[3,4-a]isoquinolin-2-yl | H |
| 17. | 3,3-dimethyl-1-(4-piperidylmethyl)indolin-6-yl | H |
| 18. | 3,3-dimethyl-1-(1-methyl-piperidin-4-yl-methyl)-2,3-dihydro-1H-indol-6-yl | H |
| 19. | 1-(1-methyl (4-piperidyl))indolin-6-yl | H |
| 20. | 3,3-dimethyl-1-(1-methyl(4-piperidyl))-indolin-6-yl | H |
| 21. | 3,3-Dimethyl-1,1-dioxo-2,3-dihydro-1H-1λ⁶-benzo[d]isothiazol-6-yl | H |
| 22. | 4-acetyl-2,2-dimethyl-3,4-dihydro-2H-benzo[1,4]oxazin-6-yl | H |
| 23. | 2,2,4-trimethyl-3,4-dihydro-2H-benzo[1,4]oxazin-6-yl | H |
| 24. | 2,2-dimethyl-3,4-dihydro-2H-benzo[1,4]oxazin-6-yl | H |
| 25. | 4,4-dimethyl-1-oxo-1,2,3,4-tetrahydro-isoquinolin-7-yl | H |
| 26. | 3,3-dimethyl-2,3-dihydro-benzofuran-6-yl | H |
| 27. | 1-(2-dimethylamino-acetyl)-3,3-dimethyl-2,3-dihydro-1H-indol-6-yl | H |
| 28. | 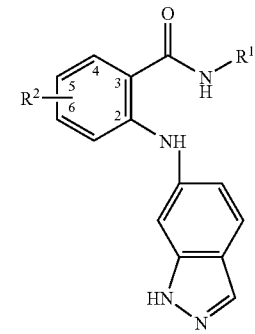 | H |
| 29. | 4,4-dimethyl-1,2,3,4-tetrahydro-isoquinolin-7-yl | H |
| 30. | indolin-6-yl | H |
| 31. | 1-acetyl-indolin-6-yl | H |
| 32. | 1-(2-piperidylethyl)indolin-6-yl | H |
| 33. | 1-(2-piperidylacetyl)indolin-6-yl | H |
| 34. | 2,3,3-trimethyl-1,1-dioxo-2,3-dihydro-1H-1λ⁶-benzo[d]isothiazol-6-yl | H |

TABLE 2

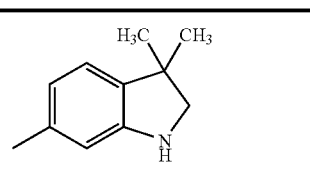

| # | R¹ | R² |
|---|---|---|
| 35. | 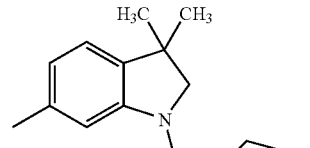 | H |
| 36. | 1,2,3,4-tetrahydroquinolin-7-yl | H |
| 37. | 1-oxo-1,2,3,4-tetrahydroisoquinolin-7-yl | H |
| 38. | 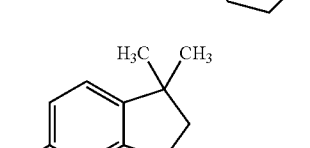 | H |
| 39. | 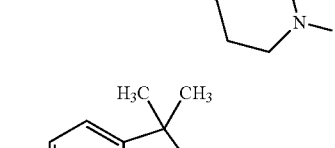 | H |
| 40. | 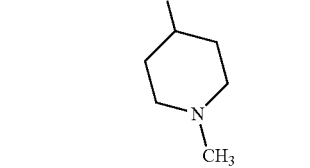 | H |
| 41. |  | H |

| # | | R¹ | R² |
|---|---|---|---|
| 42. | [structure: 6-methyl-tetrahydroisoquinoline-N-ethyl-morpholine] | | H |
| 43. | [structure: 7-methyl-tetrahydroisoquinoline-N-ethyl-morpholine] | | H |
| 44. | 5,6,7-trihydro-1,2,4-triazolo[3,4-a]isoquinolin-2-yl | | H |
| 45. | 1-(1-methyl(4-piperidyl))indolin-6-yl | | H |
| 46. | 3,3-dimethyl-1,1-dioxo-2,3-dihydro-1H-1λ⁶-benzo[d]isothiazol-6-yl | | H |
| 47. | 1-acetyl-3,3-dimethyl-2,3-dihydro-1H-indol-6-yl | | H |
| 48. | 4-acetyl-2,2-dimethyl-3,4-dihydro-2H-benzo[1,4]oxazin-6-yl | | H |
| 49. | 2,2,4-trimethyl-3,4-dihydro-2H-benzo[1,4]oxazin-6-yl | | H |
| 50. | 2-acetyl-4,4-dimethyl-1,2,3,4-tetrahydro-isoquinolin-7-yl | | H |
| 51. | 2,2-dimethyl-3,4-dihydro-2H-benzo[1,4]oxazin-6-yl | | H |
| 52. | 4,4-dimethyl-1-oxo-1,2,3,4-tetrahydro-isoquinolin-7-yl | | H |
| 53. | 3,3-dimethyl-2,3-dihydro-benzofuran-6-yl | | H |
| 54. | 1-(2-dimethylamino-acetyl)-3,3-dimethyl-2,3-dihydro-1H-indol-6-yl | | H |
| 55. | 4,4-dimethyl-1,2,3,4-tetrahydro-isoquinolin-7-yl | | H |
| 56. | indolin-6-yl | | H |
| 57. | 1-acetyl-indolin-6-yl | | H |
| 58. | 1-(2-piperidylethyl)indolin-6-yl | | H |
| 59. | 2-oxo-4-trifluoromethyl-2H-chromen-7-yl | | H |
| 60. | 1-(1-Methyl-(4-piperidyl))indolin-6-yl | | H |
| 61. | 1-(2-Piperidylethyl)indolin-6-yl | | H |
| 62. | 1-(2-Piperidylacetyl)indolin-6-yl | | H |

TABLE 3

[structure: benzamide with NH-quinolin-6-yl substituent at position 2, R² at position 6, C(O)NH-R¹]

| # | R¹ | R² |
|---|---|---|
| 63. | 1,2,3,4-tetrahydroquinolin-7-yl | H |
| 64. | 1-oxo-1,2,3,4-tetrahydraisoquinolin-7-yl | H |
| 65. | 5,6,7-trihydro-1,2,4-triazolo[3,4-a]isoquinolin-2-yl | H |
| 66. | 3,3-dimethyl-1-(4-piperidylmethyl)indolin-6-yl | H |
| 67. | 3,3-dimethyl-1-(1-methyl-piperidin-4-yl-methyl)-2,3-dihydro-1H-indol-6-yl | H |
| 68. | 1-(1-methyl(4-piperidyl))indolin-6-yl | H |
| 69. | 3,3-dimethyl-1-(1-methyl(4-piperidyl))-indolin-6-yl | H |
| 70. | 3,3-dimethy1-1,1-dioxo-2,3-dihydro-1H-1λ⁶-benzo[d]isothiazol-6-yl | H |
| 71. | 1-acetyl-3,3-dimethyl-2,3-dihydro-1H-indol-6-yl | H |

TABLE 3-continued

[structure: benzamide with NH-quinolin-6-yl substituent]

| # | R¹ | R² |
|---|---|---|
| 72. | 4-acetyl-2,2-dimethyl-3,4-dihydra-2H-benzo[1,4]oxazin-6-yl | H |
| 73. | 2,2,4-trimethyl-3,4-dihydro-2H-benzo[1,4]oxazin-6-yl | H |
| 74. | 2-acetyl-4,4-dimethyl-1,2,3,4-tetrahydra-isoquinolin-7-yl | H |
| 75. | 4,4-Dimethyl-1-oxo-1,2,3,4-tetrahydro-isoquinolin-7-yl | H |
| 76. | 3,3-dimethyl-2,3-dihydro-benzofuran-6-yl | H |
| 77. | 1-(2-dimethylamino-acetyl)-3,3-dimethyl-2,3-dihydro-1H-indol-6-yl | H |
| 78. | indolin-6-yl | H |
| 79. | 1-acetyl-indolin-6-yl | H |
| 80. | 2,3,3-trimethyl-1,1-dioxo-2,3-dihydro-1H-1λ'-benzo[d]isothiazol-6-yl | H |

TABLE 4

[structure: benzamide with NHCH₂-pyridin-4-yl substituent at position 2, R² at position 6, C(O)NH-R¹]

| # | R¹ | R² |
|---|---|---|
| 81. | 1,2,3,4-tetrahydroquinolin-7-yl | H |
| 82. | 1-oxo-1,2,3,4-tetrahydroisoquinalin-7-yl | H |
| 83. | 5,6,7-trihydro-1,2,4-triazolo[3,4-a]isoquinolin-2-yl | H |
| 84. | 3,3-dimethyl-1-(4-piperidylmethyl)indolin-6-yl | H |
| 85. | 3,3-dimethyl-1-(1-methyl-piperidin-4-yl-methyl)-2,3-dihydro-1H-indol-6-yl | H |
| 86. | 1-(1-methyl(4-piperidyl))indolin-6-yl | H |
| 87. | 3,3-dimethyl-1-(1-methyl(4-piperidyl))-indolin-6-yl | H |
| 88. | 3,3-dimethyl-1,1-dioxo-2,3-dihydro-1H-1λ⁶-benzo[d]isothiazol-6-yl | H |
| 89. | 1-acetyl-3,3-dimethyl-2,3-dihydro-1H-indol-6-yl | H |
| 90. | 4-acetyl-2,2-dimethyl-3,4-dihydro-2H-benzo[1,4]oxazin-6-yl | H |

TABLE 4-continued

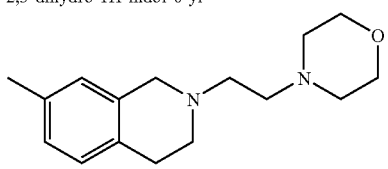

| # | R¹ | R² |
|---|---|---|
| 91. | 2,2,4-trimethyl-3,4-dihydro-2H-benzo[1,4]oxazin-6-yl | H |
| 92. | 2-acetyl-4,4-dimethyl-1,2,3,4-tetrahydro-isoquinolin-7-yl | H |
| 93. | 2,2-dimethyl-3,4-dihydro-2H-benzo[1,4]oxazin-6-yl | H |
| 94. | 4,4-Dimethyl-1-oxo-1,2,3,4-tetrahydro-isoquinolin-7-yl | H |
| 95. | 3,3-dimethyl-2,3-dihydro-benzofuran-6-yl | H |
| 96. | 1-(2-dimethylamino-acetyl)-3,3-dimethyl-2,3-dihydro-1H-indol-6-yl | H |
| 97. | 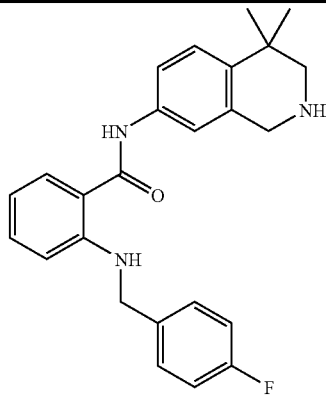 | H |
| 98. | 4,4-dimethyl-1,2,3,4-tetrahydro-isoquinolin-7-yl | H |
| 99. | indolin-6-yl | H |
| 100. | 1-acetyl-indolin-6-yl | H |
| 101. | 1-(2-piperidylethyl)indolin-6-yl | H |
| 102. | 1-(2-piperidylacetyl)indolin-6-yl | H |
| 103. | 2,3,3-trimethyl-1,1-dioxo-2,3-dihydro-1H-1λ⁶-benzo[d]isothiazol-6-yl | H |

N-(4,4-Dimethyl-1,2,3,4-tetrahydro-isoquinolin-7-yl)-2-(4-fluoro-benzylamino)-benzamide Step A: Preparation of 2-(4-fluorobenzylamino)benzoic acid A mixture of anthranilic acid (1.37 g, 1.0 mmol), 4-fluorobenzaldehyde (1.24 g, 1.0 mmol), and p-toluenesulfonic acid mohohydrate (0.025 g, 0.13 mmol) in 30 mL of anhydrous toluene was stirred at reflux for 1 h, then cooled to RT and NaBH₄ (1.1 g) was added. The mixture was stirred at RT for 30 min, then quenched with MeOH. The volatiles were removed under reduced pressure and the residue was taken up in water. AcOH was added to bring pH to 4, and the mixture was extracted with EtOAc. The combined organic portions were washed with brine, dried over MgSO₄, filtered, condensed, and the residue was purified by flash column chromatography to give the titled compound. MS (ES+): 246.0 (M+H)⁺. Calc'd for $C_{14}H_{12}FNO_2$-245.09.

Step B: Preparation of 7-[2-(4-fluorobenzylamino)-benzoylamino]-4,4-dimethyl-3,4-dihydro-1H-isoquinoline-2-carboxylic acid tert-butyl ester The mixture of 2-(4-fluorobenzylamino)benzoic acid (Step A, 0.7 g, 1.20 mmol), 7-amino-4,4-dimethyl-3,4-dihydro-1H-isoquinoline-2-carboxylic acid tert-butyl ester (0.71 g, 2.57 mmol), TBTU (0.917 g, 2.86 mmol), and DIEA (0.5 mL) in 30 mL of CH₂Cl₂ was stirred at RT for 2 h, then diluted with more CH₂Cl₂. The organic layer was washed with water, and brine, dried with MgSO₄, filtered, and condensed. The residue was purified by flash column chromatography (0 to 30% of EtOAc in CH₂Cl₂), and the titled compound was obtained as oil. MS (ES+): 504 (M+H)⁺. Calc'd for $C_{30}H_{34}FN_3O_3$-503.26.

Step C: Preparation of N-(4,4-dimethyl-1,2,3,4-tetrahydro-isoquinolin-7-yl)-2-(4-fluoro-benzylamino)-benzamide 7-[2-(4-Fluoro-benzylamino)-benzoylamino]-4,4-dimethyl-3,4-dihydro-1H-isoquinoline-2-carboxylic acid tert-butyl ester (Step B, 0.57 g, 1.13 mmol) was treated with 10 mL of 50% of TFA in CH₂Cl₂ and stirred at RT for 1 h. The volatiles were removed under reduced pressure, and the residue was purified by flash column chromatography. The titled compound was obtained as a white solid. MS (ES⁺): 404 (M+H)⁺. Calc'd for $C_{25}H_{26}FN_3O$-403.21.

Examples 105-108 were synthesized by methods similar to that described in Example 104.

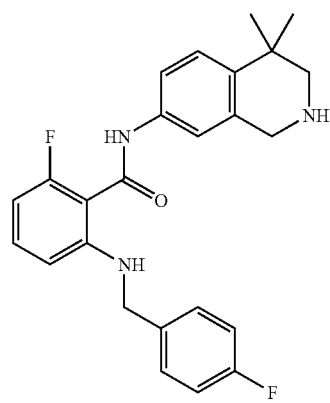

N-(4,4-Dimethyl-1,2,3,4-tetrahydro-isoquinolin-7-yl)-2-fluoro-6-(4-fluoro-benzylamino)-benzamide MS (ES⁺): 422 (M+H)⁺. Calc'd for $C_{25}H_{25}F_2NO$-421.2.

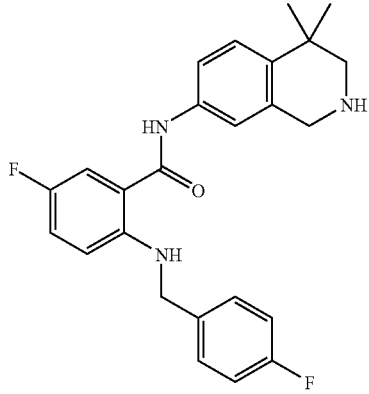

N-(4,4-Dimethyl-1,2,3,4-tetrahydro-isoquinolin-7-yl)-3-fluoro-6-(4-fluoro-benzylamino)-benzamide MS (ES⁺): 422 (M+H)⁺. Calc'd for $C_{25}H_{25}F_2NO$-421.2.

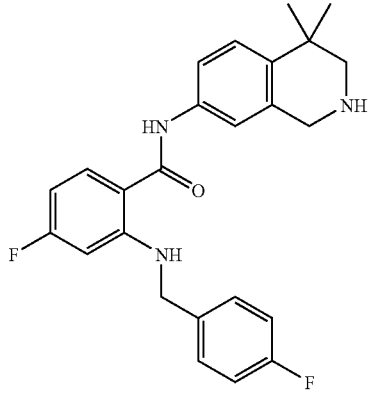

N-(4,4-Dimethyl-1,2,3,4-tetrahydro-isoquinolin-7-yl)-4-fluoro-6-(4-fluoro-benzylamino)-benzamide MS (ES⁺): 422 (M+H)⁺. Calc'd for $C_{25}H_{25}F_2NO$-421.2.

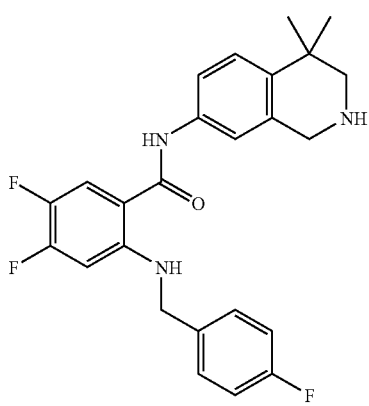

N-(4,4-Dimethyl-1,2,3,4-tetrahydro-isoquinolin-7-yl)-3,4-difluoro-6-(4-fluoro-benzylamino)-benzamide MS (ES⁺): 440 (M+H)⁺. Calc'd for $C_{25}H_{24}F_3N_3O$-439.19.

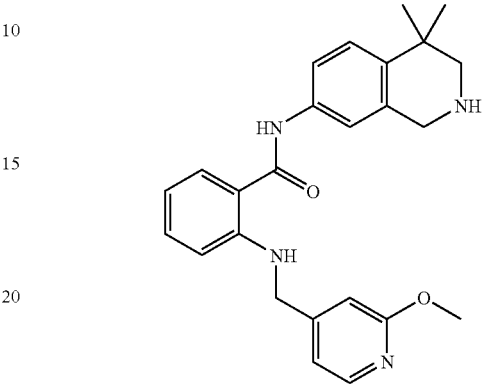

N-(4,4-Dimethyl-1,2,3,4-tetrahydro-isoquinolin-7-yl)-2-[(2-methoxy-pyridin-4-ylmethyl)-amino]-benzamide Step A: Preparation of 2-[(2-methoxy-pyridin-4-ylmethyl)-amino]-benzoic acid A mixture of anthranilic acid (1.37 g, 1.0 mmol), 2-methoxy-pyridine-4-carbaldehyde (1.37 g, 1.0 mmol), and p-toluenesulfonic acid mohohydrate (0.025 g, 0.13 mmol) in 30 mL of anhydrous toluene was stirred at reflux for 1 h, cooled to RT, and NaBH₄ (0.9 g) was added. The mixture was stirred at RT for 30 min, and quenched with MeOH. The volatiles were removed under reduced pressure, and the residue was taken up in water. AcOH was added to bring pH to 4, and the mixture was extracted with EtOAc. The combined organic portions were washed with brine, dried over MgSO₄, filtered, and condensed. The residue was purified by flash column chromatography to give the titled compound. MS (ES⁺): 259.0 (M+H)⁺. Calc'd for $C_{14}H_{12}N_2O_3$-258.10.

Step B: Preparation of 7-{2-[(2-methoxy-pyridin-4-ylmethyl)-amino]-benzoylamino}-4,4-dimethyl-3,4-dihydro-1H-isoquinoline-2-carboxylic acid tert-butyl ester A mixture of 2-[(2-methoxy-pyridin-4-ylmethyl)-amino]-benzoic acid (Step A, 516 mg, 2.0 mmol), 7-amino-4,4-dimethyl-3,4-dihydro-1H-isoquinoline-2-carboxylic acid tert-butyl ester (552 mg, 2.0 mmol), TBTU (0.706 g, 2.2 mmol), and DIEA (0.7 mL) in 30 mL of CH₂Cl₂ was stirred at RT for 2 h. The mixture was diluted with more CH₂Cl₂. The organic layer was washed with water, brine, and dried with MgSO₄. The solution was filtered, condensed, and the residue was purified by flash column chromatography (0 to 30% of EtOAc in CH₂Cl₂) to obtain the titled compound as oil. MS (ES⁺): 517.2 (M+H)⁺. Calc'd for $C_{30}H_{36}N_4O_4$-516.27.

Step C: Preparation of N-(4,4-dimethyl-1,2,3,4-tetrahydro-isoquinolin-7-yl)-2-[(2-methoxy-pyridin-4-ylmethyl)-amino]-benzamide 7-{(2-[(2-Methoxy-pyridin-4-ylmethyl)-amino]-benzoylamino}-4,4-dimethyl-3,4-dihydro-1H-isoquinoline-2-carboxylic acid tert-butyl ester (Step B, 0.52 g, 0.84 mmol) was treated with 10 mL of a 1/1 TFA/CH$_2$Cl$_2$ solution. The mixture was stirred at RT for 1 h, then volatiles were removed under reduced pressure and the residue was purified by flash column chromatography. The titled compound was obtained as a white solid. MS (ES+): 416.9 (M+H)$^+$. Calc'd for C$_{25}$H$_{28}$N$_4$O$_2$-416.22.

Examples 110-112 were synthesized by methods similar to that described in Example 109.

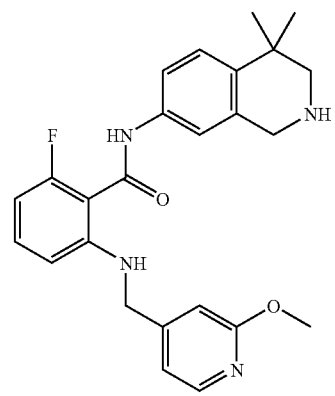

N-(4,4-Dimethyl-1,2,3,4-tetrahydro-isoquinolin-7-yl)-2-fluoro-6-[(2-methoxy-pyridin-4-ylmethyl)-amino]-benzamide MS (ES$^+$): 435.0 (M+H)$^+$. Calc'd for C$_{25}$H$_{27}$FN$_4$O$_2$-434.21.

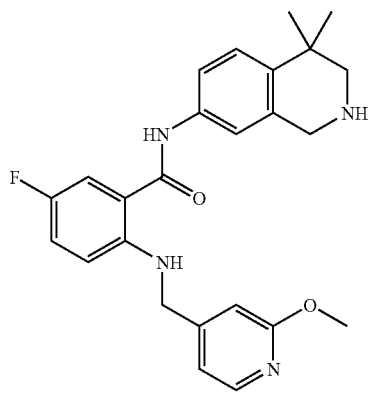

N-(4,4-Dimethyl-1,2,3,4-tetrahydro-isoquinolin-7-yl)-3-fluoro-6-[(2-methoxy-pyridin-4-ylmethyl)-amino]-benzamide MS (ES$^+$): 435.0 (M+H)$^+$. Calc'd for C$_{25}$H$_{27}$FN$_4$O$_2$-434.21.

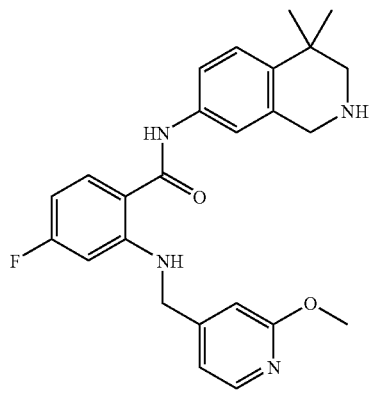

N-(4,4-Dimethyl-1,2,3,4-tetrahydro-isoquinolin-7-yl)-4-fluoro-6-[(2-methoxy-pyridin-4-ylmethyl)-amino]-benzamide MS (ES$^+$): 435.0 (M+H)$^+$. Calc'd for C$_{25}$H$_{27}$FN$_4$O$_2$-434.21.

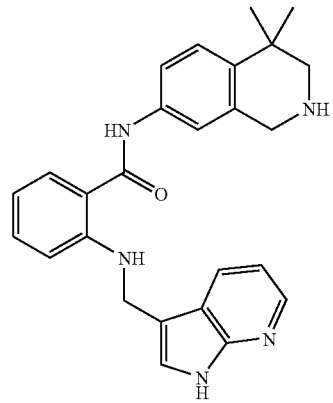

N-(4,4-Dimethyl-1,2,3,4-tetrahydro-isoquinolin-7-yl)-2-[(1H-pyrrolo [2,3-b]pyridin-3-ylmethyl)-amino]-benzamide

Step A: Preparation of 2-[(1H-pyrrolo[2,3-b]pyridin-3-ylmethyl)-amino]-benzoic acid A mixture of anthranilic acid (1.37 g, 1.0 mmol), 1H-pyrrolo[2,3-b]pyridine-3-carbaldehyde (1.46 g, 1.0 mmol), and p-toluenesulfonic acid mohohydrate (0.025 g, 0.13 mmol) in 30 mL of anhydrous toluene was stirred at reflux for 1 h. After being cooled to RT, NaBH$_4$ (0.9 g) was added, and the mixture was stirred at RT for 30 min. The reaction was quenched with MeOH, and the volatiles were removed under reduced pressure. The residue was taken up in water, AcOH was added to bring pH to 4, and the mixture was extracted with EtOAc. The combined organic portions were washed with brine, dried over MgSO$_4$, filtered, and condensed. The residue was purified by flash column chromatography to give the titled compound. MS (ES$^+$): 268.1 (M+H)$^+$. Calc'd for C$_{15}$H$_{13}$N$_3$O$_2$-267.10.

Step B: Preparation of 4,4-dimethyl-7-{2-[(1H-pyr-rolo[2,3-b]pyridin-3-ylmethyl)-amino]-benzoylamino}-3,4-dihydro-1H-isoquinoline-2-carboxylic acid tert-butyl ester A mixture of 2-[(1H-pyrrolo[2,3-b]pyridin-3-ylmethyl)-amino]-benzoic acid (Step A, 516 mg, 2.0 mmol), 7-amino-4,4-dimethyl-3,4-dihydro-1H-isoquinoline-2-carboxylic acid tert-butyl ester (552 mg, 2.0 mmol), TBTU (0.706 g, 2.2 mmol), and DIEA (0.7 mL) in 30 mL of $CH_2Cl_2$ was stirred at RT for 2 h, then diluted with more $CH_2Cl_2$. The organic layer was washed with water, brine, dried with $MgSO_4$, filtered, and condensed. The residue was purified by flash column chromatography (0 to 30% of EtOAc in $CH_2Cl_2$), to obtain the titled compound as oil. MS ($ES^+$): 526 $(M+H)^+$. Calc'd for $C_{31}H_{35}N_5O_3$-525.27.

Step C: Preparation of N-(4,4-dimethyl-1,2,3,4-tetrahydro-isoquinolin-7-yl)-2-[(1H-pyrrolo[2,3-b]pyridin-3-ylmethyl)-amino]-benzamide 4,4-Dimethyl-7-{2-[(1H-pyrrolo[2,3-b]pyridin-3-ylmethyl)-amino]-benzoylamino}-3,4-dihydro-1H-isoquinoline-2-carboxylic acid tert-butyl ester (Step B, 0.45 g, 0.86 mmol) was treated with 10 mL of 1/1 $TFA/CH_2Cl_2$ solution and stirred at RT for 1 h. The volatiles were removed under reduced pressure and the residue was purified by flash column chromatography to obtain the titled compound as a white solid. MS ($ES^+$): 426.1 $(M+H)^+$. Calc'd for $C_{26}H_{27}N_5O$-425.22.

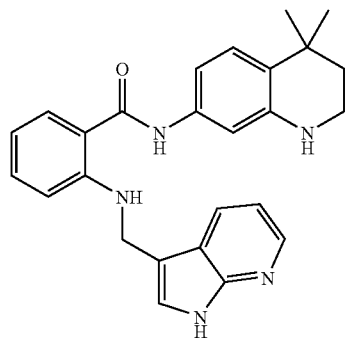

N-(4,4-Dim thyl-1,2,3,4-tetrahydro-quinolin-7-yl)-2-[(1H-pyrrolo[2,3-b]pyridin-3-ylmethyl)-amino]-benzamid A mixture of 2-[(1H-pyrrolo[2,3-b]pyridin-3-ylmethyl)-amino]-benzoic acid (Step A, Example 113) (200 mg), 4,4-dimethyl-1,2,3,4-tetrahydro-quinolin-7-ylamine (132 mg), TBTU (265 mg), and DIEA (0.14 mL) in DMF was stirred at RT under $N_2$ atmosphere for 16 h. The mixture was diluted with EtOAc (10 mL) and extracted with water (2×15 mL). The organic layer was dried over $Na_2SO_4$ and the crude material was purified with flash chromatography ($SiO_2$, 5% $MeOH/CH_2Cl_2$) to give the titled compound as a tan solid. MS ($ES^+$): 426.0 $(M+H)^+$. Calc'd for $C_{26}H_{27}N_5O$-425.53.

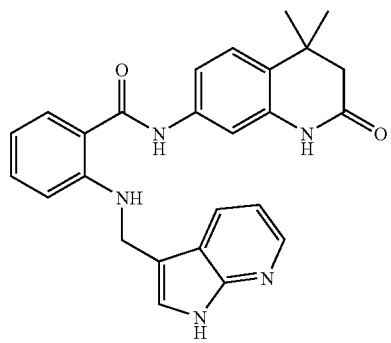

N-(4,4-Dimethyl-2-oxo-1,2,3,4-tetrahydro-quinolin-7-yl)-2[(1H-pyrrolo[2,3-b]pyridin-3-ylmethyl)-amino]-benzamide A mixture of 2-[(1H-pyrrolo[2,3-b]pyridin-3-ylmethyl)-amino]-benzoic acid (Step A, Example 113) (200 mg), 7-amino-4,4-dimethyl-3,4-dihydro-1H-quinolin-2-one (143 mg), TBTU (265 mg), and DIEA (0.14 mL) in DMF (2 mL) was stirred at RT under $N_2$ atmosphere for 16 h. The mixture was diluted with EtOAc (10 mL) and extracted with water (2×15 mL). The organic layer was dried over $Na_2SO_4$ and the crude material was purified by flash chromatography ($SiO_2$, 5% $MeOH/CH_2Cl_2$) to afford the titled compound as a white solid. MS ($ES^+$): 440.0 $(M+H)^+$. Calc'd for $C_{26}H_{25}N_5O2$-439.52.

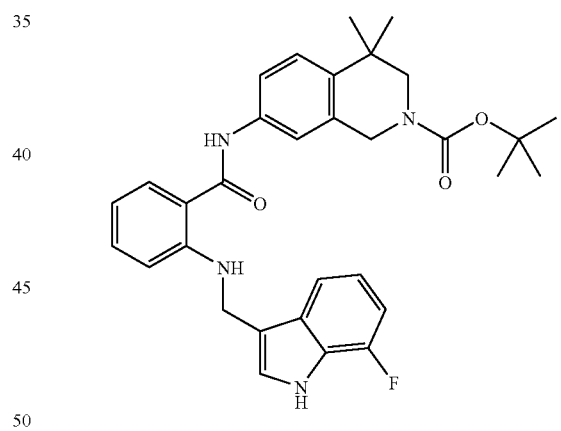

1,1-Dimethylethyl 7-(((2-(((7-fluoro-1H-indol-3-yl)methyl)amino)phenyl)carbonyl)amino)-4,4-dimethyl-3,4-dihydro-2(1H)-isoguinolinecarboxylate Step A: Preparation —2-[(7-fluoro-1H-indol-3-ylmethyl)-amino]-benzoic acid A mixture of 7-fluoro-1H-indole-3-carbaldehyde (200 mg, 1.23 mmol), 2-amino-benzoic acid (168 mg, 1.23 mmol) and p-toluenesulfonic acid (20 mg, 10% W/W) was heated a reflux in toluene (5 mL) for 4 h. The mixture was cooled to RT and diluted with $CH_2Cl_2$. $NaBH_4$ (51.4 mg) was added followed by MeOH (2 mL). The mixture was stirred for 1 h. The reaction mixture was diluted with EtOAc (10 mL) and extracted with water (2×10 mL). The organic layer was dried over Na₂SO₄ and concentrated in vacuo affording the titled compound as a light yellow solid. ESI MS: (M−1)=283. Calc'd for $C_{16}H_{13}FN_2O_2$-284.29.

Step B: Preparation —7-{2-[(7-fluoro-1H-indol-3-ylmethyl)-amino]-benzoylamino}-4,4-dimethyl-3,4-dihydro-1H-isoquinoline-2-carboxylic acid tert-butyl ester A mixture of 2-[(7-fluoro-1H-indol-3-ylmethyl)-amino]-benzoic acid (Step A, 200 mg, 0.70 mmol), 7-amino-4,4-dimethyl-3,4-dihydro-1H-isoquinoline-2-carboxylic acid tert-butyl ester (194 mg, 0.70 mmol), TBTU (247 mg, 0.80 mmol), and DIEA (0.25 mL, 1.4 mmol) in CH₂Cl₂ (5 mL) was stirred at RT under N₂ atmosphere for 16 h. The mixture was diluted with CH₂Cl₂ (5 mL) and extracted with water (2×10 mL). The crude material was purified with flash chromatography (SiO₂, 15% EtOAc/hexane) to give a yellow solid. MS (ES⁺) 543.1. (M+H)⁺. Calc'd for $C_{32}H_{35}FN_4O_3$-542.24.

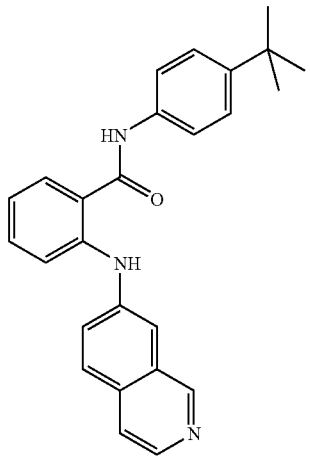

N-(4-tert-Butyl-phenyl)-2-(isoquinolin-7-ylamino)-benzamide

Step A: Preparation of 2-(isoquinolin-7-ylamino)-benzoic acid ethyl ester

A mixture of 2-bromo-benzoic acid ethyl ester (458 mg, 2.0 mmol), 7-aminoisoquinoline (144 mg, 1.0 mmol), Pd(OAc)₂ (11 mg), BINAP (30 mg) and K₂CO₃ (414 mg) in 1 mL of toluene was stirred in a sealed tube for 16 h at 105° C. The reaction was cooled to RT, diluted with 20 mL of CH₂Cl₂, filtered through Celite®, concentrated, and purified by flash column chromatography to obtain the titled compound as an oil. MS (ES⁺): 293.3 (M+H)⁺. Calc'd for $C_{18}H_{16}N_2O_2$-292.

Step B: Preparation of N-(4-tert-butyl-phenyl)-2-(isoquinolin-7-ylamino)-benzamide A mixture of 2-(isoquinolin-7-ylamino)-benzoic acid ethyl ester (Step A, 155 mg, 0.53 mmol) and LiOH monohydrate (67 mg, 1.6 mmol) in a mixed solvent of MeOH (1 mL), water (1 mL) and THF (1 mL) was stirred for 14 h at RT. The resulting mixture was concentrated to dryness to give the corresponding acid lithium salt as a white solid.

A mixture of the lithium salt, 4-t-butylaniline (149 mg, 1.0 mmol), TBTU (176 mg, 0.55 mmol), and DIEA (0.04 mL) in 1 mL of DMF was stirred at RT for 16 h. The mixture was diluted with CH₂Cl₂, the organic layer was washed with water, brine, dried with MgSO₄, filtered and condensed. The residue was purified by flash column chromatography (0 to 30% of EtOAc in CH₂Cl₂), to obtain the titled compound as a white solid. MS (ES⁺): 396.1 (M+H)⁺. Calc'd for $C_{26}H_{25}N_3O$-395.20.

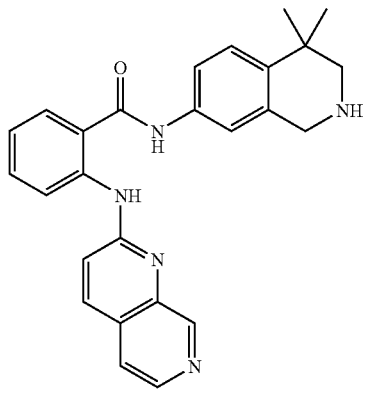

N-(4,4-Dimethyl-1,2,3,4-tetrahydro-isoquinolin-7-yl)-2-([1,7]naphthyridin-2-ylamino)-benzamide Step A: Preparation of 7-(2-amino-benzoylamino)-4,4-dimethyl-3,4-dihydro-1H-isoquinoline-2-carboxylic acid tert-butyl ester A mixture of 7-amino-4,4-dimethyl-3,4-dihydro-1H-isoquinoline-2-carboxylic acid tert-butyl ester (4.0 g, 14.60 mmol), 2-amino-benzoic acid (2.0 g, 14.60 mmol), TBTU (5.2 g, 16.06 mmol) and DIEA (2.7 mL, 16.06 mmol) in DMF (5 mL) was heated (50° C.) for 12 h in a sealed tube. The mixture was diluted with EtOAc and water. The aqueous layer extracted with EtOAc. The combined organic layers were dried over Na₂SO₄, filtered and concentrated in vacuo. The crude material was purified by flash chromatography (SiO₂, 20% EtOAc/hexane) to afford a pinkish solid. MS (ES⁺): 396.0 (M+H)⁺. Calc'd for $C_{23}H_{29}N_3O_3$-395.49.

Step B: Preparation of 4,4-dimethyl-7-[2-([1,7]naphthyridin-2-ylamino)-benzoylamino]-3,4-dihydro-1H-isoquinoline-2-carboxylic acid tert-butyl ester A mixture of 7-(2-amino-benzoylamino)-4,4-dimethyl-3,4-dihydro-1H-isoquinoline-2-carboxylic acid tert-butyl ester (Step A, 303 mg, 0.77 mmol), 2-chloro-[1,7]naphthyridine (126 mg, 0.77 mmol), Pd₂(dba)₃ (7.1 mg, 0.008 mmol), 2-dicyclohexyl phosphino-2'-(N-N-dimethyamino) biphenyl (8 mg, 0.02 mmol), and LiN(TMS)₂ (1 M solution in THF, 2.3 mL) was heated at 80° C. for 12 h. The mixture was concentrated in vacuo and the crude material was purified with flash chromatography (SiO₂, 5% MeOH/CH₂Cl₂) to obtain the titled compound. MS (ES⁺): 524.0 (M+H)⁺. Calc'd for $C_{31}H_{33}N_5O_3$-523.63.

Step C: Preparation of N-(4,4-dimethyl-1,2,3,4-tetrahydro-isoquinolin-7-yl)-2-([1,7]naphthyridin-2-ylamino)-benzamide)

To a solution of 4,4-dimethyl-7-[2-([1,7]naphthyridin-2-ylamino)-benzoylamino]-3,4-dihydro-1H-isoquinoline-2-carboxylic acid tert-butyl ester (Step B, 200 mg, 0.38 mmol) in EtOAC (2 mL) was added concentrated HCl in EtOAc (5 mL). The mixture was stirred for 5 h at RT under $N_2$ atmosphere. The solid was filtered off and dissolved in water. The aqueous solution was basified to pH 11-14 using 5N NaOH. The solution was extracted with EtOAc, and the organic layer was dried over $Na_2SO_4$. The volatiles were removed under reduced pressure and the crude was purified with flash chromatography ($SiO_2$, 5% $MeOH/CH_2Cl_2$) to obtain the desired compound as a white solid. MS (ES$^+$): 424.0 (M+H)$^+$. Calc'd for $C_{26}H_{25}N_5O$-423.51.

Step B: Preparation of N-(4-tert-butyl-phenyl)-2-([1,7]naphthyridin-2-ylamino)-benzamide A mixture of 2-amino-N-(4-tert-butyl-phenyl)-benzamide (Step A, 163 mg, 0.61 mmol), 2-chloro-[1,7]naphthyridine (100 mg, 0.61 mmol), $Pd_2(dba)_3$ (6.0 mg, 0.006 mmol), 2-dicyclohexyl phosphino-2'-(N-N-dimethyamino)biphenyl (6.0 mg, 0.015 mmol), and LiN(TMS)$_2$ (1 M solution in THF, 2.3 mL) was heated at 80° C. for 12 h in a sealed tube. The mixture was concentrated in vacuo and the crude material was purified with flash chromatography ($SiO_2$, 20% EtOAc/hexane) and crystallization from EtOH to give the desired compound. MS (ES$^+$): 397.0 (M+H)$^+$. Calc'd for $C_{25}H_{24}N_4O$-396.48.

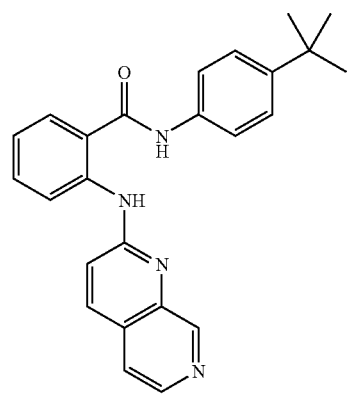

N-(4-tert-Butyl-phenyl)-2-([1,7]naphthyridin-2-ylamino)-benzamide

Step A: Preparation of 2-amino-N-(4-tert-butyl-phenyl)-benzamide

A mixture of 4-tert-butyl-phenylamine (5.8 mL, 36.5 mmol), 2-amino-benzoic acid (5.0 g, 36.5 mmol), TBTU (12.9 g, 40.2 mmol) and DIEA (6.7 mL, 40.2 mmol) in 5 mL of DMF was heated (50° C.) for 12 h in a sealed tube. The mixture was diluted with EtOAc and the aqueous layer was extracted with EtOAc. The combined organic layers were dried over $Na_2SO_4$, filtered and concentrated in vacuo. The crude material was purified by flash chromatography ($SiO_2$, 20% EtOAc/hexane) and crystallized from EtOH:H$_2$O (3:1) to afford a yellow solid. MS (ES$^+$): 269.4. (M+H)$^+$. Calc'd for $C_{17}H_{20}N_2O$-268.35.

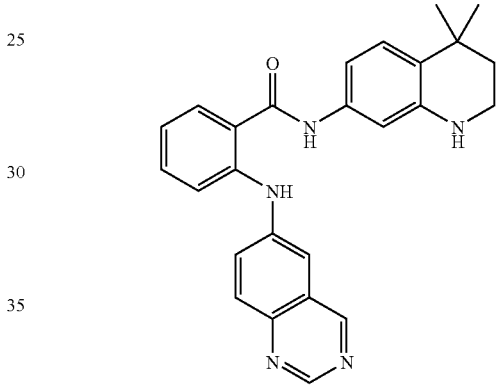

N-(4,4-Dimethyl-1,2,3,4-tetrahydro-quinolin-7-yl)-2-(quinazolin-6-ylamino)-benzamide

Step A: Preparation of 2-(quinazolin-6-ylamino)-benzoic acid ethyl ester

A mixture of 2-bromo-benzoic acid ethyl ester (7.9 g), quinazolin-6-ylamine (5.0 g), Pd(OAc)$_2$ (387 mg), BINAP (714 mg), and $K_2CO_3$ (26 g) in toluene (100 mL was heated at reflux for 12 h. The mixture was diluted with EtOAc and the aqueous layer was extracted with EtOAc. The combined organic layers were dried over $Na_2SO_4$, filtered and concentrated in vacuo. The crude material was purified with flash chromatography ($SiO_2$ 50% EtOAc/hexane) to obtain 2-(quinazolin-6-ylamino)-benzoic acid ethyl ester. MS (ES$^+$): 294.0 (M+H)$^+$. Calc'd for $C_{17}H_{15}N_3O_2$: 293.32.

Step B: Preparation of lithium salt of 2-(quinazolin-6-ylamino)-benzoic acid 2-(Quinazolin-6-ylamino)-benzoic acid ethyl ester (Step A, 2 g, 6.8 mmol), was added to a 1:1 MeOH/water mixture (20 mL). LiOH (856 mg, 20 mmol) was added and the reaction was stirred at RT for 5 h. Solvents were removed in vacuo and the crude was used without further purification.

Step C: Preparation of N-(4,4-dimethyl-1,2,3,4-tetrahydro-quinolin-7-yl)-2-(quinazolin-6-ylamino)-benzamide A mixture of the lithium salt of 2-(quinazolin-6-ylamino)-benzoic acid (Step B, 533 mg, 0.72 mmol), 4,4-dimethyl-1,2,3,4-tetrahydro-quinolin-7-ylamine (127 mg, 0.72 mmol), TBTU (462 mg, 1.44 mmol) and DIEA (0.25 mL, 1.44 mmol) in 3 mL of DMF was submitted to microwave irradiation (80° C., 30 min). Water (5 mL) was added to the mixture, and the resultant precipitate was filtered and dried. The crude material was purified with flash chromatography (SiO$_2$, 50% EtOAc/hexane) to afford a white solid. MS (ES$^+$): 424.0 (M+H)$^+$. Calc'd for C$_{26}$H$_{25}$N$_5$O: 423.51.

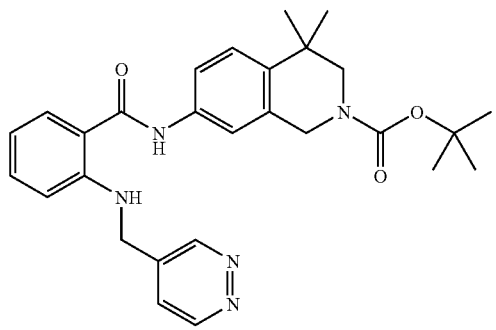

4,4-Dimethyl-7-{2-[(pyridazin-4-ylmethylene)-amino]-benzoylamino}-3,4-dihydro-1H-isoquinoline-2-carboxylic acid tert-butyl ester

Step A: Preparation of 7-(2-amino-benzoylamino)-4,4-dimethyl-3,4-dihydro-1H-isoquinoline-2-carboxylic acid tert-butyl ester A mixture of 7-amino-4,4-dimethyl-3,4-dihydro-1H-isoquinoline-2-carboxylic acid tert-butyl ester (4.0 g, 14.60 mmol), 2-amino-benzoic acid (2.0 g, 14.60 mmol), TBTU (5.2 g, 16.06 mmol) and DIEA (2.7 mL, 16.06 mmol) in 5 mL of DMF was heated (50° C.) for 12 h in a sealed tube. The reaction mixture was diluted with EtOAc and water. The aqueous layer was extracted with EtOAc. The combined organic layers were dried over Na$_2$SO$_4$, filtered and concentrated under vacuum. The crude material was purified by flash chromatography (SiO$_2$, 20% EtOAc/hexane) to afford a pinkish solid. MS (ES$^+$): 396.0 (M+H)$^+$. Calc'd for C$_{23}$H$_{29}$N$_3$O$_3$: 395.49.

Step B: Preparation of 4,4-dimethyl-7-{2-[(pyridazin-4-ylmethylene)-amino]-benzoylamino}-3,4-dihydro-1H-isoquinoline-2-carboxylic acid tert-butyl ester A mixture of 7-(2-amino-benzoylamino)-4,4-dimethyl-3,4-dihydro-1H-isoquinoline-2-carboxylic acid tert-butyl ester (512 mg, 1.3 mmol), pyridazine-4-carbaldehyde (140 mg, 1.3 mmol) and p-toluenesulfonic acid (10 mg) was heated at reflux in toluene (5 mL) for 1 h. The mixture was cooled to RT and diluted with CH$_2$Cl$_2$. NaBH$_4$ (50 mg, 1.3 mmol) was added to the mixture followed by MeOH (2 mL). The mixture was stirred for 1 h. The crude material was purified with flash chromatography (SiO$_2$, 5% MeOH/CH$_2$Cl$_2$) to give a yellow solid. MS (ES$^+$): 488.0 (M+H)$^+$. Calc'd for C$_{28}$H$_{33}$N$_5$O$_3$: 487.59.

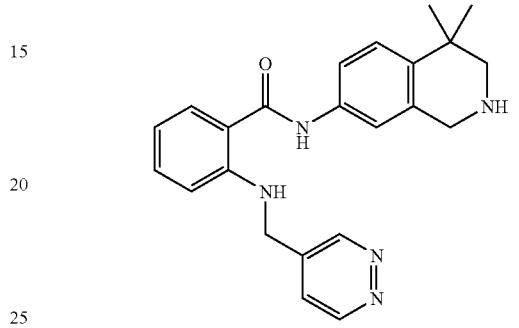

N-(4,4-Dimethyl-1,2,3,4-tetrahydro-isoquinolin-7-yl)-2-[(pyridazin-4-ylmethyl)-amino]-benzamide To a solution of 4,4-dimethyl-7-{2-[(pyridazin-4-ylmethylene)-amino]-benzoylamino}-3,4-dihydro-1H-isoquinoline-2-carboxylic acid tert-butyl ester (Example 121, Step B, 200 mg, 0.41 mmol) in EtOAC (1 mL). Concentrated HCl in EtOAc (2 mL) was added. The reaction was stirred for 5 h under N$_2$ atmosphere at RT. The solid was filtered off and dissolved in water. The aqueous solution was basified to pH 11-14 using 5 N NaOH. The resulting precipitate was filtered, washed with water and dried under vacuum, to obtain the titled compound as a tan solid. MS (ES$^+$): 388.0 (M+H)$^+$. Calc'd for C$_{23}$H$_{25}$N$_5$O: 387.21.

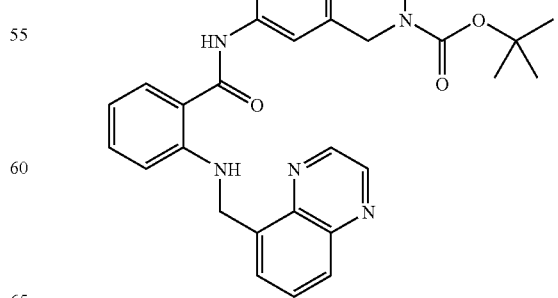

4,4-Dimethyl-7-{2-[(quinoxalin-5-ylmethyl)-amino]-benzoylamino}-3,4-dihydro-1H-isoquinoline-2-carboxylic acid tert-butyl ester Example 123 was synthesized by a method similar to that described in Example 121. MS (ES$^+$): 538.0 (M+H)$^+$. Calc'd for $C_{32}H_{35}N_5O_3$: 537.27.

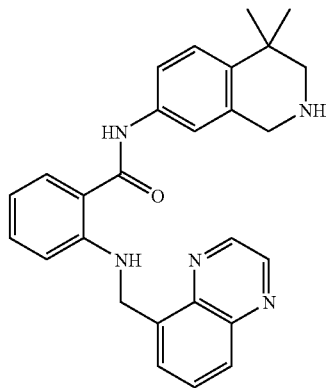

N-(4,4-Dimethyl-1,2,3,4-tetrahydro-isoquinolin-7-yl)-2-[(quinoxalin-5-ylmethyl)-amino]-benzamide Example 124 was synthesized by a method similar to that described in Example 122. MS (ES$^+$): 438.0 (M+H)$^+$. Calc'd for $C_{27}H_{27}N_5O$: 437.54.

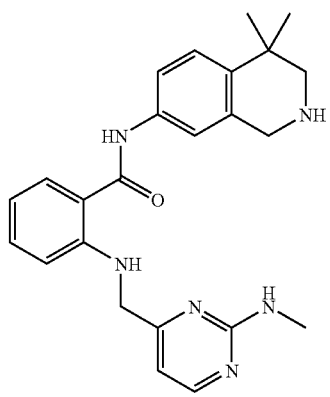

N-(4,4-Dimethyl-1,2,3,4-tetrahydro-isoquinolin-7-yl)-2-[(2-methylamino-pyrimidin-4-ylmethyl)-amino]-benzamide

Step A: Preparation of (4-dimethoxymethyl-pyrimidin-2-yl)-methyl-amine

A mixture of 1,1-dimethoxy-4-dimethylaminobut-3-en-2-one (4.06 g, 22.3 mmol) (Lipinski; J. Het. Chem. (1995), 22, 1723), 1-methylguanidine hydrochloride (2.50 g, 22.3 mmol) and NaOH (0.89 g, 22.3 mmol) in 20 mL of IpOH and was stirred at reflux for 20 h. The mixture was cooled to RT, diluted with MeOH, and the solids were removed by filtration. The filtrate was condensed, and the crude compound was purified by flash column chromatography (5% to 40% of EtOAc in $CH_2Cl_2$). The titled compound was obtained as a light yellowish oil. MS (ES$^+$): 184.2 (M+H)$^+$. Calc'd for $C_8H_{13}N_3O_2$-183.21.

Step B: Preparation of 2-methylamino-pyrimidine-4-carbaldehyde (4-Dimethoxymethyl-pyrimidin-2-yl)-methylamine (Step A, 3.60 g, 19.6 mmol) and 3 N HCl (14.4 mL, 43.2 mmol) were combined and stirred at 48° C. for 17 h. After cooling to RT, 4.3 g of NaHCO$_3$ was added in portions. The mixture was extracted with EtOAc, the combined organic portions were dried over MgSO$_4$, filtered, and condensed to give the titled compound as a yellow solid. MS (ES$^+$): 138.3 (M+H)$^+$. Calc'd for $C_6H_7N_3O$-137.14.

Step C: Preparation of 2-[(2-methylamino-pyrimidin-4-ylmethyl)-amino]-benzoic acid A mixture of anthranilic acid (0.55 g, 4.0 mmol), 2-methylamino-pyrimidine-4-carbaldehyde (Step B, 0.72 g, 5.2 mmol), and p-toluenesulfonic acid mohohydrate (0.025 g, 0.13 mmol) in 20 mL of anhydrous toluene was stirred at reflux for 1 h, and cooled to RT. NaBH$_4$ (0.41 g, 10.8 mmol) was added, and the mixture was stirred at RT for 30 min. The mixture was quenched with MeOH, the volatiles were removed under reduced pressure, and the residue was taken up in water. AcOH was added to bring the pH to 4 and the mixture was extracted with EtOAc. The combined organic portions were washed with brine, dried over MgSO$_4$, filtered, condensed, and the residue was purified by flash column chromatography to give the titled compound. MS (ES$^+$): 259.0 (M+H)$^+$. Calc'd for $C_{13}H_{14}N_4O_2$-258.28

Step D: Preparation of 4,4-dimethyl-7-{2-[(2-methylamino-pyrimidin-4-ylmethyl)-amino]-benzoylamino}-3,4-dihydro-1H-isoquinoline-2-carboxylic acid tert-butyl ester A mixture of 2-[(2-methylamino-pyrimidin-4-ylmethyl)-amino]-benzoic acid (Step C, 0.31 g, 1.20 mmol), 7-amino-4,4-dimethyl-3,4-dihydro-1H-isoquinoline-2-carboxylic acid tert-butyl ester (0.33 g, 1.20 mmol), TBTU (0.43 g, 1.32 mmol), and DIEA (0.31 mL, 1.80 mmol) in 10 mL of DMF was stirred at RT for 2 h. The mixture was partitioned between EtOAc and Na$_2$CO$_3$ (aq). The organic layer was washed with water, brine, dried with MgSO$_4$, filtered, condensed, and the residue was purified by flash column chromatography (0 to 30% of EtOAc in $CH_2Cl_2$). The titled compound was obtained as a light yellowish solid. MS (ES$^+$): 517.4 (M+H)$^+$. Calc'd for $C_{29}H_{36}N_6O_3$-516.63

Step E: Preparation of N-(4,4-dimethyl-1,2,3,4-tetrahydro-isoquinolin-7-yl)-2-[(2-methylamino-pyrimidin-4-ylmethyl)-amino]-benzamide 4,4-Dimethyl-7-{2-[(2-methylamino-pyrimidin-4-ylmethyl)-amino]-benzoylamino}-3,4-dihydro-1H-isoquinoline-2-carboxylic acid tert-butyl ester (Step D, 0.65 g, 1.26 mmol) in 10 mL of 50% of TFA in $CH_2Cl_2$ was stirred at RT for 1 h. The volatiles were removed under reduced pressure, the residue was purified by flash column chromatography, and the titled compound was obtained as a white solid. MS (ES$^+$): 417.1 (M+H)$^+$. Calc'd for $C_{24}H_{28}N_6O$-416.52.

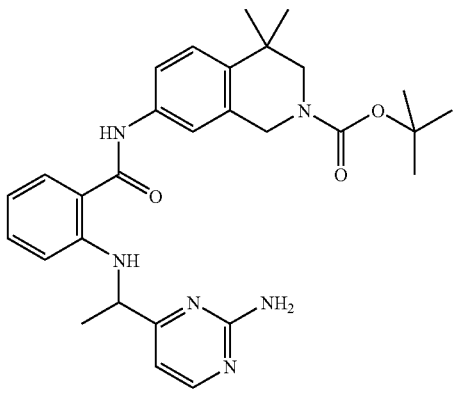

tert-Butyl 7-{2-[1-(2-amino-pyrimidin-4-yl)-ethylamino]-benzoylamino}-4,4-dimethyl-3,4-dihydro-1H-isoquinoline-2-carboxylate Step A: Preparation of 4-(1,1-dimethoxy-ethyl)-pyrimidin-2-ylamine To guanidine hydrochloride salt (15 g, 156.68 mmol) was added sodium ethoxide, 21% wt in EtOH (59 mL, 156.68 mmol). After stirring for 5 min, 1-dimethylamino-4,4-dimethoxy-pent-1-en-3-one (Lipinski; J. Het. Chem., 22:1723 (1995)) (29.30 g, 156.68 mmol) in EtOH (50 mL) was added. The mixture was heated at 80° C. under $N_2$ for 20 h, then cooled to RT. Solvent was evaporated in vacuo and the residue was re-dissolved in hot EtOAc (200 mL). The undissolved solid was separated by filtration and the solvent was evaporated in vacuo to give a pale yellow solid. MS m/z:184.3(M+H). Calc'd for $C_8H_{14}N_3O_2$: 184.21.

Step B: Preparation of 1-(2-amino-pyrimidin-4-yl)-ethanone

To 4-(1,1-dimethoxy-ethyl)-pyrimidin-2-ylamine (Step A, 15 g, 81.87 mmol) was added HCOOH (70.0 mL). The resulting mixture was stirred at RT under argon for 3 h. The mixture was evaporated to dryness. The solid was recrystallized from EtOH to give a brown solid. MS m/z:138.2 (M+H). Calc'd for $C_6H_8N_3O$: 138.14.

Step C: Preparation of tert-Butyl 7-{2-[1-(2-Amino-pyrimidin-4-yl)-ethylamino]-benzoylamino}-4,4-dimethyl-3,4-dihydro-1H-isoquinoline-2-carboxylate To a solution of 1-(2-amino-pyrimidin-4-yl)-ethanone (Step B, 200 mg, 1.46 mmol) in toluene (15 mL) was added, 7-(2-amino-benzoylamino)-4,4-dimethyl-3,4-dihydro-1H-isoquinoline-2-carboxylic acid tert-butyl ester (Example 15, Step A)(288 mg, 0.73 mmol), and HOAc (3 drops). The resulting mixture was heated at 95° C. under $N_2$ for 20 h. The reaction was cooled to RT and NaBH(OAc)$_3$ (620 mg, 2.92 mmol) was added and reheated for 3 h. The reaction was cooled to RT, quenched with Na$_2$CO$_3$ solution (2 M, 5 mL), solvent was evaporated in vacuo. The residue was extracted with CHCl$_3$. The organic layer was washed with saturated NaHCO$_3$, water, brine, dried over MgSO$_4$, and evaporated in vacuo. The crude solid was purified by chromatography on silica gel. Elution with CH$_2$Cl$_2$:MeOH (95:5) gave THE final compound. MS m/z: 517.3 (M+H). Calc'd. for $C_{29}H_{37}N_6O_3$-517.63.

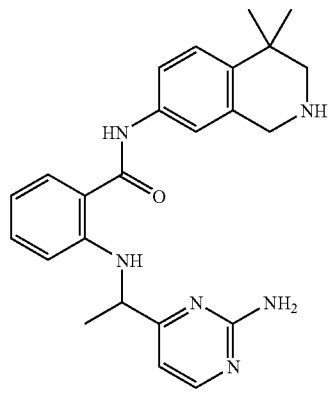

2-[1-(2-Amino-pyrimidin-4-yl)-ethylamino]-N-(4,4-dimethyl-1,2,3,4-tetrahydro-isoquinolin-7-yl)-benzamide To a solution of 7-{2-[1-(2-amino-pyrimidin-4-yl)-ethylamino]-benzoylamino}-4,4-dimethyl-3,4-dihydro-1H-isoquinoline-2-carboxylic acid tert-butyl ester (Example 125) (80 mg, 0.154 mmol) in CH$_2$Cl$_2$ (3 mL) was added TFA (2 mL). The resulting mixture was stirred at RT for 18 h and basified with 5 N NaOH and extracted with CH$_2$Cl$_2$ (2×15 mL). The combined organic layers were washed with saturated NaHCO$_3$, water, brine, dried over MgSO$_4$, and evaporated in vacuo to give the product. MS m/z: 417.5 (M+H). Calc'd. for $C_{24}H_{29}N_6O$-417.51.

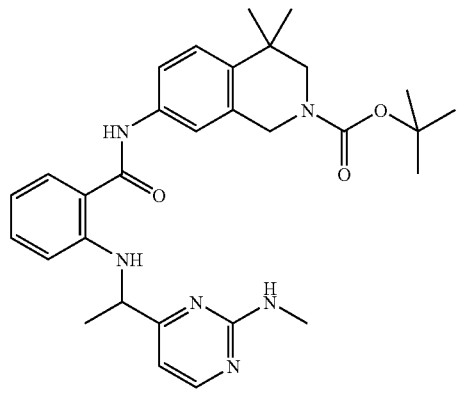

tert-Butyl 4,4-dimethyl-7-{2-[1-(2-methylamino-pyrimidin-4-yl)-ethylamino]-benzoylamino}-3,4-dihydro-1H-isoquinoline-2-carboxylate Step A: Preparation of 1-(2-methylamino-pyrimidin-4-yl)-ethanone The titled compound was synthesized by methods similar to that described in Example 126, Steps A and B. MS m/z:152.3(M+H). Calc'd for $C_7H_{10}N_3O$: 152.17.

Step B: Preparation of 2-[1-(2-methylamino-pyrimidin-4-yl)-ethylamino]-benzoic acid To a solution of 1-(2-methylamino-pyrimidin-4-yl)-ethanone (Step A, 1.0 g, 6.61 mmol) in dry toluene (40 mL) was added anthranilic acid (635 mg, 4.63 mmol) and TsOH (25 mg, 0.132 mmol). The resulting mixture was heated at 90° C. for 20 h, then cooled to RT. NaBH$_4$ (500 mg, 13.23 mmol) was added and the reaction was stirred for 5 h. The reaction was quenched with MeOH and evaporated in vacuo. The crude solid was purified by chromatography on silica gel. Elution with CH$_2$Cl$_2$:MeOH mixture (95:5) gave final compound. MS m/z: 273.3 (M+H). Calc'd. for C$_{14}$H$_{17}$N$_4$O$_2$-273.3.

Step C: Preparation of tert-butyl-4,4-dimethyl-7-{2-[1-(2-methylamino-pyrimidin-4-yl)-ethylamino]-benzoylamino}-3,4-dihydro-1H-isoquinoline-2-carboxylate To a solution of 2-[1-(2-methylamino-pyrimidin-4-yl)-ethylamino]-benzoic acid (Step B, 800 mg, 2.94 mmol) in CH$_2$Cl$_2$ (40 mL) was added 7-amino-4,4-dimethyl-3,4-dihydro-1H-isoquinoline-2-carboxylic acid tert-butylester (812 mg, 2.94 mmol), TBTU (1.0 g, 3.23 mmol), and DIEA (1.5 mL, 8.81 mmol). The reaction was stirred at RT under N$_2$ for 20 h. The reaction was quenched with sat. NH$_4$Cl, washed with water, brine, dried over MgSO$_4$, and evaporated in vacuo. The crude solid was purified by chromatography on silica gel. Elution with Hexanes:acetone mixture (80:20) gave final compound. MS m/z: 531.2 (M+H). Calc'd. for C$_{30}$H$_{37}$N$_6$O$_3$-531.66.

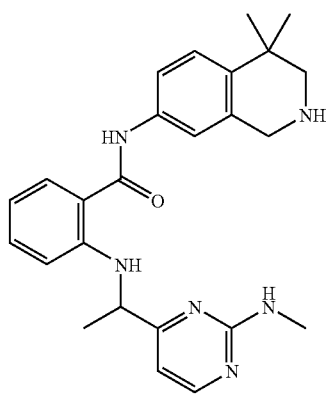

N-(4,4-Dimethyl-1,2,3,4-tetrahydro-isoquinolin-7-yl)-2-[1-(2-methylamino-pyrimidin-4-yl)-ethylamino]-benzamide In a manner similar to that described in Example 127, to a solution of tert-butyl 4,4-dimethyl-7-{2-[1-(2-methylamino-pyrimidin-4-yl)-ethylamino]-benzoylamino}-3,4-dihydro-1H-isoquinoline-2-carboxylate (250 mg, 0.471 mmol) in CH$_2$Cl$_2$ (5 mL) was added TFA (3 mL) to give the final product. MS m/z: 431.3 (M+H). Calc'd. for C$_{25}$H$_{31}$N$_6$O-431.55.

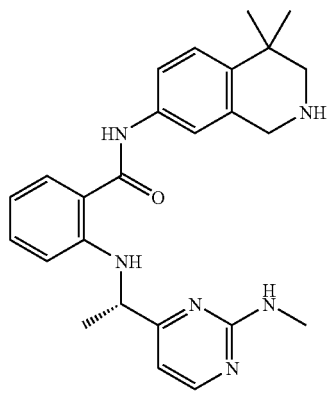

(S)—N-(4,4-Dimethyl-1,2,3,4-tetrahydro-isoquinolin-7-yl)-2-[1-(2-methylamino-pyrimidin-4-yl)-ethylamino]-benzamide N-(4,4-Dimethyl-1,2,3,4-tetrahydro-isoquinolin-7-yl)-2-[1-(2-methylamino-pyrimidin-4-yl)-ethylamino]-benzamide (190 mg, 0.44 mmol) was separated on a chiral column (Chiralcel AD, 250×4.6 (mm) 10u, n-Hexane/i-PrOH/0.2% DEA (70:30), 1 mL/min). The (S) enantiomer was isolated. MS m/z: 431.3 (M+H). Calc'd. for C$_{25}$H$_{31}$N$_6$O-431.55.

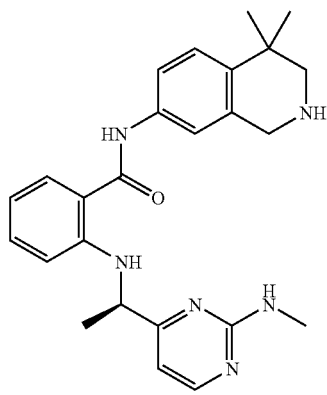

(R)—N-(4,4-Dimethyl-1,2,3,4-tetrahydro-isoquinolin-7-yl)-2-[1-(2-methylamino-pyrimidin-4-yl)-ethylamino]-benzamide In a manner similar to that described in Example 130, the (R) isomer was obtained. MS m/z: 431.3 (M+H). Calc'd. for $C_{25}H_{31}N_6O$-431.55.

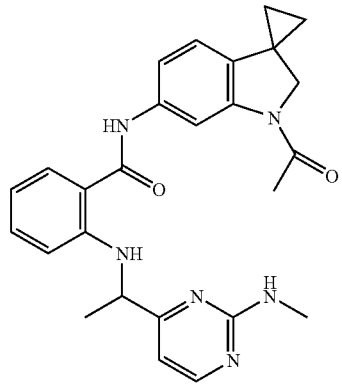

N-(1-Acetyl-1',2'-dihydrospiro[cyclopropane-1,3'-[3H]indol]-6'-yl)-2-[[(1R)-1-[2-(methylamino)-4-pyrimidinyl]ethyl]amino]-benzamide

Step A: Preparation of 1,2-dihydro-3-spiro-1'-cyclopropy-1H-indole

A solution of 3-(2-bromo-ethyl)-1H-indole (5 g) in anhydrous $CH_3CN$ (100 mL) was suspended with oven dried $K_2CO_3$ (20 g) and heated to reflux for 10 h. After cooling to RT, the mixture was filtered and the filter cake was washed with EtOH (50 mL). The combined filtrate was treated with $NaBH_4$ (300 mg) and stirred for 3 h at RT. Solvents were removed in vacuo and the residue was partitioned between water (160 mL) and EtOAc (60 mL). The organic layer was extracted with aqueous HCl (0.5N, 30 mL×2) and the acid layer was basified with $NH_4OH$ (aq. Conc.) then extracted with EtOAc. The organic phase was washed with brine, dried over $Na_2SO_4$ and concentrated to give a colorless thin oil as the desired compound. MS (ESI, pos. ion) m/z: 146 (M+1).

Step B: Preparation of 6-nitro-1,2-dihydro-3-spiro-1'-cyclopropyl-1H-indole 1',2'-Dihydrospiro(cyclopropane-1,3'-[3H]indole) (Step A, 1.8 g 12.4 mmol) was added dropwise over a period of 20 min to a cooled (−5 to −10° C.) solution of $NaNO_3$ (1.3 g) in $H_2SO_4$ (conc., 30 mL). After the addition, the reaction was stirred for another 40 min, poured onto crushed ice (200 g) and the resulting mixture was basified with $NH_4OH$ (aq., conc.) with cooling. The basified mixture was extracted with EtOAc twice and the organic layer was washed with brine then dried over $Na_2SO_4$. After concentration in vacuo, a dark gray solid was received as the desired compound. MS (ESI, pos. ion) m/z: 191 (M+1).

Step C: Preparation of 1-acetyl-6-nitro-1,2-dihydro-3-spiro-1'-cyclopropyl-1H-indole A solution of 6-nitro-1,2-dihydro-3-spiro-1'-cyclopropyl-1H-indole (Step B, 1.3 g) in $CH_2Cl_2$ (100 mL) was suspended with $NaHCO_3$ (5 g), and acetyl chloride (720 mg) was added dropwise with vigorous stirring. After the addition the reaction was stirred for 1 h. The mixture was filtered and the filtrate was concentrated in vacuo then purified via flash chromatography on silica (EtOAc:hexanes=3:1 to 4:1) to give the title compound. MS (ESI, pos. ion) m/z: 233 (M+1).

Step D: Preparation of 1-acetyl-6-amino-1,2-dihydro-3-spiro-1'-cyclopropyl-1H-indole Ethyl 1-acetyl-6-nitro-1,2-dihydro-3-spiro-1'-cyclopropyl-1H-indole (Step C, 2 g) was dissolved in EtOH (200 mL), suspended with Pd/C (10%, 100 mg) and equipped with a balloon filled with $H_2$. The hydrogenation was finished in 1.5 h. The mixture was filtered through a layer of Celite®. The filtrate was concentrated in vacuo to give a white solid as the desired compound. MS (ESI, pos. ion) m/z: 203 (M+1).

Step E: Preparation of N-(1-acetyl-1',2'-dihydrospiro[cyclopropane-1,3'-[3H]indol]-6'-yl)-2-[[(1R)-1-[2-(methylamino)-4-pyrimidinyl]ethyl]amino]-benzamide In a manner similar to that described in Example 128, Steps B and C, a solution of 2-[1-(2-methylamino-pyrimidin-4-yl)-ethylamino]-benzoic acid (450 mg, 1.65 mmol), 1-acetyl-2,3-dihydro-3-spiro-cyclopropyl-6-amino-1H-indole (Step D, 334 mg, 1.65 mmol), TBTU (584 mg, 1.82 mmol), and DIEA (1.2 mL, 6.61 mmol) in $CH_2Cl_2$ (40 mL) was stirred at RT to give the titled compound. MS m/z: 457.3 (M+H). Calc'd. for $C_{26}H_{28}N_6O_2$-456.55.

Although the pharmacological properties of the compounds of Formula I-I' vary with structural change, in general, activity possessed by compounds of Formulas I-I' may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of KDR at doses less than 50 μM.

BIOLOGICAL EVALUATION

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+ antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of $3\times10^5$ cells/mL. Another cell count is performed to confirm the cell concentration. The cells are diluted to $3\times10^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+10% FBS+antibiotics (400× dilution). Medium containing 0.25% DMSO is also prepared for the 0 µM compound sample. At the 22 h timepoint, the medium is removed from the cells, and 100 µL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

The compounds of Examples 1-13, 104-115, 117, 120-122, 124-126, and 129-132 inhibited VEGF-stimulated HUVEC proliferation at a level below 1 µM. In addition, compounds of Examples 1-2,4-7, 9, 11-12, 104-106, 109-112, 114-115, 117, 120, 122, 125, 127, 129 and 131 inhibited VEGF-stimulated HUVEC proliferation at a level below 100 nM.

Angiogenesis Model

To determine the effects of the present compounds on angiogenesis in vivo, selective compounds are tested in the rat corneal neovascularization micropocket model or the angiogenesis assay of Passaniti, Lab. Invest., 67:519-528 (1992).

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+ 5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After twenty-four hours in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A. G. Heinz, Irvine Calif.) mounted on a Nikon SMZ-U stereo microscope (A. G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

GENERAL FORMULATIONS 0.1% BSA in PBS vehicle: 0.025 g of BSA was added to 25.0 mL of sterile 1× phosphate buffered saline, gently shaken until fully dissolved, and filtered at 0.2 µm. Individual 1.0 mL samples were aliquoted into 25 single use vials, and stored at −20° C. until use. For the rHu-bFGF disks, a vial of this 0.1% BSA solution was allowed to thaw at room temperature. Once thawed, 10 µl of a 100 mM stock solution of DTT was added to the 1 mL BSA vial to yield a final concentration of 1 mM DTT in 0.1% BSA.

rHu-VEGF Dilutions: Prior to the disk implant surgery, 23.8 µl of the 0.1% BSA vehicle above was added to a 10 µg rHu-VEGF lyophilized vial yielding a final concentration of 10 µM.

rHu-bFGF: Stock concentration of 180 ng/µl: R&D rHu-bFGF: Added 139 µl of the appropriate vehicle above to the 25 µg vial lyophilized vial. 13.3 µl of the [180 ng/µl] stock vial and added 26.6 µl of vehicle to yield a final concentration of 3.75 µM concentration.

Nitro-cellulose disk preparation: The tip of a 20-gauge needle was cut off square and beveled with emery paper to create a punch. This tip was then used to cut out ≈0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

In the rat micropocket assay, preferred compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention are active at doses less than 150 mpk.

Rat Adjuvant Arthritis Model

The rat adjuvant arthritis model (Pearson, Proc. Soc. Exp. Biol. 91, 95-101 (1956)) is used to test the anti-arthritic activity of compounds of the formula 1, or salts thereof. Adjuvant Arthritis can be treated using two different dosing schedules: either (i) starting time of immunization with adjuvant (prophylactic dosing); or from day 15 when the arthritic response is already established (therapeutic dosing). Preferably a therapeutic dosing schedule is used.

Rat Carrageenan-induced Analgesia Test

The rat carrageenan analgesia test was performed with materials, reagents and procedures essentially as described by Hargreaves, et al., (Pain, 32, 77 (1988)). Male Sprague-Dawley rats were treated as previously described for the Carrageenan Foot Pad Edema test. 3 h after the injection of the carrageenan, the rats were placed in a special plexiglass container with a transparent floor having a high intensity 1 amp as a radiant heat source, positionable under the floor. After an initial 20 min period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined.

Formulations

Also embraced within this invention is a class of pharmaceutical compositions comprising the active compounds of Formulas I-I' in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

No unacceptable toxological effects are expected when compounds of the present invention are administered in accordance with the present invention.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of Formula I

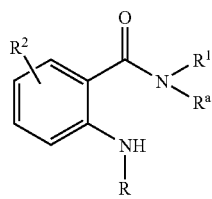

wherein R is

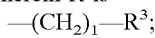—(CH$_2$)$_1$—R$^3$;

wherein R$^1$ is selected from 1,2-dihydroquinolyl, 1,2,3,4-tetrahydroisoquinolyl, 2,3-dihydro-1H-indolyl, and 1,4-benzodioxanyl; wherein R$^1$ is unsubstituted or substituted with one or more substituents selected from bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmetliyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylearbonyl, Boc, piperidin-1-ylmethylcarbonyl, 4-methylpiperazin-1-ykarbonylethyl, methoxycarbonyl, aminomethylcarbonyl, dinaethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-naethyl-(1,2,3,6-tetrahydropyridyl), imidazolyl, morpholinyl, 4-trifluormethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoroxnethyl)-1-hydroxyrnethyl, 1,1-di(trifluoromethyl)-1-(peridinylethoxy)methyl, 1,1-di(trifluoromethyl)-1-(methoxyethoxyethoxy)methyl, 1-hydroxyethy, 2-hydroxyethyl, trifluoromethoxy, 1-aminoethyl, 2-amninoethyl, 2-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein R$^2$ is one or more substituents independently selected from

H,
halo,
hydroxy,
amino,
C$_{1-6}$-alkyl,
C$_{1-6}$-haloalkyl,
C$_{1-6}$-alkoxy,
C$_{1-2}$-alkylamino,
aminosulfonyl,
C$_{3-6}$-cycloalkyl,
cyano,
C$_{1-2}$-hydroxyalkyl,
nitro,
C$_{2-3}$-alkenyl,
C$_{2-3}$-alkynyl,
C$_{1-6}$-haloalkoxy,
C$_{1-6}$-carboxyalkyl,
4-6-membered heterocyclyl-C$_{1-6}$-alkylamino,
unsubstituted or substituted phenyl and
unsubstituted or substituted 4-6 membered heterocyclyl;

wherein R$^3$ is substituted or unsubstituted 5-6 membered heterocyclyl; wherein substituted R$^3$ is substituted with one or more substituents independently selected from halo, —OR$^4$, —SR$^4$, —SO$_2$R$^4$, —CO$_2$R$^4$, —CONR$^4$R$^4$, —COR$^4$, NR$^4$R$^4$, —SO$_2$NR$^4$R$^4$, —NR$^4$C(O)OR$^4$, —NR$^4$C(O)R$^4$, cycloalkyl, optionally substituted 5-6 membered heterocyclyl, optionally substituted phenyl, lower alkyl substituted with 1(2, cyano, nitro, lower alkenyl and lower alkynyl;

wherein R$^4$ independently selected from H, lower alkyl, optionally substituted phenyl, optionally substituted 4-6 membered heterocyclyl, optionally substituted C$_3$-C$_6$cycloalkyl, phenyl-C$_{1-6}$-alkyl, optionally substituted 4-6 membered heterocyclyl-C$_{1-6}$-alkyl, and lower haloalkyl;

wherein R$^5$ is selected from H, C$_{1-3}$-alkyl, optionally substituted phenyl, optionally substituted phenyl-C$_{1-3}$-alkyl, 4-6 membered heterocyclyl, optionally substituted 4-6 membered heterocyclyl-C$_1$-C$_3$-alkyl, C$_{1-3}$alkoxy-C$_{1-2}$-alkyl and C$_{1-3}$-alkoxy-C$_{1-3}$-alkoxy-C$_{1-3}$-alkyl;

wherein R$^a$ is selected from H and C$_{1-2}$-alkyl; and wherein R$^b$ and R$^c$ are independently selected from H and C$_{1-2}$-haloalkyl;

and pharmaceutically acceptable salts thereof.

2. A compound of Formula I'

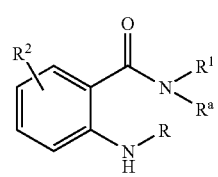

wherein R is

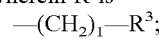—(CH$_2$)$_1$—R$^3$;

wherein R$^1$ is selected from 1,2-dihydroquinolyl, 1,2,3,4-tetrahydroisoquinolyl, 2,3-dihydro-1H-indolyl, and 1,4-benzodioxanyl; wherein R$^1$ is unsubstituted or substituted with one or more substituents selected from bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonyl-ethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperdin-4-ylmethoxy, piperdin-4-ylmethoxy, 1-methylpiperdin-4-yloxy, isopropoxy, methoxy and ethoxy;

wherein $R^2$ is one or more substituents independently selected from
H,
halo,
hydroxy,
amino,
$C_{1-6}$-alkyl,
$C_{1-6}$-haloalkyl,
$C_{1-6}$-alkoxy,
$C_{1-2}$-alkylamino,
aminosulfonyl,
$C_{3-6}$-cycloalkyl,
cyano,
$C_{1-2}$-hydroxyalkyl
nitro,
$C_{2-3}$-alkenyl,
$C_{2-3}$-alkynyl,
$C_{1-6}$-haloalkoxy,
$C_{1-6}$-carboxyalkyl,
4-6-membered heterocyclyl-$C_{1-6}$-alkylamino,
unsubstituted or substituted phenyl and
unsubstituted or substituted 4-6 membered heterocyclyl;

wherein $R^3$ is substituted or unsubstituted 5-6 membered heterocyclyl; wherein substituted $R^3$ is substituted with one or more substituents independently selected from halo, —$OR^4$, —$SR^4$, —$SO_2R^4$, —$CO_2R^4$, —$CONR^4R^4$, —$COR^4$, —$NR^4R^4$, —$SO_2NR^4R^4$, —$NR^4C(O)OR^4$, —$NR^4C(O)R^4$, cycloalkyl, optionally substituted 5-6 membered heterocyclyl, optionally substituted phenyl, lower alkyl substituted with $R^6$, cyano, nitro, lower alkenyl and lower alkynyl;

wherein $R^4$ is independently selected from H, lower alkyl, optionally substituted phenyl, optionally substituted 4-6 membered heterocyclyl, optionally substituted $C_3$-$C_6$ cycloalkyl, phenyl-$C_{1-6}$-alkyl, optionally substituted 4-6 membered heterocyclyl-$C_{1-6}$-alkyl, and lower haloalkyl;

wherein $R^5$ is selected from H, $C_{1-3}$-alkyl, optionally substituted phenyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$alkyl and $C_{1-3}$-alkoxy-$C_{1-3}$-alkoxy-$C_{1-3}$-alkyl;

wherein $R^6$ is selected from H, halo, hydroxy, amino, $C_{1-6}$-alkoxy, $C_{1-2}$-alkylamino, aminosulfonyl, $C_{3-6}$-cycloalkyl, cyano, nitro, $C_{1-6}$-haloalkoxy, carboxy, 4-6-membered heterocyclyl-$C_{1-6}$-alkylamino, unsubstituted or substituted phenyl and unsubstituted or substituted 4-6 membered heterocyclyl;

wherein $R^a$ is selected from H and $C_{1-2}$-alkyl; and
wherein $R^b$ and $R^c$ are independently selected from H and $C_{1-2}$-haloalkyl;
and pharmaceutically acceptable salts thereof.

3. Compound of claim 2 wherein $R^1$ is selected from 4,4-dimethyl-1,2,3,4-tetrahydro-isoquinol-7-yl, 2-acetyl-4,4-dimethyl-1,2,3,4-tetrahydro-isoquinol-7-yl, 2,3-dihydro-1H-indolyl, 3,3-dimethyl-2,3-dihydro-1H-indol-6-yl, 1-ethyl-3,3-dimethyl-2,3-dihydro-1H-indol-6-yl, and 1-acetyl-3,3-dimethyl-2,3-dihydro-1H-indol-6-yl; and pharmaceutically acceptable salts thereof.

4. Compound of claim 3 wherein $R^1$ is 3,3-dimethyl-2,3-dihydro-1H-indol-6-yl; and pharmaceutically acceptable salts thereof.

5. Compound of claim 3 wherein $R^1$ is 4,4-dimethyl-1,2,3,4-tetrahydro-isoquinol-7-yl; and pharmaceutically acceptable salts thereof.

6. Compound of claim 2 wherein $R^2$ is selected from H, chloro, fluoro, bromo, amino, hydroxy, methyl, ethyl, propyl, oxo, dimethylamino, aminosulfonyl, cyclopropyl, cyano, hydroxymethyl, nitro, propenyl, trifluoromethyl, methoxy, ethoxy, trifluoromethoxy, carboxymethyl, morpholinylethylamino, propynyl, unsubstituted or substituted phenyl and unsubstituted or substituted heteroaryl selected from thienyl, furanyl, pyridyl, imidazolyl, and pyrazolyl; and pharmaceutically acceptable salts thereof.

7. Compound of claim 6 wherein $R^2$ is H; and pharmaceutically acceptable salts thereof.

8. Compound of claim 2 wherein R is selected from (4-pyridyl)—$CH_2$—, (4-pyrimidinyl)—$CH_2$—, (5-pyrimidinyl)—$CH_2$—, (6-pyrimidinyl)—$CH_2$—, (4-pyridazinyl)—$CH_2$—and (6-pyridazinyl)—$CH_2$—; wherein R is unsubstituted or substituted with one or more substituents selected from chloro, fluoro, amino, methylamino, hydroxy, methyl, ethyl, propyl, trifluormethyl, methoxy and ethoxy; and pharmaceutically acceptable salts thereof.

9. Compound of claim 2 wherein R is selected from (4-pyridyl)—$CH_2$—, (2-methylamino-4-pyrimidinyl)—$CH_2$—, (4-pyridazinyl)—$CH_2$—, (2-methoxy-4-pyridyl)—$CH_2$—, (4-pyridazinyl)—$CH_2$—, and (2-amino-4-pyrimidinyl)—$CH_2$—; and pharmaceutically acceptable salts thereof.

10. Compound of claim 2 wherein $R^3$ is selected from unsubstituted or substituted 6-membered nitrogen-containing heteroaryl; and wherein substituted $R^3$ is substituted with one or more substituents independently selected from halo, amino, $C_{1-3}$-alkoxy, hydroxyl, $C_{1-3}$-alkyl and $C_{1-2}$-haloalkyl; and pharmaceutically acceptable salts thereof.

11. Compound of claim 2 wherein $R^5$ is selected from H, piperidinylethyl and methoxyethoxyethyl; wherein $R^a$ is H; and wherein $R^b$ and $R^c$ are independently selected from H and trifluormethyl; and pharmaceutically acceptable salts thereof.

12. Compound of claim 2 wherein R is (4-pyridyl)—CH$_2$—; and pharmaceutically acceptable sails thereof.

13. Compound of claim 2 wherein $R^2$ is H or fluoro; and pharmaceutically acceptable salts thereof.

14. A Compound of claim 2 and pharmaceutically acceptable salts thereof selected from
- N-(3,3-dimethyl-2,3-dihydro-1H-indol-6-yl)-2-[(pyridin-4-ylmethyl)-amino]-benzamide;
- N-(1-acetyl-3,3-dimethyl-2,3-dihydro-1H-indol-6-yl)-2-[(pyridin-4-ylmethyl)-amino]-benzamide;
- N-(4,4-dimethyl-1,2,3,4-tetrahydro-isoquinolin-7-yl)-2-[(2-methylamino-pyrimidin-4-ylmethyl)-amino]-benzamide;
- (R)-N-(4,4-dimethyl-1,2,3,4-tetrahydro-isoquinolin-7-yl)-2-[1-(2-methylamino-pyrimidin-4-yl)-ethylamino]-benzamide;
- N-(1-Ethyl-3,3-dimethyl-2,3-dihydro-1H-indol-6yl)-2-[(pyridin-4-ylmethyl)-amino]-benzamide;
- N-(4,4-Dimethyl-1,2,3,4-tetrahydro-isoquinolin-7-yl)-2-[2-methoxy-pyridin-4-ylmethyl)-amino]-benzamide;
- N-(3,3-Dimethyl-2,3-dihydro-1H-indol-6-yl)-2-[(1-oxy-pyridin-4-ylmethyl)-amino]-benzamide;
- N-(4,4-Dimethyl-1,2,3,4-tetrahydro-isoquinolin-7-yl)-2-fluoro-6-[2-methoxy-pyridin-4-ylmethyl)-amino]-benzamide;
- N-(4,4-Dimethyl-1,2,3,4-tetrahydro-isoquinolin-7-yl)-3-fluoro-6-[(2-methoxy-pyridin-4-ylmethyl)-amino]-benzamide;
- N-(4,4-Dimethyl-1,2,3,4-tetrahydro-quinolin-7-yl)-2-[(1H-pyrrolo[2,3-b]pyridin-3-ylmethyl)-amino]-benzamide;
- N-(4,4-Dimethyl-1,2,3,4-tetrahydro-isoquinolin-7-yl)-2-[(pyridazin-4-ylmethyl)-amino]-benzamide;
- 2-[1-(2-Amino-pyrimidin-4-yl)-ethylamino]-N-(4,4-dimethyl-1,2,3,4-tetrahydro-isoquinolin-7-yl)-benzamide;
- N-(4,4-Dimethyl-1,2,3,4-tetrahydro-isoquinolin-7-yl)-2-[1-(2-methylamino-pyrimidin-4-yl)-ethylamino]-benzamide; and
- N-(4,4-Dimethyl-1,2,3,4-tetrahydro-isoquinolin-7-yl)-4-fluoro-6-[2-methoxy-pyridin-4-ylmethyl)-amino]-benzamide.

15. Compound of claim 2, and pharmaceutically acceptable salts thereof, comprising N-(3,3-dimethyl-2,3-dihydro-1H-indol-6-yl)-2-[(pyridin-4-ylmethyl)-amino]-benzamide.

16. Compound of claim 2, and pharmaceutically acceptable salts thereof, comprising N-(1-acetyl-3,3-dimethyl-2,3-dihydro-1H-indol-6-yl)-2-[(pyridin-4-ylmethyl)-amino]-benzamide.

17. Compound of claim 2, and pharmaceutically acceptable salts thereof, comprising N-(4,4-dimethyl-1,2,3,4-tetrahydro-isoquinolin-7-yl)-2-[(2-methylamino-pyrimidin-4-ylmethyl)-amino]-benzamide.

18. A pharmaceutical composition comprising a pharmaceutically-acceptable carrier and a compound of claim 1.

* * * * *